United States Patent [19]

Gandolfi et al.

[11] 4,307,112

[45] Dec. 22, 1981

[54] 9-DEOXY-9A-METHYLENE ISOSTERES OF PGI₂ AND PROCESS FOR THEIR PREPARATION

[75] Inventors: Carmelo Gandolfi, Milan; Carlo Passarotti, Gallarate; William Fava, Milan; Angelo Fumagalli, Monza; Franco Faustini; Roberto Ceserani, both of Milan, all of Italy

[73] Assignee: Farmitalia Carlo Erba S.p.A., Milan, Italy

[21] Appl. No.: 124,715

[22] Filed: Feb. 26, 1980

Related U.S. Application Data

[62] Division of Ser. No. 6,208, Jan. 24, 1979.

[30] Foreign Application Priority Data

Jan. 26, 1978 [IT] Italy .............................. 19616 A/78
Dec. 21, 1978 [IT] Italy .............................. 31073 A/78

[51] Int. Cl.³ .................. C07C 103/46; C07C 101/14
[52] U.S. Cl. ................................... 424/305; 562/498; 562/501; 260/464; 564/123; 564/152; 260/465 E; 564/155; 564/158; 424/248.54; 564/169; 564/170; 424/248.55; 564/189; 564/199; 424/248.56; 564/201; 564/203; 424/251; 564/340; 564/355; 424/263; 564/428; 564/460; 424/272; 424/273 P; 424/274; 424/275; 424/283; 424/285; 424/304; 424/309; 424/319; 424/320; 424/324; 424/325; 424/330; 542/421; 542/422; 542/429; 560/19; 560/45; 560/48; 560/116; 560/119; 562/433; 562/452; 562/455; 562/457
[58] Field of Search .................. 560/119, 45, 48, 19; 562/501, 498, 452, 455, 457, 433; 260/464, 465 E; 542/421, 429, 422; 564/155, 158, 152, 169, 170, 189, 123, 199, 261, 203, 460, 340, 355, 428; 424/304, 320, 324, 325, 330, 248.55, 248.54, 248.56, 251, 263, 272, 273 P, 274, 275, 283, 285, 305, 319, 309

[56] References Cited

U.S. PATENT DOCUMENTS

4,225,507  9/1980  Sih ....................................... 560/119

FOREIGN PATENT DOCUMENTS

15653  9/1980  European Pat. Off. ............ 560/119

*Primary Examiner*—Robert Gerstl
*Attorney, Agent, or Firm*—Murray and Whisenhunt

[57] ABSTRACT

9-deoxy-9A-methylene-isosteres of PGI₂, including processes for their preparation and pharmaceutical and veterinary compositions containing same, are disclosed. The compounds are useful as therapeutic agents, for example as anti-aggregating agents, disaggregating agents, and as vasodilators.

21 Claims, No Drawings

9-DEOXY-9A-METHYLENE ISOSTERES OF PGI$_2$ AND PROCESS FOR THEIR PREPARATION

This is a division of application Ser. No. 6,208, filed Jan. 24, 1979.

The object of this invention is 9-deoxy-9a-methyleneisosteres of PGI$_2$, also known as 6,9α-oxide-11α,15(S)-dihydroxy-prosta-5(Z),13(E)-dienoic acid, including a procedure for their preparation as well as pharmaceutical and veterinary compositions containing them.

Compounds covered by this invention have the following general formula (I)

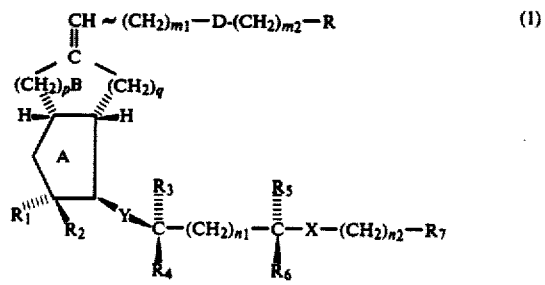

wherein

R is chosen from the group (a) a free or esterified carboxy group; (b) —C(OR')$_3$, where each R' group is independently C$_1$–C$_6$alkyl or phenyl; (c) —CH$_2$—R", where R" is hydroxy or C$_2$–C$_7$alkoxy; (d)

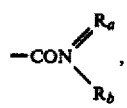

where R$_a$ and R$_b$ are chosen independently from the group hydrogen, C$_1$–C$_6$alkyl, C$_2$–C$_6$alkanoyl and phenyl; (e) —C≡N; (f) a

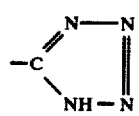

radical; (g) —CHO; (h) a

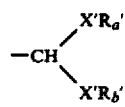

radical where each X' is independently —O— or —S— and the R'$_a$ and R'$_b$ groups, whether the same or different, are C$_1$–C$_6$alkyl or together form a straight or branched C$_2$–C$_6$ alkylene chain;

D is from the group: —CH$_2$—, >CH—OH,

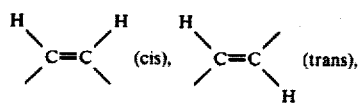

—C≡C—, >C=O, —O—, —S—, and >N—R$_c$, where R$_c$ may be hydrogen, C$_1$–C$_6$alkyl or C$_2$–C$_6$alkanoyl;

one of R$_1$ and R$_2$ and, independently, one or R$_3$ and R$_4$ is hydrogen, C$_1$–C$_6$alkyl, C$_2$–C$_{10}$alkenyl, C$_2$–C$_{10}$alkynyl, phenyl, or aryl-C$_1$–C$_6$alkyl and the other is hydrogen, hydroxy, C$_1$–C$_6$alkoxy or aryl-C$_1$–C$_6$alkoxy, or, R$_1$ and R$_2$ and, independently, R$_3$ and R$_4$ together form an oxo group;

each R$_5$ and R$_6$, whether the same or different, may be hydrogen, C$_1$–C$_6$-alkyl or halogen, preferably fluorine, or R$_5$, R$_6$ and the carbon atom to which they are bound form a >C=CH$_2$ or

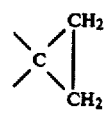

radical;

Y is chosen from the group: —CH$_2$CH$_2$—, —C≡C—,

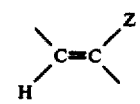

(trans),

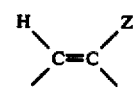

(cis) where Z is hydrogen or halogen, —NH—CO— and —NH—CH$_2$—;

X is chosen from the group: —(CH$_2$)—$_{m3}$ in which m$_3$ is zero or 1,

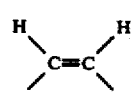

(cis),

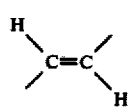

(trans), —O—, —S— and >N—R$_c$ with R$_c$ as defined above;

m$_1$, m$_2$, n$_1$ and n$_2$, whether the same or different, may be zero or an integer between 0 and 12 such that each sum m$_1$+m$_2$ and n$_1$+n$_2$ is less than or equal to 15;

p and q are independently zero or an integer between 1 and 3 such that the sum p+q is an integer of 1 to 6;

R$_7$ is chosen from the group: (a') hydrogen; (b') C$_1$–C$_4$-alkyl; (c') a cycloaliphatic radical, either unsubstituted or substituted with one or more C$_1$–C$_6$-alkyl or C$_1$–C$_6$-alkoxy; (d') an aryl group, either unsubstituted or substituted with one or more of the following: halogen, halo-C$_1$–C$_6$-alkyl, $C_1$–$C_6$-alkyl, $C_1$–$C_6$-alkoxy, phenyl; (e') a saturated or unsaturated heterocyclic ring, either unsubstituted or substituted with one or more of the following: halogen, halo-$C_1$–$C_6$-alkyl, $C_1$–$C_6$-alkoxy, phenyl, $C_1$–$C_6$ alkyl.

This invention also covers lactones derived from compounds with formula (I), as well as pharmaceutically or veterinarily acceptable salts, optical antipodes, and geometric isomers and diastereoisomers of compounds with formula (I), plus their mixtures.

In this discussion, a dashed line (''') refers to substituents on a ring in the α configuration, that is, below the plane of the ring, to substituents on a bicyclo[(p+q+1).3.0]alkane system (composed of condensed rings A and B) in the endo configuration, and to substituents on a chain in the S configuration. A wedged line (—), on the other hand, refers to a ring substituent in the β configuration, that is above the plane of the ring, to a bicyclo[(p+q+1).3.0]alkane substituent in the exo configuration, and to a side chain substituent in the R configuration. A wavy line ($\zeta$) indicates a substituent of undefined stereochemistry: ring substituents may be α or β, bicycloalkane substituents may be endo or exo, and side chain substituents may be R or S.

The compounds with formula (I) and their derivatives described here have a cis junction between condensed rings A and B; the hydrogen atoms bound to the bicyclic system at the junction are both outside the dihedral angle formed by the rings in the natural configuration.

The side chain on cyclopentane ring A (the ω chain) is trans with respect to ring B and exo with respect to the bicyclic system.

In the compounds covered by this invention, there are 2 possible geometric isomers arising from the configuration of the double bond exocyclic to ring B, depending on whether the chain bound to this double bond (chain α) is on the same side as or the opposite side from the chain on cyclopentane ring A (chain ω): in the first case, the exocyclic double bond is defined as cis; in the second, it is trans. In both formula (I) and the formulas which follow, the symbol ~ means that both geometric isomers are covered by this invention, both separately and in mixtures.

The above notation refers to natural compounds. However, the enantiomers covered by this invention show stereochemistry at all asymmetric sites which is the opposite of that found in the natural compounds. They are thus mirror images of the latter, and their names include the prefix "ent" to indicate precisely that. d,l mixtures contain equimolar quantities of the natural compounds and the corresponding enantiomers.

The alkyl, alkenyl, alkynyl, alkoxy and alkanoyloxy groups may be straight or branched, unsubstituted or substituted with one or more of the following: halogen, $C_1$–$C_6$-alkoxy and aryl, phenyl in particular.

R is preferably a free or esterified carboxylic group, or its derivative salt.

A $C_1$–$C_6$alkyl group is preferably methyl, ethyl or propyl.

A $C_2$–$C_7$acyloxy group is preferably $C_2$–$C_6$alkanoyloxy, for example, acetoxy, propionyloxy, or benzoyloxy.

A $C_2$–$C_6$alkanoyl group is preferably acetyl or propionyl.

A $C_2$–$C_6$alkylene radical is preferably ethylene or propylene.

A $C_1$–$C_6$-alkoxy group is preferably methoxy, ethoxy or propoxy.

An aryl-$C_1$–$C_6$-alkyl group is preferably benzyl.

An aryl-$C_1$–$C_6$-alkoxy group is preferably benzyloxy.

A $C_2$–$C_{10}$-alkenyl group is preferably —CH=CH—$R_8$, where $R_8$ is hydrogen or straight or branched $C_1$–$C_8$-alkyl, but preferably a vinyl group.

A $C_2$–$C_{10}$-alkynyl group is preferably —C≡C—$R_8$, where $R_8$ is as defined above, but preferably an ethynyl group.

A halo-$C_1$–$C_6$-alkyl group is preferably trihalo-$C_1$–$C_6$-alkyl, particularly trifluoromethyl.

When Z is halogen, chlorine or bromine is preferred.

Preferably, $R_5$ and $R_6$ are independently chosen from hydrogen, $C_1$–$C_6$-alkyl and fluorine.

When $R_7$ is $C_1$–$C_4$-alkyl, methyl is preferred.

When $R_7$ is aryl, then phenyl, α-naphthyl or β-naphthyl is preferred.

When $R_7$ is a cycloaliphatic radical, it may be mono-, bi- or tricyclic. If monocyclic, $C_3$–$C_9$-cycloalkyl or cycloalkenyl is preferred, like cyclopentyl, cyclohexyl, cycloheptyl, cyclopentenyl, cyclohexenyl, cycloheptenyl. If bicyclic, norbornyl is preferred. If tricyclic, adamantyl is preferred.

When $R_7$ is a cycloaliphatic radical, a monocycloaliphatic group as defined above is preferred.

When $R_7$ is a heterocylic ring, this may be mono- or bicyclic, containing as heteroatom at least one of N, S and O. However, the heterocycle is preferably monocyclic as defined above, particularly tetrahydrofuryl, tetrahydrothienyl, tetrahydropyranyl, pyrrolyl, pyrazolyl, oxazolyl, isoxazolyl, pyridyl, pyrazinyl, pyrimidinyl, pyridazinyl.

When R is an esterified carboxyl group, —COOR$_9$ is preferred, where $R_9$ is a $C_1$–$C_{12}$-alkyl radical, particularly methyl, ethyl, propyl, heptyl or $C_2$–$C_{12}$-alkenyl, allyl in particular.

Preferably, $m_1$, $m_2$, $n_1$ and $n_2$ are independently zero, 1, 2 or 3.

Pharmaceutically or veterinarily acceptable salts of compounds with formula (I) may be formed with both inorganic and organic acids and bases.

Pharmaceutically or veterinarily acceptable inorganic acids include hydrochloric, hydrobromic and sulfuric; while organic acids include citric, fumaric, tartaric malic, maleic, methanesulfonic and ethanesulfonic. Acceptable inorganic bases may be the hydroxides of alkali or alkaline earth metals, zinc and aluminum. Acceptable organic bases may be amines like methylamine, diethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and other similar aliphatic, aromatic and heterocyclic amines like piperidine, morpholine, pyrrolidine, piperazine, as well as substituted derivatives like 1-methylpiperidine, 4-ethylmorpholine, 1-isopropylpyrrolidine, 2-methylpyrrolidine, 1,4-dimethylpiperazine, 2-methylpiperidine, hydrophilic derivatives like mono-, di- and triethanolamine, 2-amino-2-butanol, 2-amino-1-butanol, 2-amino-2-ethyl-1,3-propanediol, 2-amino-2-methyl-1-propanol, tris-(hydroxymethyl)aminomethane, N-phenylethanolamine, N-(p-tert-amylphenyl)diethanolamine, ephedrine, procain, and α & β amino acids like lysine and arginine.

Under this invention, the preferred salts are compounds with formula (I) in which R is —COOR$_d$, where $R_d$ is a pharmaceutically or veterinarily acceptable cation derived from one of the bases listed above.

In this discussion, the compounds covered by the invention will be referred to as bicyclo[(p+q+1).3.0-]alkane derivatives, or, preferably, as derivatives of a 20 carbon atom compound, the prostacyclanoic acid, with the following formula:

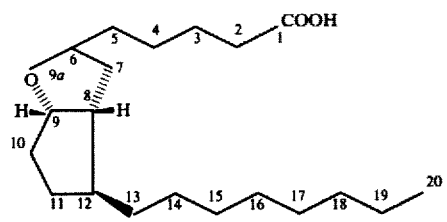

in which the position of the oxygen atom is called the 9a position.

Therefore, a compound with formula (I) in which p=q=1 is a bicyclo[3.3.0]octyl derivative or, preferably, a derivative of a 9a-deoxy-9a-methylene prostacyclanoic acid, since a methylene group has taken the place of the heteroatom in position 9a of the prostacyclanoic acid. A compound with formula (I) in which p=2 and q=1 is a bicyclo[4.3.0]nonyl derivative, or, preferably, a derivative of 9a-deoxy-9a,9b-dimethylene prostacyclanoic acid, since 2 methylene groups have substituted the heteroatom in position 9a of the prostacyclanoic acid. Analogously, a compound with formula (I) in which p=3 and q=1 is a bicyclo[5.3.0]dodecyl derivative or, preferably, a derivative of 9a-deoxy-9a,9b,9c-trimethylene prostacyclanoic acid.

Analogous prostacyclanoic acid derivatives in which q=2 or q=3 are called "7a-homo" or "7a,7b-dihomo" respectively, while compounds with formula (I) with p or q equal to zero are called "9a-nor-methylene" or "7-nor-methylene" respectively.

The same notation (homo, dihomo, nor, dinor, etc.) is used to indicate lengthening (the former) or shortening (the latter) of the α and ω chains by one, two or more carbon atoms, relative to the number of carbon atoms in prostacyclanoic acid.

As examples of this nomenclature, the following two compounds (Ia) and (Ib) are named in full:

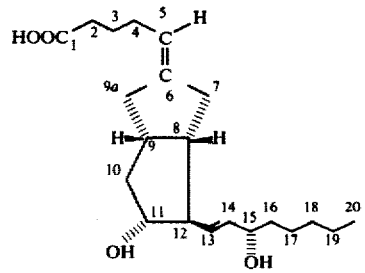

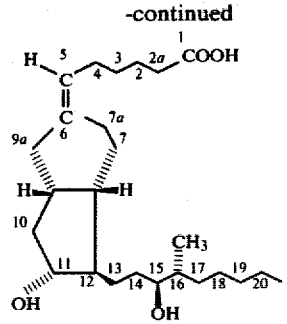

(Ia): 7-endo-hydroxy-6-exo-(3''S-hydroxy-oct-1'-trans-1'-enyl)bicyclo[3.3.0]octyl-3(5')-pent-5'-trans-enoic acid; or 5t,13t-11α,15S-dihydroxy-9a-deoxy-9a-methylene-prostacyclan-5,13-dienoic acid;

(Ib): 8-endo-hydroxy-7-exo-(3''R-hydroxy-4'S-methyl-non-1'-yl)bicyclo[4.3.0]nonyl-3(6')-hex-6'-cis-enoic acid; or 5c-11α,15R-dihydroxy-16S,20-dimethyl-9a-deoxy-9a-methylene-7a,2a-dihomoprostacycl-5-enoic acid.

Under this invention, preferred compounds with formula (I) are those in which R is a free or salified carboxy group; $R_7$ is a straight or branched $C_1$-$C_4$-alkyl, phenyl optionally substituted as described above, a saturated monoheterocycle (preferably tetrahydrofuryl or tetrahydrothienyl) or a $C_5$-$C_7$-monocycloalkyl radical and the other substituents have the meanings reported above.

The following compounds are particularly preferred under this invention:

5c,13t-11α,15S-dihydroxy-9a-deoxy-9a-methylene-prostacycla-5,13-dienoic acid;

5c,13t,-11α,15R-dihydroxy-9a-deoxy-9a-methylene-prostacycla-5,13-dienoic acid;

5c-11α,15S-dihydroxy-9a-deoxy-9a-methylene-prostacycl-5-enoic acid, and its 15R epimer;

5c-11α,15S-dihydroxy-9a-deoxy-9a-methylene-prostacycl-5-en-13-ynoic acid and its 15R epimer;

a 16S-methyl derivative of the above mentioned acids;

a 20-methyl derivative of the above mentioned acids;

5c,13t-4-oxo-11α,15S-dihydroxy-9a-deoxy-9a-methylene-prostacycla-5,13-dienoic acid;

5c,13t-4S,11α15S-trihydroxy-9a-deoxy-9a-methylene-prostacycla-5,13-dienoic acid-1,4-γ-lactone, and its 4R epimer;

sodium salt of 5c,13t-4S,11α,15S-trihydroxy-9a-deoxy-9a-methylene-prostacycla-5,13-dienoic acid, and its 4R epimer;

5c,13t-11α,15S-dihydroxy-9a-deoxy-9a-methylene-17-cyclohexyl-18,19,20-trinor-prostacycla-5,13-dienoic acid;

5c,13t-11α,15S-dihydroxy-9a-deoxy-9a-methylene-17-phenyl-18,19,20-trinor-prostacycla-5,13-dienoic acid;

5c,13t-11α,15S-dihydroxy-9a-deoxy-9a-methylene-17(2')-tetrahydrofuryl-18,19,20-trinor-prostacycla-5,13-dienoic acid;

5c,13t-11α,15S-dihydroxy-9a-deoxy-9a-methylene-16-m-trifluoromethylphenoxy-17,18,19,20-tetranor-prostacycla-5,13-dienoic acid;

5c,13t-11α,15(S)-dihydroxy-9a-deoxy-9a-methylene-16-methyl-16-butoxy-18,19,20-trinor-prostacycla-5,13-dienoic acid;

5c-11α,15S-dihydroxy-9a-deoxy-9a-methylene-16R-fluoro-prostacycl-5-en-13-ynoic acid;

5t,13t-11α,15S-dihydroxy-9a-deoxy-9a-methylene-prostacycla-5,13-dienoic acid;

5t,13t-11α,15R-dihydroxy-9a-deoxy-9a-methylene-prostacycla-5,13-dienoic acid;

5t-11α,15S-dihydroxy-9a-deoxy-9a-methylene-prostacycl-5-enoic acid and its 15R epimer;

5t-11α,15S-dihydroxy-9a-deoxy-9a-methylene-prostacycl-5-en-13-ynoic acid, and its 15R epimer;

a 16S-methyl derivative of the above mentioned acids;

a 20-methyl derivative of the above mentioned acids;

5t,13t-4-oxo-11α,15S-dihydroxy-9a-deoxy-9a-methylene-prostacycla-5,13-dienoic acid;

5t,13t-4S,11α, 15S-trihydroxy-9a-deoxy-9a-methylene-prostacycla-5,13-dienoic acid-1,4-γ-lactone, and its 4R epimer;

sodium salt of 5t-13t-4S-11α,15S-trihydroxy-9a-deoxy-9a-methylene-prostacycla-5,13-dienoic acid, and its 4R epimer;

5t,13t-11α,15S-dihydroxy-9a-deoxy-9a-methylene-17-cyclohexyl-18,19,20-trinor-prostacycla-5,13-dienoic acid;

5t,13t-11α,15S-dihydroxy-9a-deoxy-9a-methylene-17-phenyl-18,19,20-trinor-prostacycla-5,13-dienoic acid;

5t-13t-11α,15S-dihydroxy-9a-deoxy-9a-methylene-17(2')-tetrahydrofuryl-18,19,20-trinor-prostacycla-5,13-dienoic acid;

5t,13t-11α,15S-dihydroxy-9a-deoxy-9a-methylene-16-m-trifluoromethylphenoxy-17,18,19,20-tetranor-prostacycla-5,13-dienoic acid;

5t,13t-11α,15S-dihydroxy-9a-deoxy-9a-methylene-16-methyl-16-butoxy-18,19,20-trinor-prostacycla-5,13-dienoic acid;

5t-11α,15S-dihydroxy-9a-deoxy-9a-methylene-16R-fluoro-prostacycl-5-en-13-ynoic acid;

5c,13t-11α,15S-dihydroxy-9a-deoxy-9a-nor-methylene-prostacycla-5,13-dienoic acid;

5c-11α,15S-dihydroxy-9a-deoxy-9a-nor-methylene-20-methyl-13,14-didehydro-prostacycla-5-en-13-ynoic acid;

5c,13t-11α,15S-dihydroxy-9a-deoxy-7-nor-methylene-prostacycla-5,13-dienoic acid;

5c,13t-11α,15S-dihydroxy-9a-deoxy-7-nor-methylene-17-phenyl-18,19,20-trinor-prostacycla-5,13-dienoic acid;

5c-11α,15S-dihydroxy-9a-deoxy-7-nor-methylene-16S-fluoro-13,14-didehydro-prostacycla-5-en-13-ynoic acid and the 16R-fluoro isomer thereof;

5c,13t-11α,15S-dihydroxy-9a-deoxy-9a,9b-dimethylene-prostacycla-5,13-dienoic acid;

5c-11α,15S-dihydroxy-9a-deoxy-9a,9b-dimethylene-prostacycla-5-en-13-ynoic acid;

5c,13t-11α,15S-dihydroxy-9a-deoxy-9a,9b-dimethylene-17-cyclohexyl-18,19,20-trinor-prostacycla-5,13-dienoic acid;

5c,13t-11α,15S-dihydroxy-9a-deoxy-9a,7a-homo-dimethylene-prostacycla-5,13-dienoic acid;

5c,13t-11α,15S-dihydroxy-9a-deoxy-9a,7a-homo-dimethylene-15-methyl-prostacycla-5,13-dienoic acid;

5c,13t-11α,15S-dihydroxy-9a-deoxy-9a,7a-homo-dimethylene-16S-methyl-prostacycla-5,13-dienoic acid and the 16R-methyl isomer thereof;

5c,13t-10α,15S-dihydroxy-9a-deoxy-9a,7a-homo-dimethylene-16-phenoxy-17,18,19,20-tetranor-prostacycla-5,13-dienoic acid;

5c-11α,15S-dihydroxy-9a-deoxy-9a,7a-homo-dimethylene-prostacycla-5-en-13-ynoic acid;

5c,13t-11α,15S-dihydroxy-9a-deoxy-9a,9b,7a-homo-trimethylene-2-nor-prostacycla-5,13-dienoic acid;

5t,13t-11α,15S-dihydroxy-9a-deoxy-9a-nor-methylene-prostacycla-5,13-dienoic acid;

5t-11α,15S-dihydroxy-9a-deoxy-9a-nor-methylene-20-methyl-13,14-didehydro-prostacycla-5-en-13-ynoic acid;

5t,13t-11α,15S-dihydroxy-9a-deoxy-7-nor-methylene-prostacycla-5,13-dienoic acid;

5t,13t-11α,15S-dihydroxy-9a-deoxy-7-nor-methylene-17-phenyl-18,19,20-trinor-prostacycla-5,13-dienoic acid;

5t-11α,15S-dihydroxy-9a-deoxy-7-nor-methylene-16S-fluoro-13,14-didehydro-prostacycla-5-en-13-ynoic acid and the 16R-fluoro isomer thereof;

5t,13t-11α,15S-dihydroxy-9a-deoxy-9a,9b-dimethylene-prostacycla-5,13-dienoic acid;

5t-11α,15S-dihydroxy-9a-deoxy-9a,9b-dimethylene-prostacycla-5-en-13-ynoic acid;

5t,13t-11α,15S-dihydroxy-9a-deoxy-9a,9b-dimethylene-17-cyclohexyl-18,19,20-trinor-prostacycla-5,13-dienoic acid;

5t,13t-11α,15S-dihydroxy-9a-deoxy-9a,7a-homo-dimethylene-prostacycla-5,13-dienoic acid;

5t,13t-11α,15S-dihydroxy-9a-deoxy-9a,7a-homo-dimethylene-15-methyl-prostacycla-5,13-dienoic acid;

5t,13t-11α,15S-dihydroxy-9a-deoxy-9a,7a-homo-dimethylene-16S-methyl-prostacycla-5,13-dienoic acid and the 16R-methyl isomer thereof;

5t,13t-11α,15S-dihydroxy-9a-deoxy-9a,7a-homo-dimethylene-16-phenoxy-17,18,19,20-tetranor-prostacycla-5,13-dienoic acid;

5t-11α,15S-dihydroxy-9a-deoxy-9a,7a-homo-dimethylene-prostacycla-5-en-13-ynoic acid;

5t,13t-11α,15S-dihydroxy-9a-deoxy-9a,9b,7a-homo-trimethylene-2-nor-prostacycla-5,13-dienoic acid;

as well as the 11-deoxy-derivatives, the 11-epimers, the 15R-hydroxy isomers and all the enantiomers of the compounds indicated above as well as their pharmaceutically or veterinarily acceptable salts.

The compounds covered by this invention are prepared with the following procedure:

(1) alkylation of compound (II)

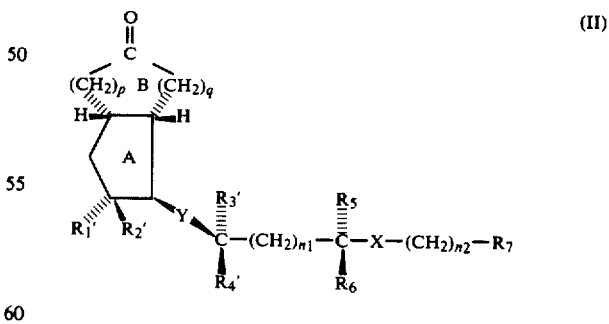

wherein p, q, Y, n₁, n₂, X, R₅, R₆ and R₇ are as defined above; one of R₁' and R₂' and, independently, one of R₃' and R₄' is hydrogen, $C_1$-$C_6$-alkyl, $C_2$-$C_{10}$-alkenyl, $C_2$-$C_{10}$-alkynyl, phenyl or aryl-$C_1$-$C_6$-alkyl and the other is hydrogen, hydroxy, $C_1$-$C_6$-alkoxy, aryl-$C_1$-$C_6$-alkoxy or a protecting group bound to the bicyclic system or the side chain through an ether linkage, or R₁' and R₂' and, independently, R₃' and R₄' together form a protecting group for the ketone function, with a compound with formula (III)

$$E-CH-(CH_2)_{m1}-D-(CH_2)_{m2}-R''' \quad (III)$$
$$(-)$$

wherein D, $m_1$ and $m_2$ are as defined above; E is a $(C_6H_5)_3P-$ or a $(R_eO)_2P\rightarrow(O)-$ group where each $R_e$ may independently be $C_1-C_6$-alkyl or phenyl; R''' is chosen from: (a'') a carboxylic group, free, esterified or as its salt; (b'') $-C(OR')_3$, where R' is as defined above; (c'') $-CH_2-R^{IV}$, where $R^{IV}$ is $C_2-c_7$-acyloxy or a protecting group bound to $-CH_2-$ through an ether linkage; (d'')

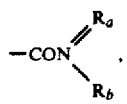

where $R_a$ and $R_b$ are as defined above; (e'') $-C\equiv N$; (f'') a

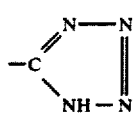

radical; (g'') a

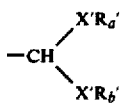

radical where X', $R_a'$ and $R_b'$ are as defined above), followed as desired by the removal of any protecting group present;

(2) alkylation of a compound with formula (IV)

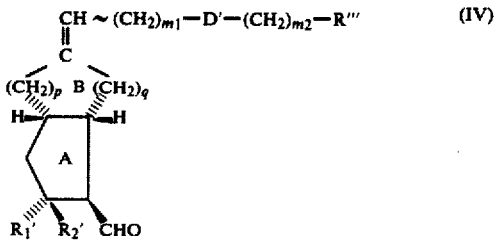

wherein R''', $m_2$, $m_1$, p, q, $R_1'$ and $R_2'$ are as defined above and D' is chosen from the group: (a''') $-O-$; b''') $-S-$; (c''') $>N-R_c$ where $R_c$ is as defined above; (d''') $-CH=CH-$ (cis) (e''') $-CH=CH-$ (trans); (f''') $-C\equiv C-$; (g''') a

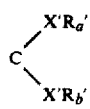

radical where X', $R_a'$ and $R_b'$ are as defined above; (h''') a $>CH-OCOR'$ group where R' is as defined above; (i''') $-CH_2-$; or D', R''' and $-(CH_2)_{m2}-$ form a 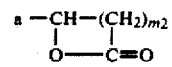

group, where $m_2$ is as defined above, with a compound with formula (V)

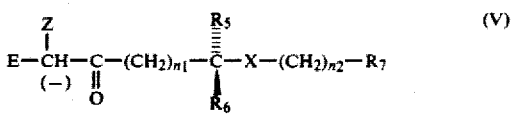

wherein E, Z, $n_1$, $R_5$, $R_6$, X, $n_2$ and $R_7$ as defined above) to afford a compound with formula (VI)

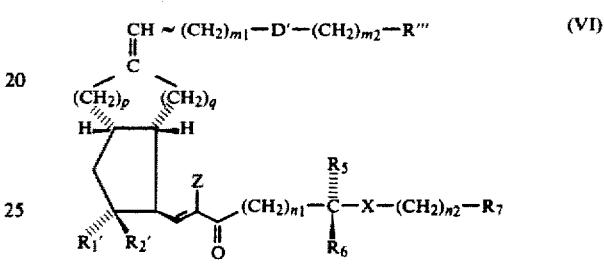

in which R''', $m_2$, D', $m_1$, p, q, $R_1'$, $R_2'$, Z, $n_1$, $R_5$, $R_6$, X, $n_2$ and $R_7$ are as defined above and, if desired, the protecting groups in a compound with formula (VI) may be removed to give a compound with formula (I) in which Y is $-CH=CZ-$ (trans), Z is as defined above, and $R_3$ and $R_4$ together form an oxo group and/or, if desired, a compound with formula (VI) in which Z is hydrogen or one with formula (I) in which Y is $-CH=CZ-$ (trans), Z is hydrogen, and $R_3$ and $R_4$ together form an oxo group may be reduced to give, after the protecting groups are removed, a compound with formula (I) in which Y is $-CH_2-CH_2-$ and $R_3$ and $R_4$ together form an oxo group and/or, if desired, nucleophilic addition to the free carbonyl on the ω chain of a compound with formula (VI) or one with formula (I) in which Y is $-CH_2-CH_2-$ or $-CH=CZ-$ (trans), Z is as defined above, and $R_3$ and $R_4$ together form an oxo group affords, upon removal of any protecting groups, a compound with formula (I) in which Y is $-CH_2-CH_2-$ or $-CH=CZ-$ (trans), Z is as defined above, and one of $R_3$ and $R_4$ is hydroxy while the other is hydrogen $C_1-C_6$-alkyl, $C_2-C_{10}$-alkenyl, $C_2-C_{10}$-alkynyl, phenyl or aryl-$C_1-C_6$-alkyl and, if desired, the ether derivative may be prepared from a compound with formula (I) in which Y is $-CH_2-CH_2-$ or $-CH=CZ-$ (trans), Z is as defined above, one of $R_3$ and $R_4$ is hydroxy while the other is hydrogen, $C_1-C_6$-alkyl, $C_2-C_{10}$-alkenyl, $C_2-C_{10}$-alkynyl, phenyl or aryl-$C_1-C_6$-alkyl, and any other hydroxyl groups present are protected as described above, to give after any protecting groups are removed a compound of formula (I) in which Y is $-CH_2-CH_2-$ or $-CH=CZ-$ (trans), Z is as defined above, and one of $R_3$ and $R_4$ is $C_1-C_6$-alkoxy or aryl-$C_1-C_6$-alkoxy while the other is hydrogen, $C_1-C_6$-alkyl, $C_2-C_{10}$-alkenyl, $C_2-C_{10}$-alkynyl, phenyl or aryl-$C_1-C_6$-alkyl and/or, if desired, a compound with formula (I) in which Y is $-CH=CZ-$ (trans), Z is halogen, one of $R_3$ and $R_4$ is hydrogen, $C_1-C_6$-alkyl, $C_2-C_{10}$-alkenyl, $C_2-C_{10}$-alkynyl, phenyl or aryl-$C_1-C_6$-alkyl while the other is hydroxy, $C_1-C_6$-alkoxy or aryl-$C_1-C_6$-alkoxy, or R₃ and R₄ together form an oxo group, and any hydroxy, oxo or carboxy groups present are free or protected as defined above, may be dehydrohalogenated to give, after any protecting groups are removed, a compound with formula (I) in which Y is —C≡C— and one of R₃ and R₄ is hydrogen, C₁-C₆-alkyl, C₂-C₁₀-alkenyl, C₂-C₁₀-alkynyl, phenyl or aryl-C₁-C₆-alkyl while the other is hydroxy, C₁-C₆-alkoxy or aryl-C₁-C₆-alkoxy or R₃ and R₄ together form an oxo group. and/or, if desired, the lactone or salt derivatives of a compound with formula (I) may be prepared and/or, if desired, a free compound with formula (I) may be prepared from its salt and/or, if desired, a mixture of isomeric compounds with formula (I) may be separated into its individual isomers. In the processes described above, if one or more substituents are specified for a compound, the others are all as previously defined for formula (I).

Protecting groups for the hydroxyl functions are ether or ester residues readily converted to hydroxyl groups under mild conditions, for instance acid hydrolysis. Preferred groups include silyl ethers: for instance trialkylsilyl ethers like trimethyl, dimethyl-tert-butyl, dimethyl-isopropyl, or dimethylethylsilyl ether; and also acetal and enol ether residues: for instance, tetrahydropyranyl ether, tetrahydrofuranyl ether, dioxanyl ether, oxathianyl ether,

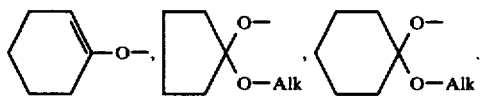

where Alk is C₁-C₆-alkyl.

Ketone protecting groups are preferably ketal and thioketal residues:

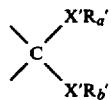

groups in which X', Rₐ' and R_b' are as defined above.

Alkylations of a compound (II) with a compound (III) are run in the same way as those of a compound (IV) with a compound (V) by using at least a 1.1 molar equivalent excess of (III) (or (V)) per mole of (II) (or (IV)). The reaction may be run in any inert solvent e.g. in a linear or cyclic ether like diethyl ether, tetrahydrofuran, dioxane or dimethoxyethane; in an aliphatic or aromatic hydrocarbon like n-hexane, n-heptane, benzene or toluene; in a halogenated hydrocarbon like dichloromethane or carbon tetrachloride, as well as in mixtures of these solvents.

Especially when E in compounds (III) or (V) is (C₆H₅)₃P—, dimethylsulfoxide, hexamethylphosphoramide, and other aprotic solvents are particularly useful. Dimethylsulfoxide gives the dimethylsulfinyl carbanion upon reaction with an alkali hydride which in turn can generate carbanions with formula (III) and (V) from the corresponding phosphoranes and phosphonates; this solvent is thus particularly preferred, since carbanions (III) and (V) can then be generaed in situ.

For the alkylations described above, the reaction temperature may range from the freezing point to the boiling point of water, although room temperature is particularly preferred.

Reaction of a compound (II) with a compound (III) gives a mixture of geometric isomers, in that the new exocyclic double bond formed in the reaction may be cis or trans. Reaction between a compound (IV) and a compound (V) gives only one or both of these cis and trans isomers, depending on whether the compound (IV) used was cis, trans or a mixture of the two. If desired, the individual geometric isomers may be separated by fractional crystallization from a suitable solvent or by chromatography, either thin layer, column or liquid-liquid at low, medium or high pressure. Silica gel or magnesium silicate may be used as support with a solvent like cyclohexane, n-hexane, benzene, methylene chloride, ethyl ether, isopropyl ether, ethyl acetate or methyl acetate as the mobile phase.

When necessary, the ether protecting groups may be removed from the hydroxyl functions with mild acid hydrolysis, for instance with mono- or poly-carboxylic acids like acetic, formic, citric, oxalic, or tartaric in a solvent like water, acetone, tetrahydrofuran, dimethoxyethane or a low molecular weight alcohol, or with a sulfonic acid like p-toluene-sulfonic in a low molecular weight alcohol like anhydrous ethanol or methanol, or with a polystyrene-sulfonic resin. For example, a 0.1–0.25 N polycarboxylic acid (like oxalic or citric) is used with a suitable low-boiling solvent miscible with water and readily removable under vacuum at the end of the reaction.

Silyl ether residues may be selectively removed in the presence of other protecting groups with F⁻ ions in solvents like tetrahydrofuran and dimethylformamide.

Ester protecting groups may be removed by following typical saponification procedures.

Ketal and thioketal protecting groups for ketones are generally removed as are acetal or thioacetal groups, with mild acid hydrolysis as described above.

Thioketals and thioacetals may be selectively removed in the presence of other protecting groups with, for instance, mercuric chloride in aqueous acetone or acetonitrile, or a mixture of them, in the presence of an alkaline earth carbonate like that of calcium or magnesium.

The optional reduction of a compound (VI) in which Z is hydrogen or of a compound (I) in which Y is —CH=CZ— (trans) wherein Z is hydrogen, and R₃ and R₄ together form an oxo group to afford, after any protecting groups are removed, a compound (I) in which Y is —CH₂—CH₂— and R₃ and R₄ together form an oxo group is preferably run in liquid ammonia, with or without a co-solvent (for instance, an aliphatic alcohol like tert-butanol or a 2-C₁-C₄-alkylpropan-2-ol, or a cyclic ether like tetrahydrofuran or dioxane), with an excess of an alkali or alkaline earth metal like lithium, sodium, potassium or calcium. At the end of the reaction, a weak acid like ammonium chloride or sulfate or an aliphatic alcohol like ethanol or propanol is used as a protons source. The reaction temperature may range from −70° C. to that of the solvent at reflux.

Nucleophilic addition to the free carbonyl group on the ω chain in a compound (VI) or in a compound (I) in which Y is —CH₂—CH₂— or —CH=CZ— (trans), Z is as defined above, and R₃ and R₄ together form an oxo group gives a secondary or tertiary alcohol, depending on the nucleophile.

A secondary alcohol is preferably prepared with an alkali or alkaline earth (like sodium, lithium, calcium or magnesium) borohydride or with zinc borohydride to give, after any protecting groups are removed, a compound (I) in which Y is —CH₂—CH₂— or —CH=

CZ— (trans), Z is as defined above, and one of $R_3$ and $R_4$ is hydrogen and the other is hydroxy. 0.5–6 moles of reducig agent are used per mole of the carbonyl derivative (VI) or (I), in an aqueous or anhydrous solvent; for instance, a linear or cyclic ether like ethyl ether, tetrahydrofuran, dimethoxyethane or dioxane, an aliphatic or aromatic hydrocarbon like n-heptane or benzene, a halogenated hydrocarbon like methylene chloride, or a hydroxyl-containing solvent like methyl, ethyl or isopropyl alcohol, as well as mixtures of these. The reaction temperature may range from $-40°$ C. to the boiling point of the solvent, but is preferably between $-25°$ C. and $+25°$ C.

A tertiary alcohol is prepared by reaction with an organometallic derivative to give, after any protecting groups are removed, a compound (I) in which Y is —$CH_2$—$CH_2$— or —CH=CZ— (trans), Z is as defined above, and one of $R_3$ and $R_4$ is $C_1$–$C_6$-alkyl, $C_2$–$C_{10}$-alkenyl, $C_2$–$C_{10}$-alkynyl, phenyl or aryl-$C_1$–$C_6$-alkyl while the other is hydroxy. The organometallic may be a magnesium derivative like $R_{10}MgHal$ (in which $R_{10}$ is $C_1$–$C_6$-alkyl, $C_2$–$C_{10}$-alkenyl, phenyl or aryl-$C_1$–$C_6$-alkyl and Hal is halogen, preferably chlorine or bromine), a lithium cuprate like $R_{10}CuLi$ ($R_{10}$ as above), an organolithium derivative like $R_{10}Li$ ($R_{10}$ as above), or an alkali or alkaline earth acetylide $(R_{11}—C\equiv C—)^-_n M^{n+}$ (in which n is 1 or 2, $R_{11}$ is hydrogen, straight or branched $C_1$–$C_8$-alkyl, aryl-$C_1$–$C_6$-alkyl, or aryl, particularly phenyl, and M is an alkali or alkaline earth metal). The reaction between the carbonyl compound and one of these organometallic derivatives is preferably run with 1.05 moles (or slightly more) of reagent per mole of compound, in an anhydrous solvent: for instance, an aprotic solvent like dimethylsulfoxide or hexamethylphosphoramide, a linear or cyclic ether like ethyl ether, tetrahydrofuran, anisole, dioxane or dimethoxyethane, or an aliphatic or aromatic hydrocarbon like n-heptane, n-hexane, benzene or toluene. The reaction temperature may range from approximately $-70°$ C. to the boiling point of the solvent, but is preferably between $-60°$ C. and $20°$ C.

Whether it is a secondary or tertiary alcohol, the product of this nucleophilic addition is a mixture of the epimeric S and R alcohols. The individual S

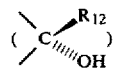

and R

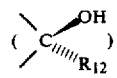

alcohols (in which $R_{12}$ is hydrogen, $C_1$–$C_6$-alkyl, $C_2$–$C_{10}$-alkenyl, $C_2$–$C_{10}$-alkynyl, phenyl or aryl-$C_1$–$C_6$-alkyl) may be separated as desired using the fractional crystallization and chromatography techniques described above.

The optional preparation of ethers from these secondary and tertiary alcohols to give, after any protecting groups are removed, compounds with formula (I) in which Y is —$CH_2$—$CH_2$— or —CH=CZ— (trans), Z is as defined above, and one of $R_3$ and $R_4$ is $C_1$–$C_6$-alkoxy or aryl-$C_1$–$C_6$-alkoxy while the other is hydro-gen, $C_1$–$C_6$-alkyl, $C_2$–$C_{10}$-alkenyl, $C_2$–$C_{10}$-alkynyl, phenyl or aryl-$C_1$–$C_6$-alkyl, may be effected by reaction with an optionally aryl-substituted diazoalkane in the presence of a catalyst like fluoroboric acid or boron trifluoride in an organic solvent like dichloromethane. Alternatively, it may be done by reaction of the hydroxyl group (either free or as its salt) with an alkyl or arylalkyl halide in the presence of a base like silver oxide, in a solvent like dimethylsulfoxide or dimethylformamide.

The optional dehydrohalogenation of a compound with formula (I) in which Y is —CH=CZ— (trans), Z is halogen one of $R_3$ and $R_4$ is hydroxy, $C_1$–$C_6$-alkoxy or aryl-$C_1$–$C_6$-alkoxy while the other is hydrogen, $C_1$–$C_6$-alkyl, $C_2$–$C_{10}$-alkenyl, $C_2$–$C_{10}$-alkynyl, phenyl, aryl-$C_1$–$C_6$-alkyl or $R_3$ and $R_4$ together form an oxo group to give the corresponding compound (I) in which Y is —$C\equiv C$— is effected with a dehydrohalogenating agent preferably chosen from: $CH_3$—SO—$CH_2^\ominus$, diazabicycloundecene, diazabicyclononene, and an alkali metal amide or alcoholate. 1–5 moles (preferably 1.5–1.8) of dehydrohalogenating agent is used per mole of compound (I), and the reaction is preferably run in an oxygen-free atmosphere in an inert solvent like dimethylsulfoxide, dimethylformamide, hexamethylphosphoramide, a linear or cyclic ether or an aliphatic or aromatic hydrocarbon like those listed above, liquid ammonia, or a mixture of these solvents at a temperature ranging from $-60°$ C. to the boiling point of water. In the absence of ammonia, room temperature is preferred.

This optional dehydrohalogenation of a compound (I) in which Y is —CH=CZ— (trans) and Z is halogen to give the corresponding derivative in which Y is —$C\equiv C$— may precede the carbonyl nucleophilic addition and the successive preparation of ethers from the product alcohol.

The following reactions are all run using standard procedures: optional transformation of a compound with formula (I) into another, optional lactone or salt preparation, preparation of the free compound (I) from its salt, and separation of individual isomers from a mixture.

For example, a compound with formula (I) in which $R_3$ and $R_4$ are both hydrogen may be prepared from one in which one of $R_3$ and $R_4$ is hydrogen while the other is hydroxy by preparing the tosylate from the alcohol, for instance by treatment with tosyl chloride in the presence of base, and reducing the tosylate with $NaBH_4$ or $NaB(CN)H_3$ in water, aqueous alcohol or dimethylformamide or with $LiAlH_4$ in an anhydrous solvent like ethyl ether or tetrahydrofuran, at a temperature ranging from room temperature to the boiling point of the solvent. Analogously, a compound with formula (I) in which $R_1$ and $R_2$ are both hydrogen may be prepared from one in which one of $R_1$ and $R_2$ is hydrogen while the other is hydroxy, and a compound (I) in which D is —$CH_2$— may be prepared from one in which D is >CH—OH.

A compound with formula (I) in which $R_3$ and $R_4$ together form an oxo group may be prepred from one in which one of $R_3$ and $R_4$ is hydrogen while the other is hydroxy by selective oxidation with excess activated $MnO_2$ in an inert, preferably chlorinated solvent like methylene chloride or chloroform at room temperature or, alternatively, with 1.1–1.2 molar equivalents of dichlorodicyanobenzoquinone in an inert solvent like dioxane, benzene or a mixture at a temperature ranging from 40° C. to the boiling point of the solvent.

In an analogous fashion a compound with formula (I) in which $R_1$ and $R_2$ together form an oxo group may be prepared from one in which one of $R_1$ and $R_2$ is hydrogen while the other is hydroxy, and a compound (I) in which D is >C=O may be prepared from one in which D is >CH—OH.

When only one of several secondary alcohol functions is to be oxidized, the others must be protected as described above; the protecting groups are then removed at the end of the reaction.

A compound with formula (I) in which one of $R_1$ and $R_2$ is $C_1$–$C_6$-alkoxy or aryl-$C_1C_6$-alkoxy may be prepared from one in which one of $R_1$ and $R_2$ is hydroxy through etherification analogous to that described for a compound with formula (I) in which one or $R_3$ and $R_4$ is hydroxy. Again, when only one of several secondary alcohol functions is to react, the others must be protected; the protecting groups are then removed at the end of the reaction.

A compound with formula (I) in which R is a carboxylic ester group (for instance, a $C_1$–$C_{12}$-alkoxycarbonyl) may be prepared from one in which R is a free carboxylic group by following standard procedures, for example reaction with an appropriate alcohol, like a $C_1$–$C_{12}$-aliphatic alcohol, in the presence of an acid catalyst, like p-toluenesulfonic acid, or alternatively, treatment with a diazoalkane.

The optional conversion of a compound with formula (I) in which R is an esterified carboxyl group (i.e., a $C_1$–$C_{12}$-alkoxycarbonyl) to one in which R is a free carboxyl group may be effected using standard saponification procedures: treatment with an alkali or alkaline earth hydroxide in water or aqueous alcohol, followed by acidificatiion.

The optional preparation of a compound with formula (I) in which R is —$CH_2$—R'' (R''=hydroxy) from one in which R is a free or esterified carboxyl group may be effected by reduction of the ester with LiAlH$_4$ in ethyl ether or tetrahydrofuran at reflux.

The optional conversion of a compound with formula (I) in which R is a free carboxyl group to one in which R is

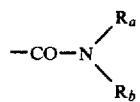

($R_a$ and $R_b$ as defined above) may be effected by treatment with an amine HNR$_a$R$_b$ in the presence of a condensing agent, for instance a carbodiimide like dicyclohexylcarbodiimide. A compound with formula (I) in which R is a carboxylic ester may be converted into one in which R is

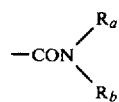

by treatment with an amine HNR$_a$R$_b$ in a suitable organic solvent at reflux for 2–3 hours.

The optional preparation of a compound with formula (I) in which R is a

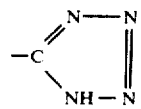

radical from one in which R is a free carboxyl group may be effected by forming first the corresponding acid halide (preferably chloride, perhaps with thionyl or oxalyl chloride in refluxing dichloroethane or dioxane), then the amide derivative (for example, with ammonia), followed by dehydration to the nitrile (for instance with p-toluenesulfonyl chloride in pyridine at 90°–100° C.) and finally reaction of the nitrile with sodium azide and ammonium chloride in dimethylformamide at a temperature ranging from room temperature to 100° C. This reaction of the carboxyl group to give —CN or

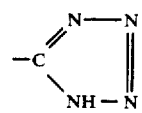

is preferably run on the starting material.

The optional conversion of a compound with formula (I) in which R is a free or esterified carboxyl group into one in which R is —CHO may be effected using standard procedures, for instance the preparation of the corresponding chloride from the acid or ester and subsequent Rosenmund reaction as described in Org. Reactions,4,362(1948).

A compound with formula (I) in which R is —C-(OR')$_3$ (R' as defined above) may be prepared from one in which R is a free or esterified carboxyl group by reacting the hydrochloride of the carboximide ester (prepared with standard methods) with a suitable alcohol, according to the procedure described in J. Amer. Chem. Soc.,64,1827(1942), for example.

Acetalization, for example the optional preparation of a compound with formula (I) in which R is

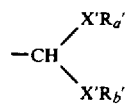

where X' is oxygen and $R_a'$ and $R_b'$ are as defined above) is effected by reaction of the aldehyde with an alcohol or glycol in the presence of a catalyst like p-toluenesulfonic acid or a sulfonic resin in a solvent which allows the removal of the water fromed by azeotropic distillation, by an exchange reaction with acetone-dioxolane in which acetone is removed as it forms, or by reaction with an ortho-ester in which the alcohol is distilled away as it forms. The acetal may also be prepared from the corresponding thioacetal by reaction with a suitable alcohol or glycol in the presence of a mercuric salt (preferably HgCl$_2$) as an exchange catalyst and an alkalien earth carbonate, in an inert solvent.

Thioacetalization, for example the optional preparation of a compound with formula (I) in which R is

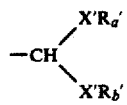

(where X′ is sulfur and $R_a'$ and $R_b'$ are as defined above) from one in which R is —CHO, is preferably effected by reaction with a mono- or dimercaptan like methylmercaptan, ethylmercaptan, dithioethyleneglycol or dithiopropyleneglycol in the presence of a catalyst like boron trifluoride etherate in an inert solvent, preferably a halogenated or aromatic hydrocarbon (methylene chloride, chloroform, benzene, toluene).

The corresponding ketals and thioketals may be prepared from ketones by following the procedure described above for acetals and thioacetals.

Lactone and salt preparation from a compound with formula (I), as well as preparation of compound (I) from its salt, are performed using standard procedures.

Individual isomers are separated from mixtures of isomeric compounds (I) using standard techniques like fractional crystallization and chromatography.

Compounds with formula (III) in which E is $(R_eO)_2p\rightarrow(O)-(R_e$ as defined above) are prepared by reacting a compound (VII)

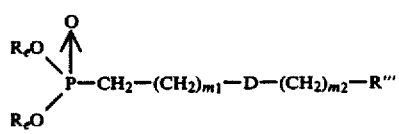

in which $R_e$, $m_1$ D, $m_2$ and R‴ are as defined above, with at least one molar equivalent of one of the following bases: an alkali or alkaline earth hydride like sodium, potassium, lithium or calcium hydride, an alkali or alkaline earth alcoholate like sodium or potassium tert-butylate, an alkali or alkaline earth amide like sodium amide, or an alkali or alkaline earth salt of a carboxyamide, like N-sodioacetamide and N-sodiosuccinimide.

Compounds with formula (III) in which E is $(C_6H_5)_3P$— are prepared by reacting a compound with formula (VIII)

in which $m_1$, D, $m_2$ and R‴ are as defined above and Hal is halogen, with 1.1–1.3 molar equivalents of triphenylphosphine in an organic solvent like benzene, acetonitrile or diethyl ether and then treating the product phosphonium salt with an equivalent quantity of an inorganic base like NaOH, KOH, $Na_2CO_3$ or $NaHCO_3$.

Compounds with formula (V) are prepared in an analogous fashion to that described above for the preparation of compounds (III): from compounds with formula (IX)

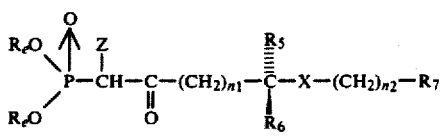

wherein $R_e$, Z, $n_1$, $R_5$, $R_6$, X, $n_2$ and $R_7$ are defined above, or from compounds with formula (X)

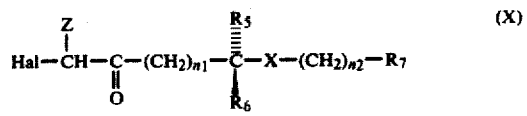

wherein Hal, Z, $m_1$, $R_5$, $R_6$, X, $n_2$ and $R_7$ are as defined above

Compounds with formulas (VII) and (IX) are prepared using standard methods, for example those described by Corey et al. in *J. Amer. Chem. Soc.*, 90, 3247 (1968) and 88, 5654 (1966). Compounds (VIII) and (X) are also prepared following standard procedures.

Compounds with formulas (II) and (IV) are new compounds covered by this invention, as are procedures for their preparation.

Compounds with formula (II) in which Y is —CH$_2$—CH$_2$—, —C≡C— or —CH=CZ— (trans), Z as defined above, are prepared in a procedure involving:

($a^{IV}$) Reaction of a compound with formula (XI)

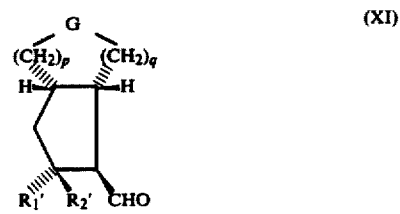

wherein p, q, $R_1'$ and $R_2'$ are as defined above and G is a protected carbonyl group or a group >CH—OG′ wherein G′ is a silyl ether or acetal ether residue, with a compound of formula (V) to afford a compound of formula (XII)

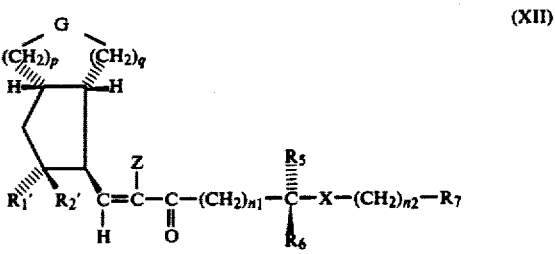

wherein G, p, q, $R_1'$, Z, $R_2'$, $n_1$, $R_5$, $R_6$, X, $n_2$ and $R_7$ are as defined above;

($b^{IV}$) Optional conversion of a compound with formula (XII) into a compound of formula (XIII)

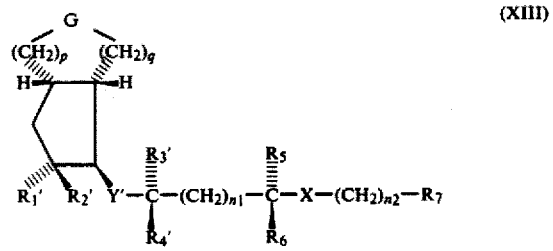

in which G, p, q, $R_1'$, $R_2'$, $R_3'$, $R_4'$, $n_1$, $R_5$, $R_6$, X, $n_2$ and $R_7$ are as defined above, and Y′ is —CH$_2$—CH$_2$—, —C≡C—, or —CH=CZ— (trans), Z as defined above;

($c^{IV}$) Removal of the protecting group in G to afford a compound of formula (XIV)

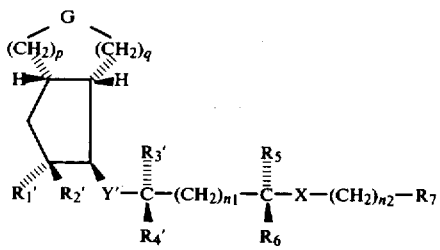
(XIV)

wherein q,p,$R'_1$,$R'_2$,Y',$R'_3$,$R'_4$,$n_1$,$R_5$,$R_6$,X,$n_2$ and $R_7$ are as defined above and G" is >CH~OH or >C=O;

($d^{IV}$) Optional oxidation of a compound of formula (XIV) wherein G" is hydroxy and the other hydroxy groups, if present, are protected as reported above.

Compounds with formula (II) in which Y is —NH—CH$_2$— are prepared by reacting a compound with formula (XV)

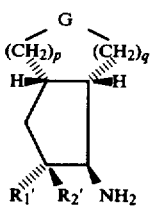
(XV)

wherein G, p and q are as defined above and $R'_1$ and $R'_2$ are as defined above with the exception of hydroxy, with an aldehyde (XVI)

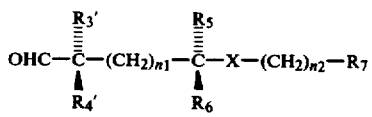
(XVI)

in which $R_3'$, $R_4'$, $n_1$, $R_5$, $R_6$, X, $n_2$ and $R_7$ are as defined above, in the presence of a reducing agent, followed by removal of the protecting group in G and, optionally, of the other protecting groups, if present.

Compounds with formula (II) in which Y is

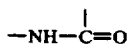

are prepared by reacting a compound (XV) with a compound (XVII)

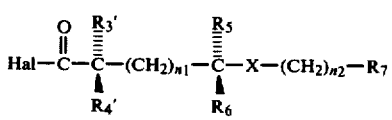
(XVII)

in which Hal is halogen, preferably chlorine, and $R_3'$, $R_4'$, $n_1$, $R_5$, $R_6$, X, $n_2$ and $R_7$ are as defined above, in the presence of a base, followed by removal of the protecting group in G and, optionally, of the other protecting groups, if present.

The reaction between a compound with formula (XI) and one with formula (V) is run in the same way as that reported above for compounds (IV) and (V).

The optional conversion of a compound with formula (XII) into one with formula (XIII) is effected with reactions analogous to those described above for the preparation of one compound with formula (I) from another: for example, nucleophilic addition to the carbonyl on the ω chain, etherification of the product alcohols, dehydrohalogenation and hydrogenation.

As stated above, when G is a group >CH~OG', the protecting group G' may be a silyl ether residue (for instance, a trialkylsilyl ether like trimethyl, dimethyl-tert-butyl, dimethylisopropyl, or dimethylethylsilyl ether, but preferably dimethyl-tert-butyl) or an acetal ether residue (for instance, tetrahydropyranyl ether, tetrahydrofuranyl ether, dioxanyl ether, oxathianyl ether, but preferably tetrahydropyranyl).

The protecting group G' in a compound with formula (XIII) is removed as described previously: that is, selectively, with $F^-$ for a silyl ether and with acid hydrolysis for an acetal ether. When a protecting group G' must be removed in the presence of other labile ether groups, these latter should be acetal ethers when OG' is a silyl ether or silyl ethers when OG' is an acetal ether.

When G is a protected carbonyl group it is preferably protected as acetal or thioacetal, for example a dimethoxyacetal, a diethoxyacetal, a dimethylthioacetal, a diethylthioacetal, preferably a dimethoxyacetal, or as ketal, or thioketal for example a ethylendioxyketal

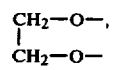

a propylendithioketal

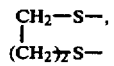

a propylendioxyketal

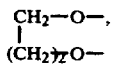

a ethylendithioketal

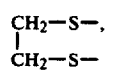

preferably a ethylendioxyketal.

The removal of said protecting groups in a compound of formula (XIII) as well as the optional protection of the free hydroxy groups in a compound of formula (XIV), e.g. as acetal ethers or silyl ethers, may be effected as previously reported.

The optional oxidation of a compound of formula (XIV) wherein G" is hydroxy, may be effected using standard oxidation procedures for secondary alcohols: for example treatment of the alcohol in an organic solvent like acetone with a solution of chromic anhydride in sulfuric acid, following normal procedures.

The reductive amination reaction between a compound with formula (XV) and an aldehyde (XVI) is run under reaction conditions typical for this procedure, preferably using a mixed hydride like NaBH$_4$ or LiAlH$_4$ as reducing agent.

The reaction between compounds with formulas (XV) and (XVII) is run under the normal conditions for acylating amines.

Compounds with formula (IV) are prepared in a procedure involving:
(a$^V$) Reaction of a compound with formula (XVIII)

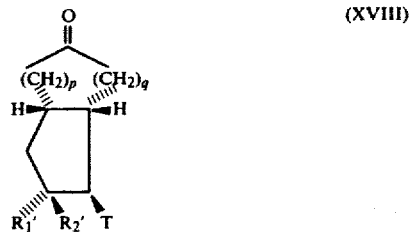

(XVIII)

in which p, q, $R_1'$ and $R_2'$ are as defined above, T is a protected aldehyde function

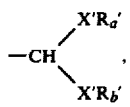

X', $R_a'$ and $R_b'$ as defined above) with a compound of formula (III) to give a compound with formula (XIX)

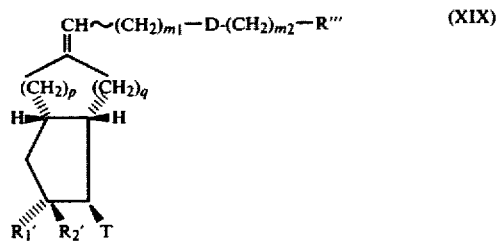

(XIX)

wherein R''', $m_2$, D, $m_1$, p, q, $R'_1$, $R'_2$ and T are as defined above;

(b$^V$) Optional conversion of a compound with formula (XIX) into one with formula (XX)

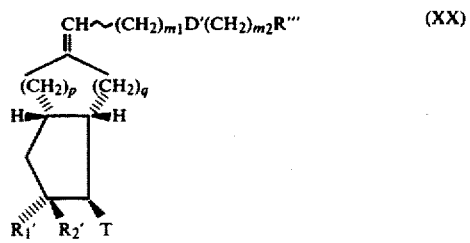

(XX)

in which R''', $m_2$, D', $m_1$, p, q, $R'_1$, $R'_2$ and T are as defined above;

(c$^V$) And finally removal of the aldehyde protecting groups in T.

The reaction between compounds with formulas (XVIII) and (III) is run under conditions analogous to those reported above for the reaction between compounds (II) and (III) to afford a mixture of two isomeric olefins differing in configuration (cis or trans) at the newly formed exocyclic double bond. The individual isomers with formula (XIX) may be separated with fractional crystallization or chromatography, as described previously.

The optional conversion of a compound with formula (XIX) into one with formula (XX) may be effected as described above for the analogous reactions involving compounds with formula (I). For example, a compound with formula (XX) in which D is >CH〰OCOR' (R' as defined above) may be prepared from a compound (XIX) in which D is >CH〰OH with the usual esterification methods for alcohols. Also, a compound (XX) in which D' is

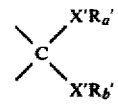

(X', $R_a'$ and $R_b'$ as defined above) may be prepared from a compound (XIX) in which is >C=O with the usual ketalization and thioketalization procedures.

The aldehyde protecting groups in a compound with formula (XX) are removed as described previously, preferably by acid hydrolysis when the aldehyde is protected as an acetal or by treatment with mercuric chloride when it is protected as a thioacetal. When the aldehyde protecting group must be removed selectively in the presence of other protected carbonyl functions, these latter should be acetals or ketals if the aldehyde is a thioacetal and thioacetals or thioketals when the aldehyde is an acetal.

Compounds with formula (XI) are prepared with a procedure involving:
(a$^{VI}$) Conversion of a compound (XXIA) or (XXIB)

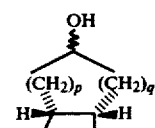

(XXIA)

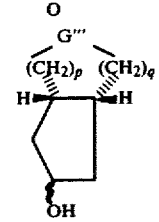

(XXIB)

in which p and q are as defined above and G''' is a protected carbonyl group as reported above, into a compound (XXII)

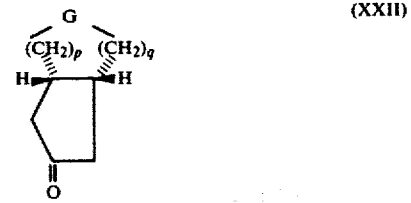

(XXII)

in which p, q, and G are as defined above;
(b$^{VI}$) Reaction of compound (XXII) with a compound O=C(OR$_{13}$)$_2$ in which R$_{13}$ is a C$_1$-C$_6$-alkyl or aryl- $C_1$–$C_6$-alkyl to give a compound with formula (XXIII)

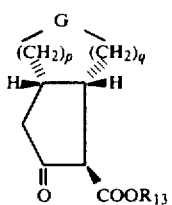

(XXIII)

in which p, q, G and $R_{13}$ are as defined above;
($c^{VI}$) Reduction of the product compound (XXIII) to a compound with formula (XXIV)

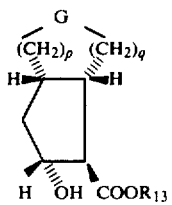

(XXIV)

in which G, p, q and $R_{13}$ are as defined above;
($d^{VI}$) Optional separation of compound (XXIV) into the individual optical antipodes;
($e^{VI}$) Optional conversion of compound (XXIV) into a compound with formula (XXV)

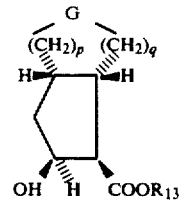

(XXV)

in which G, p, q and $R_{13}$ are as defined above;
($f^{VI}$) Transformation of a compound (XXIV) or (XXV) into a compound with formula (XXVI)

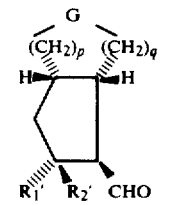

(XXVI)

wherein G, p, q, $R'_1$ and $R'_2$ are as defined above.

A compound of formula (XXII) wherein G is a group >CH∽OG′, in which G′ is as defined above may be prepared from one of formula (XXIA) by known methods, e.g. by reaction in the presence of base, with a silyl halide, a silazane or a silyl trifluoroacetamide or, for example, by reaction with a vinyl ether

where X″ is —O—, —S— or —(CH$_2$)$_r$(r=0,1), according to known procedures.

A compound of formula (XXII), in which G is a protected carbonyl, may be prepared from one of formula (XXIB) by oxidation in pyridine with an excess of the pyridine-chromic anhydride complex, or by oxidation according to Moffatt in a mixture of benzene and dimethylsolphoxide with cholicyclohexylcarbodiimide in the presence of pyridinium trifluoroacetate.

The reaction between a compound with formula (XXII) and O=C(OR$_{13}$)$_2$ (R$_{13}$ as defined above, but preferably methyl) is run in the presence of 2–4 moles of a base like sodium methoxide, sodium ethoxide, sodium or potassium hydride or potassium tert-butoxide, with an excess of 6–12 moles of carbonic diester per mole of ketone, neat or in an inert solvent in an oxygen- and water-free atmosphere. The temperature may range from approximately 0°–80° C. (preferably 60°–80° C.) for a period between 10 minutes and 1 hour. The yield varies from 5% to 90%, depending on the temperature, the reaction time and the concentration.

A compound with formula (XXIII) may be reduced with an alkali or alkaline earth borohydride in aqueous solution, preferably at a pH between 5.3 and 7.2, or at −20° C. with ethanolic NaBH$_4$ in methylene chloride/ethanol. Generally, the reduction is complete in 30 minutes and the excess reagent is quenched by adding a readily reducable species, like acetone, and a proton donor, like acetic acid.

The individual optical antipodes of a compound with formula (XXIV), in which G is as defined above, may be separated by saponifying the ester using standard procedures, forming a salt of the product acid with an optically active base like quinine, chinconine, ephedrine, 1-phenyl-1-aminoethane, dihydroabietylamine, amphetamine or arginine, and separating the resulting diastereomeric salts by fractional crystallization, for example. The optically active acid is then recovered by conversion to the sodium salt and subsequent acidification of its aqueous solution to a pH which does not interfere with the protecting group in G. Optionally the hydrolysis of the protecting groups may precede the optical resolution: the protecting groups are then restored at the end of the separation process.

The optically active free acid prepared in this way is then converted to an optically active ester (XXIV) using standard procedures, for instance treatment with a suitable diazoalkane.

If desired, using an identical procedure, a racemic mixture of compounds (XXV) may be separated into individual optical antipodes.

Alternatively, compounds (XXIV) and (XXV) wherein G is a protected carbonyl group may be resolved into their optical antipodes de-protecting the carbonyl group in G, reacting this with an optically active primary amine, for example arginine, lysine, alanine, 1-phenyl-1-ethyl-amine, 1-phenyl-1-propyl-amine and similar, to give the corresponding optically active diastereoisomeric Schiff bases; these may be separated by known methods, e.g. by fractionate crystallization or by HPLC, the imino group may be hydrolized to >C=O in a known manner then the separated optically active keto-esters may be transformed into the optical antipodes (XXIV) and (XXV) by ketalization or acetalization in a conventional way.

The optional conversion of a compound with formula (XXIV) to one with formula (XXV) may be done on either a racemic mixture or the individual isomers separated as described above. In this transformation, the configuration of the free hydroxyl on the cyclopentane ring is inverted. The procedure involves esterification of the hydroxyl, for example by treatment with 2–4 molar equivalents of triphenylphosphine and 2–4 molar equivalents of a carboxylic acid like acetic, benzoic or p-phenylbenzoic, or with 2–4 molar equivalents of ethyl azo-bis-carboxylate in an inert solvent like an aromatic hydrocarbon, perhaps halogenated, like benzene or chlorobenzene, or a cyclic ether like tetrahydrofuran, and subsequent selective saponification of the ester function formed in this way, for example by transesterification in an inert alcohol $R_{13}OH$ in the presence of an alkali carbonate, preferably $K_2CO_3$.

A compound with formula (XXVI) is prepared from a compound (XXIV) or (XXV) using known methods. For example, the free hydroxyl group in compound (XXIV) or (XXV) may be converted to a $C_1$–$C_6$-alkoxy, an aryl-$C_1$–$C_6$-alkoxy or a labile ether like a silyl or acetal ether using the ether preparation techniques already described for the analogous reactions of compounds with formula (I).

The free hydroxyl group in a compound with formula (XXIV) or (XXV) may be oxidized to an oxo group, and the product ketone may be converted to a ketal or thioketal according to the procedure described above for compounds with formula (I) to afford a tertiary alcohol.

A hydrogen atom may replace the free hydroxyl group in a compound with formula (XXIV) or (XXV), for example, by treatment with a sulfonic acid chloride like p-toluenesulfonyl, methanesulfonyl or benzenesulfonyl chloride and subsequent reduction of the product sulfonate, for instance with $LiAlH_4$ in standard methods. In this case the carboxylic ester group (—$COOR_3$) is reduced at the same time to the primary alcohol (—$CH_2OH$), which may then be oxidized to the aldehyde with Moffatt's reagent.

A product compound with formula (XXVII)

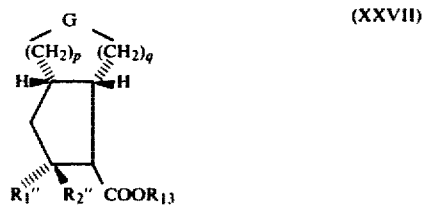

(XXVII)

in which one of of $R_1''$ and $R_2''$ is hydrogen, $C_1$–$C_6$-alkyl, $C_2$–$C_{10}$-alkenyl, aryl or aryl-$C_1$–$C_6$-alkyl while the other is hydroxy, $C_1$–$C_6$-alkoxy, aryl-$C_1$–$C_6$-alkoxy or a labile ether group, or $R_1''$ and $R_2''$ together form a ketone protecting group may be converted to the corresponding compound with formula (XXVI) by reduction following standard procedures, for example, with diisobutylaluminum hydride or lithium diisobutylaluminum hydride.

When a compound (XXVII) is reduced with $LiAlH_4$ following standard procedures, the product is the corresponding primary alcohol which may also be prepared from the free acid by standard reduction with $BH_3$ in tetrahydrofuran. The free acid is prepared by saponification of the ester. This primary alcohol may then be oxidized to the aldehyde, with Mofatt's reagent, for example, as mentioned previously.

Compounds with formula (XV) are prepared using known methods, starting for example from a compound with formula (XXVII) in which any secondary alcohol functions are protected as acetal ethers if —OG' is a silyl ether, or as a silyl ether if —OG' is an acetal ether. For example, a compound with formula (XV) may be prepared from one with formula (XXVII) in a procedure involving:

($a^{VII}$) Optional selective removal of protecting group in G;

($b^{VII}$) Optional oxidation of the free hydroxyl group, in case liberated from >CH—OG', to a ketone, for example with Jones' reagent;

($c^{VII}$) Saponification of the ester to the acid;

($d^{VII}$) Conversion of the acid to a mixed anhydride, for example by reaction with an acid chloride like an alkyl, benzyl, or pivaloylchlorocarbonate in an inert anhydrous solvent like acetone, tetrahydrofuran or methylene chloride;

($e^{VII}$) Conversion of the mixed anhydride to an azide by treatment, for example, with an acetone solution of an alkali metal azide;

($f^{VII}$) Preparation of an amine from the azide through a Curtius rearrangement;

($g^{VII}$) And finally optional conversion of the product amine with formula (XV) into another.

Compounds with formulas (XVI) and (XVII) are known compounds, available through known methods.

Compounds with formula (XVIII) are prepared from a compound (XI) in which, when G is a group >CH—OG', G' is preferably a silyl ether residue and, when one of $R_1'$ and $R_2'$ is hydrogen while the other is hydroxy, the latter is protected, preferably as an acetal ether or as an ester, with the following steps:

($a^{VIII}$) Conversion of the aldehyde to an acetal or thioacetal group (preferably thioacetal)

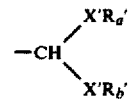

($X'$, $R_a'$ and $R_b'$ as defined above);

($b^{VIII}$) Optional selective removal of the group G with $F^-$ ions;

($c^{VIII}$) Optional oxidation of the free hydroxyl group to the ketone with Jones' reagent;

($d^{VIII}$) Optional selective removal of the protecting group ($R_1'$ or $R_2'$) from the secondary hydroxyl group.

Compounds with formula (XXIA) and (XXIB) are prepared with known methods. For example, a compound (XXIA) in which $p=q=1$ is prepared by selective reduction of bicyclo[3.3.0]octane-3,7-dione (J. Amer. Chem. Soc.,82,6347(1960)) or by reduction of bicyclo[3.3.0]octane-3,7-dione-monoketal (J. Org. Chem.,39,2377(1974)), followed by removal of the ketal from the carbonyl function. In both cases, the product hydroxy ketone (XXI) with $p=q=1$ is a mixture of the endo-hydroxy and exo-hydroxy derivatives, with approximately 80% endo. The two isomers may readily be separated, using the corresponding racemic silyloxy derivative, by fractional crystallization or chromatography, as described several times above.

A compound with formula (XXI) in which $p=1$ and $q=2$ is prepared from bicyclo[4.3.0]non-7-en-3-one (XXVIII), which has a cis junction between the two rings, in a procedure

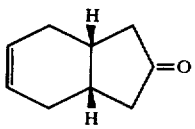
(XXVIII)

involving the protection of the ketone as a ketal or thioketal (as described above), standard hydroboration of the double bond, and subsequent removal of the ketone protecting group as described above.

Compound (XXVIII) may be synthesized, for example, as described by J. P. Vidal in "Stereochimiè et Selectivite Reactionelle en Serie Bicyclo[n.3.0]alcanique", presented at the Universitè de Sciences et Tecniques du Languedoc, Academie de Montpelier, n° d'orde C.N.R.S.A.O. 11257(1975).

A compound with formula (XXIA) in which p=1 and q=2 (prepared, for example, as described above) may be converted to other (XXI) derivatives by successive detalization or thioketalization, oxidation, Bayer-Willinger and formulation of the product using methods analogous to those reported above.

A compound of formula (XXIB) wherein p is zero and q is 1 or p is 1 and q is zero may be prepared from the bromidrine 5-exo-bromo-6-endo-hydroxy-bicyclo[2.3.0]heptan-2-one [J. Chem. Soc., Perkin, 1, 1767 (1965)] by known methods: for example said bromidrine may be converted into its acetal, thioacetal, ketal or thioketal, then dehalogenated to the compound (XXIB) using the known methods of organic chemistry such as, for example, the reduction with chromium (II) salts, the catalytic hydrogenation in the presence of Pd/CaCO₃ or Pd/C and in the presence of an halohydric acid acceptor, or the reduction with tributyl tin hydride.

A compound of formula (XXIB) wherein p is 2 and q is 1 or q is 2 and p is 1, may be prepared, e.g., from a compound of formula (XXVIII) by a process comprising: reducing the carbonyl group to alcohol, e.g. with LiAlH₄ in ethyl ether, protecting the alcoholic group, e.g. as tetrahydropyranylether or silyl ether, hydroborating, by conventional methods, the olefinic double bond, oxidizing, deblocking the protected hydroxy group, following the acetalization or ketalization.

A compound of formula (XXIB) wherein p=q=2 may be prepared by known methods e.g. from 2-hydroxy-perhydro-azulen-6-one which in turn may be obtained as described by D. K. Banerjee and K. Sankara Ram. in Ind. J. of Chem. vol. X, page 1 (1972). The compound of formula (XXVIII) may be used as starting material also for the preparation of the compounds of formula (XI) wherein G is a group >CH⁓OG' wherein G' is the residue of a silyl ether and wherein, when one of R'₁ and R'₂ is hydrogen and the other is hydroxy, the latter is preferably protected as acetal ether or as ester, following the reaction scheme reported below:

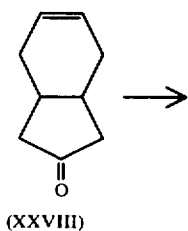
(XXVIII)

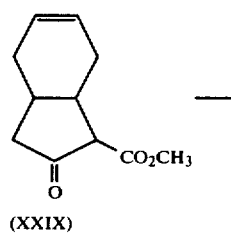
(XXIX)

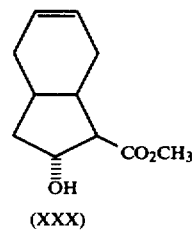
(XXX)

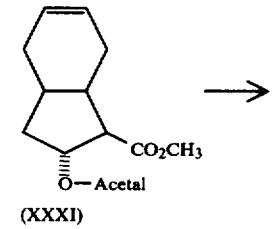
(XXXI)

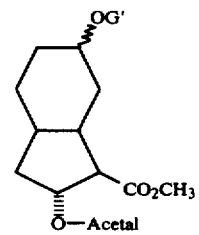
(XXXIIa : G' = H)
(XXXIIb : G' = silyl-ether residue)

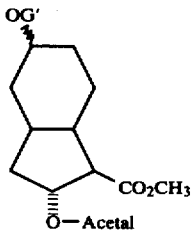
(XXXIIIa : G' = H)
(XXXIIIb : G' = silyl-ether residue)

The compound (XXVIII), by known methods, e.g. those previously reported, is converted into the β-keto ester (XXIX) which is reduced to the β-hydroxy ester (XXX) wherein the hydroxy group is protected as acetal ether; the obtained compound (XXXI) is then submitted, in a conventional manner, to the hydroboration at the olefinic double bond to give the alcohols (XXXIIa) and (XXXIIIa) which are then resolved by chromatography or by fractionate crystallization, converted into the corresponding silyl ethers (XXXIIb) and (XXXIIIb) and finally transformed into the compounds of formula (XI) by reduction with diisobutylaluminium hydride in toluene according to known methods.

The compounds of formula (I) show the same pharmacological activities as the natural prostacyclin, or PGI$_2$ but, as compared with PGI$_2$, the compounds covered by this invention have a particular advantage in their greater stability in the range of pH between zero and 11, in particular, at physiologic pH: this leads to longer lasting and more constant biological activity. The source of this greater stability is the different chemical structure of these compounds as compared to natural prostacyclin. Since there is an oxygen heteroatom in the 2-oxa-bicyclo[3.3.0]octane system, natural prostacyclin is an exocyclic enol ether and so is extremely acid sensitive. The product of reaction with acid, 6-keto-PGF$_{1\alpha}$, shows almost none of the biological activity characteristic of natural prostacyclin. On the other hand, the compounds covered by this invention have no oxygen in the bicyclic system and so are not enol ethers. Since they are not highly labile as are the natural derivatives, they may be administered by mouth.

In addition, compounds of formula (I) in which there is a triple bond in the 13-14 position of the ω-chain or in which there is a hindering group, such as a C$_1$-C$_6$-alkyl group or an electron receptor group, e.g. fluorine, near the hydroxyl in position 15 (R$_3$ or R$_4$=hydroxy) are more resistant to enzyme-induced (for instance, 15-PG-dehydrogenase) metabolic degradation than natural prostacyclin.

The pharmacological actions of natural prostacyclin are known. Thus, for example, when inhaled in asthmatic patients, prostacyclin prevents aspecifically induced (e.g. by nebulized water or by effort) bronchocostriction [S. Bianco et al, J. Res. Medical Science, 6, 256 (1978)]; when infused in man, it shows hypotensive and vasodilator activity and also shows blood platelet anti-aggregant and disaggregant properties [Szekely et al, Pharm. Res. Comm. 10, 545 (1978)]; prostacyclin also possess uterus stimulant action in the monkey and in woman; furthermore, prostacyclin exhibits luteolytic activity in test animals and is able to protect the gastric mucous membrane from ulcers induced by non-steroidal anti-inflammatory substances, e.g. acetyl salicylic acid (ASA) and indomethacin, in test animals, e.g. the rat.

In natural prostacyclin these activities are combined with a marked chemical instability which is unsuitable for pharmaceutical use. As already reported, the compounds of formula (I) have pharmacological actions similar to those of natural prostacyclin but the undesired chemical instability of PGI$_2$, is absent in the compounds of the invention.

The following Table shows the in vitro inhibitory effect on platelet aggregation induced by 10 μM ADP in platelet rich plasma and the hypotensive effect on the anaesthetized rat of two compounds of the invention and PGI$_2$.

|     | in vitro antiaggregant effect IC$_{50}$ηg/ml | hypotensive effect potency ratio |
| --- | --- | --- |
| (1) | 1   | 100 |
| (2) | 25  | 1.15 |
| (3) | 20  | 0.25 |

(1) PGI$_2$
(2) 5t,13t-11α,15S-dihydroxy-9a-deoxy-9a-methylene-prostacycla-5,13-dienoic acid
(3) 5t,13t-11α,15S-dihydroxy-9a-deoxy-9a,7a-homo-dimethylene-prostacycla-5,13-dienoic acid.
IC$_{50}$ = 50% platelet aggregation inhibiting concentration.

A comparison between PGI$_2$ and the compound dl-5,13t-11α,15S-dihydroxy-9a-deoxy-7-nor-methylene-prostacycla-5,13-dienoic acid shows that, for equiactive antiaggregant doses, the antiulcerogenic activity of the latter is ten times greater than that of PGI$_2$.

Again in comparison with PGI$_2$, for equally active antiaggregant doses, the in vitro luteolytic activity in the hamster is 5 and respectively, 8 times greater for dl-5,13t-11α,15S-dihydroxy-9a-deoxy-9a,9b-dimethylene-17-cyclohexyl-18,19,20-trinor-prostacycla-5,13-dienoic acid, and for 5c,13t-11α,15S-dihydroxy-9a-deoxy-9a,7a-homo-dimethylene-16-phenoxy-17,18,19,20-tetranor,prostacycla-5,13-dienoic acid.

As to their prostacyclin- and prostaglandin-like activity the compounds covered by this invention may be used in human and veterinary medicine when natural prostacyclin and prostaglandins are indicated therapeutically.

For instance, these compounds are useful in treating asthma because of their pronounced bronchodilatory effect. In this application, they may be administered by various routes: orally in tablets, capsules, pills, or liquids like drops or syrups; rectally, in suppositories, intravenously, intramuscularly or subcutaneously; by inhalation as aerosols or vaporizer solutions; or by insufflation as powders. Doses of approximately 0.01-4 mg/kg may be given from 1 to 4 times daily, but the exact dose depends on the age, weight and condition of the patient as well as the administration method.

For anti-asthmatic applications the compounds covered by this invention may be combined with other anti-ashmatics: simpaticomimetics like isoproterenol, ephedrine, etc.; xanthine derivatives like theophillin and aminophillin; and corticosteroids like prednisolone and ACTH.

In addition the compounds covered by this invention exhibit oxytocic activity and so may be used in place of oxytocin to induce labor or expel a dead fetus, both in human and veterinary obstetrics. For this application, the compounds are given intravenously at a dose of approximately 0.01 g/kg/minute until the end of labor, or by mouth.

The compounds covered by this invention are also luteolytic and so are useful in fertility control, with the advantage that they stimulate the smooth muscles much less and so are free of the side effects of natural prostaglandins like vomiting and diarrhea.

Further, these compounds are anti-ulcerogenic and thus may be used to reduce and control excessive gastric secretion in mammals. In this way they minimize or eliminate the formation of gastrointestinal ulcers and accelerate the cure of any ulcers already present in the gastrointestinal tract. They are administered in this case by intravenous infusion or by intravenous, subcutaneous or intramuscular injection; doses for intravenous infusion range from 0.1 μg to 500 μg/kilo/minute. The total daily dose for both injection and infusion is on the order of 0.1-20 mg/kg depending on the age, weight and condition of the patient or animal and on the administration method.

However, like natural prostacyclines, the most important pharmacological property of the compounds covered by this invention is their platelet anti-aggregant activity, that is, the capacity to inhibit platelet aggregation, to decrease adhesion, to prevent clot formation and to dissolve recently-formed clots. This platelet anti-aggregant activity is also associated with a relaxing of the coronary arteries. For these reasons, these compounds are useful in preventing and treating myocardial infarctions and, in general, in treating and preventing thromboses, in treating conditions like atherosclerosis, arteriosclerosis and, more generally, dihyperlipidemia.

Normal administration methods are used in this application: that is, intravenous, subcutaneous, intramuscular, etc. In emergency situations intravenous administration is preferred, in doses ranging from 0.005 to 20 mg/kg/day, again depending on the age, weight and condition of the patient and on the administration method. As mentioned above, the compounds covered by this invention are useful in human and veterinary therapy, with several administration methods. They may be given orally in tablets, capsules, drops or syrups; rectally in suppositories; parenterally, in solutions or suspensions gives subcutaneously or intramuscularly; intravenously, as preferred in emergencies; by inhalation in aerosols or vaporizer solutions; in sterile grafts for prolonged action; or endovaginally, for instance in vaginal suppositories.

Pharmaceutical and veterinary compositions of the compounds covered by this invention may be prepared conventionally using common carriers and/or diluents. For example, sterile and isotonic aqueous solutions are preferred for intravenous injection or infusion. Sterile aqueous solutions or suspensions in aqueous or nonaqueous medium are used for subcutaneous or intramuscular injections. A sterile compress or a silicon rubber capsule containing or impregnated with the active ingredient may be used for sterile grafts.

Conventional carriers and diluents include water, gelatine, lactose, dextrose, sucrose, mannitol, sorbitol, cellulose, talc, stearic acid, calcium and magnesium stearate, glycols, starch, gum arabic, gum adragant, alginic acid, alginates, lecithin, polysorbates, vegetables oils, etc.

The compounds may be given with a vaporizer using an aqueous suspension or solution of them, preferably in their salt forms, for instance the sodium salt. Or the compounds may be suspended or dissolved in one of the common liquified propellants like dichlorodifluoromethane or dichlorotetrafluoroethane and given with a pressurized container like an aerosol bomb. When the compound is not soluble in the propellant, a co-solvent must be added to the pharmaceutical formulation: for instance, ethanol, dipropyleneglycol and/or a tensioactive substance.

In the following examples, THP, DMtB, DIOX, THF, DMSO, DIBA and DMF refer respectively to tetrahydropyranyl, dimethyl-tert-butyl, 1,4-diox-2-enyl, tetrahydrofuran, dimethylsulphoxide, diisobutylaluminiumhydride and dimethylformamide.

The following examples illustrate but do not in any way limit the present invention.

EXAMPLE 1

1.1 g of sodium borohydride (0.029 mol) is added with stirring to a solution of 11.6 g of bicyclo[3.3.0]octane-3,7-dione ($8.4 \times 10^{-2}$ mol) in 100 ml of methylene chloride and 100 ml of ethanol. After 45 minutes at this temperature, the excess reagent is decomposed by slowly adding 20 ml of acetone. The mixture is then neutralized with 1.4 ml of acetic acid, and evaporated under vacuum to afford a residue which is taken up in water and methylene chloride. The organic phase is evaporated to dryness and filtered on silica gel (70:30 hexane:ethyl ether as eluent) to afford 9.1 g of 7ξ-hydroxy-bicyclo[3.3.0]octan-3-one.

A solution of this compound (0.065 mol) in 27 ml of anhydrous dimethylformamide is treated with 12.8 g of dimethyl-tert-butylsilyl chloride and 8.85 g of imidazole. The resulting mixture is heated to 60° C. for 5 hours, cooled, diluted with two volumes of water and extracted with ethyl ether ($3 \times 40$ ml and $2 \times 20$ ml). The combined organic extract is washed with 5% NaHCO$_3$ and then water until neutral, and evaporate to dryness to give 15.8 g of crude product (95% yield). Purification on silica gel affords 2.85 g of 7-exo-hydroxy-bicyclo[3.3.0]octan-3-one-dimethyl-tert-butylsilyl ether and 11.8 g of 7-endo-hydroxy-bicyclo[3.3.0]octan-3-one-7-dimethyl-tert-butylsilyl ether.

A solution of the latter (11.8 g, $4.63 \times 10^{-2}$ mol) in 295 ml of methyl carbonate (Me$_2$CO$_3$) is stirred with the exclusion of water in an inert atmosphere and treated cautiously with 6.95 g of 80% sodium hydride. When hydrogen evolution ceases, the reaction mixture is heated at 75°-80° C. for forty minutes. After cooling, the mixture is diluted with two volumes of ethyl ether and cautiously treated with 13 g of glacial acetic acid. The organic phase is then separated with pH 5.2-5.5 buffer and the aqueous layer is extracted with ethyl ether. The combined organic extract is dried over Na$_2$SO$_4$ and evaporated to dryness to give 12.82 g of d,l-7-endo-hdyroxy-bicyclo[3.3.0]octan-3-one-2-carboxymethylester-7-dimethyl-tert-butylsilyl ether (85% of the 14.49 g theoretical yield), which after purification on silica gel (45 g/g, with 97:3 hexane:ethyl ether as eluent) affords 10.81 g of the pure product; $\lambda_{max}=254$ m$\mu$,$\epsilon=7,000$.

Starting with the exo isomer, the same procedure affords d,l-7-exo-hydroxy-bicyclo[3.3.0]octan-3-one-2-carboxymethylester-7-dimethyl-tert-butyl silylether; $\lambda_{max}=254$ m$\mu$, $\epsilon=6,500$.

EXAMPLE 2

A solution of 7.5 g of d,l-7-endo-hydroxy-bicyclo[3.3.0]octan-3-one-2-carboxymethylester-7-dimethyl-tert-butyl silylether (DMtB-silylether) in 75 ml of dichloromethane and 75 ml of ethanol is cooled to $-20°$ C. and treated with stirring with 0.9 g of sodium borohydride. After stirring for 15 minutes, the excess reagent is destroyed by adding 12 ml of acetone. The mixture is brought to 0° C., 20 ml of 20% KH$_2$PO$_4$ is added, the solvent is evaporated under vacuum and the residue is extracted several times with ethyl ether. The combined organic extract is washed with 5 ml of water and evaporated to dryness to afford a residue which is crystallized from n-hexane to give 4.8 g of d,l-3,7-endo-dihydroxy-bicyclo[3.3.0]octane-2-exo-carboxymethylester-7-DMtB-silylether, m.p.$=68°-70°$ C. The mother liquor is adsorbed on 25 g of silica gel; elution with 90:10 n-heptane:ethyl ether gives another 2 g of product pure enough to be used as is.

A solution of 6 g of d,l-3,7-endo-dihydroxy-bicyclo[3.3.0]octane-2-exo-carboxymethylester-7-DMtB-silylether in 100 ml of 80:20 methanol:water is treated with 2 g of potassium hydroxide and heated to reflux for 30 minutes. After concentration under vacuum, the mixture is acidified to pH 5.1 and extracted with ethyl acetate. Evaporation of the organic layer gives 5.1 g of d,l-3,7-endo-dihydroxy-2-carboxy-bicyclo[3.3.0]octane-7-DMtB-silylether. A solution of this compound in 150 ml of acetonitrile is then treated with 2.81 g of d-(+)-ephedrine. 4 hours at room temperature afford 2.9 g of a salt which is crystallized twice from acetonitrile to give 1.85 g of (+)-3,7-endo-dihydroxy-2-exo-carboxy-bicyclo[3.3.0]octane-7-DMtB-silylether-d(+)-ephedrine salt. All the mother liquors are collected and evaporated to dryness to give a residue which is dissolved in water and treated with 0.68 g of sodium hydroxide in water. The d-(+)-ephedrine is recovered in a benzene extraction, and the sodium salt solution is acidified to pH 5 and extracted with ethyl acetate. The organic phase is evaporated to dryness to give a residue which is treated with 2.2 g of l-ephedrine to afford after several crystallizations 2.3 g of (−)-3,7-endo-dihydroxy-2-exo-carboxy-bicyclo[3.3.0]octane-7-DMtB-silylether-1-ephedrine salt.

EXAMPLE 3

A solution of 6.28 g of d,l-3,7-endo-dihydroxy-bicyclo[3.3.0]octane-7-DMtB-silylether-2-exo-carboxymethylester in 30 ml of anhydrous methylene chloride is treated with 2.19 g of 2,3-dihydropyran and 39 mg of p-toluenesulfonic acid. After 3 hours at room temperature, the reaction mixture is washed with 5% NaHCO$_3$ (2×5 ml). Evaporation of the organic phase to dryness gives 8 g of d,l-3,7-endo-dihydroxy-bicyclo-[3.3.0]octane-7-DMtB-silylether-3-THP-ether-2-carboxymethyl ester, which is then dried by being taken up in anhydrous benzene (2×15 ml) and evaporated to dryness. This product in 30 ml of anhydrous ethyl ether is added dropwise, in 15 minutes, to a stirred suspension of 0.6 g of LiAlH$_4$ in 40 ml of anhydrous ethyl ether. Stirring is continued for 30 minutes before the excess reagent is destroyed by the cautious addition of 5 ml of acetone followed by water-saturated ethyl ether. 10 g of anhydrous sodium sulfate is then added. Filtration of the organic solution and evaporation to dryness afford 7.2 g of d,l-3,7-endo-dihydroxy-2-exo-hydroxymethyl-bicyclo[3.3.0]octane-7-DMtB-silylether-3-THP-ether.

The following compounds are prepared in this way from optically active starting materials:

nat-3,7-endo-dihydroxy-2-exo-hydroxymethyl-bicyclo[3.3.0]octane-7-DMtB-silylether-3-THP-ether;
ent-3,7-endo-dihydroxy-2-exo-dihydroxymethyl-bicyclo[3.3.0]octane-7-DMtB-silylether-3-THP-ether.

If 1,4-diox-2-ene is used instead of 2,3-dihydropyran, the corresponding 3(2'-DIOX)-ethers are obtained.

EXAMPLE 4

A solution of 3.8 g of d,l-3,7-endo-dihydroxy-bicyclo-[3.3.0]octane-2-exo-carboxymethylester-7-DMtB-silylether in 40 ml of benzene is treated first with 3.66 g of benzoic acid and 7.9 g of triphenylphosphine, and then, with stirring, with 5.30 g of ethyl azo-bis-carboxylate in 15 ml of benzene. After 40 minutes of stirring, the organic phase is washed with 2 N sulfuric (2×20 ml), and then sodium carbonate (3×15 ml) and finally water until neutral. Evaporation to dryness affords a mixture of d,l-3-exo-7-endo-dihydroxy-bicyclo[3.3.0]octane-2-exo-carboxymethylester-7-DMtB-silylether-3-benzoate and d,l-7-endo-hydroxy-bicyclo[3.3.0]oct-3-ene-2-exo-carboxymethylester-7-DMtB-silylether.

The crude reaction product is dissolved in anhydrous methanol, stirred for 3 hours, and treated with 0.5 g of anhydrous potassium carbonate. Evaporation to dryness affords a residue which is taken up in ethyl acetate and saturated KH$_2$PO$_4$. The organic phase is washed until neutral and evaporated to dryness. The residue is adsorbed on silica gel and eluted with hexane and hexane:ethyl ether to give:

(a) 1.01 g of d,l-7-endo-hydroxy-bicyclo[3.3.0]oct-3-ene-2-carboxymethylester-7-DMtB-silylether, which is dissolved in methanol, treated with 0.3 g of 5% Pd on CaCO$_3$ and hydrogenated at room temperature and pressure to give d,l-7-endo-hydroxy-bicyclo[3.3.0]octane-2-carboxymethylester-7-DMtB-silylether;

(b) 2.01 q of d,l-3-exo-7-endo-dihydroxy-bicyclo[3.3.0]octane-2-carboxymethylester-7-DMtB-silylether, which is saponified as described in Example 2 with 5% potassium carbonate in 80:20 methanol:water to give d,l-3-exo-7-endo-dihydroxy-bicyclo[3.3.0]octane-2-exo-carboxy acid-7-DMtB-silylether. This is then separated into individual optical antipodes with (+) and (−) amphetamine.

Reaction with ethereal diazomethane converts (+)-3-exo-7-endo-dihydroxy-bicyclo[3.3.0]octane-2-exo-carboxy acid-7-DMtB-silylether into the methyl ester derivative. Subsequent reaction with 2,3-dihydropyran followed by reduction with LiAlH$_4$ in ethyl ether gives (+)-3-exo-7-endo-2-exo-hydroxymethyl-bicyclo[3.3.0]octane-3-THP-ether-7-DMtB-silylether.

The (−) enantiomers and the racemic mixture are prepared analogously.

EXAMPLE 5

5 g of d,l-7-endo-hydroxy-bicyclo[3.3.0]octane-DMtB-silylether-3-exo-carboxymethylester in 100 ml of aqueous methanol is saponified with 2 g of KOH, at reflux. After the methanol is removed under vacuum, the aqueous solution of the potassium salt is extracted to remove neutral impurities, acidified, and extracted with ethyl ether. The latter extracts are combined and evaporated to dryness to give 4.5 g of the d,l acid which is then separated into optical antipodes with (+) and (−) ephedrine.

1.32 g of (−)-7-endo-hydroxy-bicyclo[3.3.0]octane-7-DMtB-silylether-2-exo-carboxy acid is then dissolved in 20 ml of THF and treated with 10 ml of 1 M BH$_3$ in THF. After 4 hours at room temperature, the excess reagent is destroyed by the cautious addition of 20 ml of 1.5 N NaOH. The THF is then removed under vacuum and the aqueous phase is extracted with ethyl ether. The combined organic extract is washed until neutral and evaporated to dryness to afford 1.02 g of (−)-7-endo-hydroxy-2-exo-hydroxymethyl-bicyclo[3.3.0]octane-7-DMtB-silylether.

The (+) isomer and the racemic mixture are prepared analogously.

EXAMPLE 6

2.7 g of d,l-7-endo-hydroxy-2-exo-hydroxymethyl-bicyclo-[3.3.0]octane-7-DMtB-silylether in 20 ml of methylene chloride is treated with 0.95 g of 2,3-dihydropyran and 20 mg of p-toluenesulfonic acid for 3 hours at room temperature. After being washed with 7% aqueous NaHCO$_3$ and then water, the organic phase is evaporated to dryness to give crude d,l-7-endo-hydroxy-2-exo-tetrahydropyranyloxymethyl-bicyclo[3.3.0]octane-7-DMtB-silylether. This is dissolved in 15 ml of THF and treated with 4.5 g tetrabutylammonium fluoride for 10 hours, with stirring. The reaction mixture is then concentrated under vacuum, adsorbed on silica gel and eluted with benzene:ethyl ether to give 2.1 g of d,l-7-endo-hydroxy-2-exo-THP-oxymethyl-bicyclo-[3.3.0]octane. A solution of this product is 25 ml of acetone is cooled to −20° C.-8° C. with stirring and treated with 4.2 ml of 8% Jones' reagent (CrO$_3$ in aqueous sulfuric acid) over a period of 15 minutes, until a slight pink color persists. After an additional 14-20 minutes of stirring, 1.5 ml of isopropanol is added dropwise and the resulting green solution is diluted with 6 volumes of benzene. The organic phase is washed with 20% $(NH_4)_2SO_4$ until neutral, and the combined aqueous phase is re-extracted with benzene. The combined benzene extract is dried and evaporated to dryness to afford 1.82 g of d,l-2-exo-THP-oxymethyl-bicyclo[3.3.0]octan-7-one.

The nat- and enant- isomers are prepared analogously.

EXAMPLE 7

With external cooling and stirring to keep the reaction temperature near 20°-22° C., a solution of 6.57 g of potassium tert-butylate in 65 ml of DMSO is added dropwise to 6.76 g of 4-carboxybutyl-triphenyl-phosphonium bromide in 40 ml of DMSO. After the addition, the mixture is diluted with an equal volume of water acidified to pH 5 and extracted with ethyl ether. The aqueous phases are discarded, and the combined organic extract is re-extracted several times with 0.5 N NaOH. The alkaline aqueous phases are acidified to pH5 and re-extracted with 50:50 ethyl ether-pentane. This combined organic extract is brought to small volume, treated with ethereal diazomethane until a yellow coloration persists, and then evaporated to dryness. The residue is then dissolved in 50 ml of acetone, treated with 20 ml of 2 N aqueous oxalic acid, and held at 40°–45° C. for 8 hours. After the acetone is removed under vacuum, the aqueous phase is extracted with ethyl acetate, and the combined organic extract is evaporated to dryness. Purification of the resulting residue on silica gel with ethyl ether as eluent gives a mixture of d,l-5-cis,trans-[2'-exo-hydroxymethyl-bicyclo[3.3.0]oct-7'-enyl]-pentenoic acid methyl ester (1.75 g). The individual isomers may be separated with high pressure liquid-liquid chromatography to the 5-trans-d,l and the 5-cis-d,l isomers; the latter is named 5-cis-ω(20→12)-octanor-12-hydroxymethyl-9a-deoxy-9a-methylene-prostacycl-5-enoic acid methyl ester.

If the 4-carboxybutyl-triphenylphosphonium bromide in the above procedure is replaced by one of the following Wittig reagents (3-carboxypropyltriphenylphosphonium bromide, 5-carboxypentyltriphenylphosphonium bromide, 4-carboxy-2-oxa-butyltriphenylphosphonium bromide), the methyl esters of the following acids are prepared:

d,l-5-cis-ω(20→12)-octanor-2 nor-12β-hydroxymethyl-9a-deoxy-9a-methylene-prostacycl-5-enoic acid;

d,l-5-cis-ω(20→12)-octanor-2ahomo-12β-hydroxymethyl-9a-deoxy-9a-methylene-prostacycl-5-enoic acid;

d,l-5-cis-ω(20→12)-octanor-3-oxa-12β-hydroxymethyl-9a-deoxy-9a-methylene-prostacycl-5-enoic acid;

as well as their 5-trans isomers and the individual nat- and enant- antipodes.

EXAMPLE 8

A stirred solution of 7.16 g of 5-cis-ω(20→12)-octanor-12β-hydroxymethyl-9a-deoxy-9a-methylene-prostacycl-5-enoic acid methyl ester in 80 ml of 75:25 benzene:dimethylsulfoxide is treated with 8.9 g of dicyclohexylcarbodiimide and then with 14.2 ml of a pyridinium trifluoroacetate solution (prepared by adding 25 ml of 75:25 benzene:DMSO to 1 ml of trifluoroacetic acid and 2 ml of pyridine). After four hours of stirring, the reaction mixture is diluted with 100 ml of benzene and 3 g of oxalic acid in water is added dropwise. The dicyclohexylurea is removed by filtration, the organic phase is separated and washed with water (5×6 ml). Reduction in volume gives a benzene solution of the 12β-formyl derivative which is added all at once to a solution of (2-oxo-heptyl)dimethyl phosphonate sodium salt. The latter is prepared by adding dropwise 7.58 g of (2-oxo-heptyl)-dimethyl phosphonate in 40 ml of anhydrous benzene to a stirred solution of 1.02 g of sodium hydride (80% mineral oil dispersion) in an inert gas atmosphere, continuing stirring until $H_2$ evolution ceases. After the addition of the formyl derivative to this sodium phosphonate salt, stirring is continued for 20 minutes. The reaction mixture is then neutralized with saturated monosodium phosphate solution. The organic phase is separated, reduced to small volume, adsorbed on silica gel and eluted with cyclohexane: ethyl ether to give 6.4 g of 5-cis-13-trans-9a-deoxy-9a-methylene-15-oxo-prostacycla-5,13-dienoic acid methyl ester.

Using an analogous 12β-hydroxymethyl derivative from example 7 gives the methyl esters of the following acids:

5-cis-13-trans-9a-deoxy-9a-methylene-15-oxo-2-nor-prostacycla-5,13-dienoic acid;

5-cis-13-trans-9a-deoxy-9a-methylene-15-oxo-2ahomo-prostacycla-5,13-dienoic acid;

5-cis-13-trans-9a-deoxy-9a-methylene-15-oxo-3-oxa-prostacycla-5,13-dienoic acid;

as well as their 5-trans geometric isomers, in the nat-, enant- and d,l forms.

EXAMPLE 9

A stirred and cooled (5°-8° C.) solution of 1.35 g of 2-exo-hydroxymethyl-7-endo-hydroxy-bicyclo[3.3.0]octane-DMtB-silylether in 5 ml of pyridine is treated with 0.82 g of benzoyl chloride. After 8 hours at room temperature, 2 N $H_2SO_4$ is added and the mixture is extracted with ethyl ether to give 2-exo-benzoyloxymethyl-7-endo-hydroxy-bicyclo[3.3.0]octane-7-DMtB-silylether. This silylether group is removed by reflux in 20 ml of acetone with 8 ml of 2 N oxalic acid. The acetone is removed under vacuum and the residue is extracted with ethyl ether to afford, after purification on silica gel, 1.11 g of 2-exo-benzoyloxymethyl-7-endo-hydroxy-bicyclo[3.3.0]-octane. This is dissolved in pyridine and then added to a solution of 1 g of $CrO_3$ in 10 ml of pyridine. After 6 hours at room temperature, this mixture is diluted with 20 ml of benzene and filtered. The filtrate is evaporated under vacuum and the residue is taken up in 2 N sulfuric acid and benzene. After being washed with 2 N $H_2SO_4$ and water until neutral, the organic extract is evaporated to dryness to afford 0.98 g of 2-exo-benzoyloxymethyl-bicyclo[3.3.0]octan-7-one. A solution of this compound in 5 ml of anhydrous THF is then added to a solution of (2-oxo-5-trimethoxy-pentyl)-dimethyl phosphonate sodium salt, prepared by adding dropwise a suspension of 0.23 g of 80% sodium hydride in THF to a solution of 2.12 g of (2-oxo-5-trimethoxy-pentyl)-dimethyl phosphonate in 6 ml of anhydrous THF. After 10 hours of stirring, the mixture is neutralized with 15% $KH_2PO_4$, the THF is evaporated under vacuum and the residue is extravted with ethyl ether. The combined extract is concentrated in volume, adsorbed on silica gel and eluted with hexane:ether to afford 1.1 g of 2'-benzoyloxymethyl-bicyclo[3.3.0]oct-7-enyl-1,1,1-trimethoxy-pent-5-en-4-one, or 12β-benzoyloxymethyl-ω(20→12)-octanor-4-oxo-9a-deoxy-9a-methylene-prostacycl-5-enoic acid-orthomethylester, as a mixture of the 5-cis and 5-trans olefins which are then separated by high pressure liquid-liquid chromatography.

Subsequent treatment with aqueous methanol and H$_2$SO$_4$ gives the corresponding methyl ester derivatives. Reaction of 0.3 g of methyl ester with 0.25 ml of 1,3-ethanedithiol in methylene chloride and a catalytic amount of BF$_3$-etherate for 15 minutes at 0° C. then affords 12β-benzoyloxymethyl-ω(20→12)-octanor-4,4-ethylenedithio-9a-deoxy-9a-methylene-prostacycl-5-enoic acid methyl ester.

EXAMPLE 10

0.8 g of 12β-benzoyloxymethyl-ω(20→12)-octanor-4-oxo-9a-deoxy-9a-methylene-prostacycl-5-enoic acid methyl ester in 10 ml of methanol is selectively de-benzoylated upon treatment with stirring with 0.15 g of anhydrous K$_2$CO$_3$. After the solvent is evaporated, the residue is taken up in 15% aqueous KH$_2$PO$_4$ and methylene chloride to afford upon evaporation of the organic phase 12β-hydroxymethyl-ω(20→12)-octanor-4-oxo-9a-deoxy-9a-methylene-prostacycl-5-enoic acid methylester. A solution of this compound in 10 ml of CH$_2$Cl$_2$ and 10 ml of ethanol cooled to −20° C. is treated with 90 mg of NaBH$_4$ and stirred for two hours. Excess reagent is then destroyed with 15% aqueous acetic acid, the solvent is evaporated and the residue is adsorbed on silica gel. Elution with ethyl ether affords 0.21 g of 12β-hydroxymethyl-ω(20→12)-octanor-4S-hydroxy-9a-deoxy-9a-methylene-prostacycl-5-enoic acid methyl ester and 0.13 g of the 4R-hydroxy isomer.

The individual products are then saponified with 20% aqueous methanol and 19% potassium carbonate to afford, after acidification and extraction with ethyl acetate, 0.18 g of 12β-hydroxymethyl-ω(20→12)-octanor-4S-hydroxy-9a-deoxy-9a-methylene-prostacycl-5-enoic acid-1,4-γ-lactone and 0.11 g of the 4R isomer. Oxidation of these following the procedure in example 8 gives the 12-formyl derivatives.

EXAMPLE 11

0.28 g of 4,4-ethylenetithio-12β-benzoyloxymethyl-ω(20→12)-octanor-9a-deoxy-9a-methylene-prostacycl-5-enoic acid methyl ester is selectively de-benzoylated upon methanolysis with K$_2$CO$_3$ in anhydrous methanol to give the corresponding 12β-hydroxymethyl derivative. This is then oxidized to the aldehyde according to the procedure in example 8 to give the 12β-formyl derivative.

Reaction of 0.12 g of this compound is benzene with the phosphonate prepared from 0.177 g of (2-oxo-3,3-dimethylheptyl)-dimethyl phosphonate and 20 mg of 80% NaH, as described in example 8, gives 5,13t-16,16-dimethyl-4,4-dithioethylenedioxy-15-oxo-9a-deoxy-9a-methylene-prostacycla-5,13-dienoic acid methylester.

In an analogous fashion, using (4-cyclohexyl-2-oxobutyl)-dimethyl phosphonate as the phosphonate and the 4S-lactone from example 10 as the aldehyde affords 5,13t-4S-hydroxy-15-oxo-9a-deoxy-9a-methylene-17-cyclohexyl-18,19,20-trinor-prostacycla-5,13-dienoic acid-1,4-γ-lactone. Or, with (3-phenoxy-2-oxo-propyl)-dimethyl phosphonate, 5,13t-4S-hydroxy-15-oxo-9a-deoxy-9a-methylene-17,18,19,20-tetranor-16-phenoxy-prostacycla-5,13-dienoic acid-1,4-γ-lactone is prepared.

EXAMPLE 12

Using (2-oxo-3S-methyl-heptyl)-dimethyl phosphonate and (2-oxo-3S-fluoro-heptyl)-dimethyl phosphonate as the phosphonates and 12β-formyl-ω(20→12)-octanor-4R-hydroxy-9a-deoxy-9a-methylene-prostacycl-5-enoic acid-1,4-γ-lactone as the aldehyde, the procedures of examples 8 and 11 afford:

5,13t-4R-hydroxy-15-oxo-9a-deoxy-9a-methylene-16S-methylprostacycla-5,13-dienoic acid-1,4-γ-lactone;

5,13t-4R-hydroxy-15-oxo-9a-deoxy-9a-methylene-16S-fluoroprostacycla-5,13-dienoic acid-1,4-γ-lactone.

EXAMPLE 13

A solution of 0.7 g of 5c, 13t-15-oxo-9a-deoxy-9a-methylene-prostacycla-5,13-dineoic acid methyl ester in 7 ml of methylene chloride and 7 ml of ethanol cooled to −20° C. is treated with 38 mg of sodium borohydride. After 20 minutes of stirring, the reaction is quenched with 2 ml of acetone and 2.5 ml of 20% aqueous NaH$_2$PO$_4$. The mixture is then reduced in volume under vacuum and extracted with methylene chloride. The combined organic extract is evaporated to dryness to give a residue which is purified on silica gel with ethyl ether as eluent to afford 0.32 g of 5c, 13t-15S-hydroxy-9a-deoxy-9a-methylene-protascycla-5,13-dienoic acid methylester and 0.26 g of the 15R isomer.

This same procedure for reducing the 15-oxo derivatives from examples 8, 11 and 12 affords the methyl esters of the following acids:

5cis,13-trans-9a-deoxy-9a-methylene-15S-hydroxy-2-nor-prostacycla-5,13-dienoic acid;

5cis,13trans-9a-deoxy-9a-methylene-15S-hydroxy-2ahomo-prostacycla-5,13-dienoic acid;

5cis,13trans-9a-deoxy-9a-methylene-15S-hydroxy-3-oxa-prostacycla-5,13-dienoic acid;

5cis,13trans-9a-deoxy-9a-methylene-4,4-diethioethylenedioxy-15S-hydroxy-prostacycla-5,13-dienoic acid;

and the 1,4-lactones of the following acids:

5c,13t-9a-deoxy-9a-methylene-4S,15S-dihydroxy-17-cyclohexyl-18,19,20-ω-trinor-prostacycla-5,13-dienoic acid;

5c,13t-9a-deoxy-9a-methylene-4S,15S-dihydroxy-16-phenoxy-17,18,19,20-ω-tetranor-prostacycla-5,13-dienoic acid;

5c,13t-9a-deoxy-9a-methylene-4R,15S-dihydroxy-16S-methylprostacycla-5,13-dienoic acid;

5 13t-9a-deoxy-9a-methylene-4R,15S-dihydroxy-16S-fluoroprostacycla-5,13-dienoic acid;

as well as their 5-trans geometric isomers, in the nat-, enant- and d,l forms.

EXAMPLE 14

A solution of 0.35 g of 5c,13t-15-oxo-9a-deoxy-9a-methylene-prostacycla-5,13-dienoic acid methylester in 10 ml of 2:1 ethyl ether:toluene is cooled to 31 30° C. and treated with stirring with 5 ml of 5% methyl magnesium iodide in ethyl ether. After 4 hours of stirring, the mixture is brought to 0° C. and quenched with 20% aqueous ammonium chloride. The organic phase is washed with water, sodium bicarbonate and water, dried over MgSO$_4$, treated with 0.1 ml of pyridine, and evaporated under vacuum to give a mixture of the 15S and 15R alcohols. Separation on silica gel with 80:20 ethyl ether:isopropyl ether as eluent affords 0.1 g of 5c,13t-15S-hydroxy-9a-deoxy-9a-methylene-prostacycla-5,13-dienoic acid methylester and 0.1 g of the 15R isomer.

EXAMPLE 15

With the same substrate but anhydrous THF as solvent, reaction with 8 ml of 0.3 M ethynyl magnesium bromide in THF gives, after chromatography on silica gel, 5c,13t-15-ethynyl-15S-hydroxy-9a-deoxy-9a-methylene-prostacycla-5,13-dienoic acid methylester and its 15R isomer.

With 0.3 M vinyl magnesium bromide, 5c,13t-15-vinyl-15S-hydroxy-9a-deoxy-9a-methylene-prostacycla-5,13-dienoic acid methylester and its 15R isomer are prepared.

EXAMPLE 16

A solution of 0.26 g of 5c,13t-9a-deoxy-9a-methylene-4R,15S-dihydroxy-16S-methyl-prostacycla-5,13-dienoic acid-1,4-γ-lactone in methylene chloride is cooled to $-10°--8°$ C. and treated with stirring with 0.3 ml of boron trifluoride etherate ($1.2 \times 10^{-4}$M in anhydrous methylene chloride) and then 5% diazomethane in methylene chloride until a yellow color persists. The solution is washed with 5% aqueous NaHCO$_3$ and then water until neutral, evaporated to dryness, and purified on silica gel (3 g) to give 0.21 g of 5c,13t-9a-deoxy-9a-methylene-4R,15S-dihydroxy-16S-methyl-prostacycla-5,13-dienoic acid-1,4-γ-lactone-15-methylether.

EXAMPLE 17

A solution of 0.74 g of d,l-2-exo-hydroxymethyl-3-exo-THP-oxy-7-endo-DMtB-silyloxy-bicyclo[3.3.0]octane in 15 ml of anhydrous methylene chloride is added all at once to a solution of 3.1 g of Collin's reagent (C$_5$H$_5$N$_2$)$_2$.CrO$_3$ in 40 ml of anhydrous methylene chloride, with stirring and cooling to 0°-5° C. Filtering earth is added after 15 minutes of stirring and the mixture is filtered to give a clear solution of the corresponding d,l-2-exo-formyl derivative. After the solvent is evaporated under vacuum, the residue is taken up in anhydrous benzene and added to a solution of sodium dimethyl-(2-oxo-octyl)-phosphonate. This latter is prepared by adding 0.59 g of (2-oxo-octyl)-dimethyl phosphonate in 10 ml of benzene dropwise to a suspension of 0.07 g of 80% NaH in 20 ml of benzene and stirring the resulting mixture for approximately 1 hour, until hydrogen evolution ceases. Stirring is continued for 20 minutes after the aldehyde is added to the phosphonate carbanion solution. The organic phase is then neutralized with excess 25% aqueous NaH$_2$PO$_4$ and separated. After drying, it is evaporated to dryness to give a residue which is purified on silica gel (cyclohexane:ethyl ether as eluent) to afford 0.81 g of d,l-2-exo-[3'-oxo-non-1'-trans-1'-enyl]-3-exo-THP-oxy-7-endo-DMtB-silyloxy-bicyclo 3.3.0 octane.

EXAMPLE 18

A solution of 1.05 g of d,l-2-exo-hydroxymethyl-3-endo-THP-oxy-7-endo-DMtB-silyloxy-bicyclo[3.3.0]octane in 8 ml of 75:25 benzene:DMSO is treated with 0.89 g of dicyclohexylcarbodiimide and then, with stirring, with 1.42 ml of a pyridinium trifluoroacetate solution. After 3 hours of stirring, 20 ml of benzene are added and excess carbodiimide is quenched with 0.13 g of oxalic acid in 3.8 ml of water. The benzene phase is separated, washed until neutral, and concentrated under vacuum to give a solution of 2-exo-formyl-3-endo-THP-oxy-7-endo-DMtB-silyloxy-bicyclo[3.3.0]octane.

The d,l,-nat- and enantio-formyl derivatives are prepared using this procedure. In the same way, if 7-exo-hydroxybicyclo[3.3.0]octan-3-one-7-dimethyl-tert-butylsilylether is used in the procedures of examples 1, 2 and 3, 2-exo-formyl-3-endo-THP-oxy-7-exo-DMtB-siloxy-bicyclo[3.3.0]octane is obtained.

EXAMPLE 19

A solution of 322 mg of (2-oxo-heptyl)-dimethyl phosphonate in 5 ml of benzene is added to a suspension of 43.5 mg of 80% NaH in 10 ml of benzene, and the resulting mixture is stirred until hydrogen evolution ceases. In the dark, 258 mg of finely divided N-bromosuccinimide are added and stirring is continued for another 5 minutes. 0.37 g of 2-exo-formyl-3-endo-THP-oxy-7-endo-DMtB-silyloxy-bicyclo[3.3.0]octane in 5 ml of benzene is then added and the resulting mixture is stirred for another 15 minutes, after which the reaction mixture is partitioned between benzene and 15% NaH$_2$PO$_4$. The organic phase is dried, concentrated to small volume, adsorbed on silica gel and eluted with 80:20 cyclohexane:ethyl ether to afford 0.42 g of 2-exo-[2'-bromo-3'-oxo-oct-1'-enyl]-3-endo-THP-oxy-7-endo-DMtB-silyloxy-bicyclo[3.3.0]octane ($\lambda_{max}$=251 mµ, $\epsilon$=9,250).

If (2-oxo-3R-fluoro-heptyl)-dimethyl phosphonate is used, the corresponding 2-exo-[2'-bromo-3'-oxo-4'R-fluoro-oct-1'-trans-enyl]-derivative is obtained.

EXAMPLE 20

A solution of 0.3 g of [2-oxo-4(2')-tetrahydrofuryl-butyl]-dimethyl phosphonate is added dropwise to a stirred suspension of 36 mg of 80% sodium hydride in 5 ml of benzene. Stirring is continued until hydrogen evolution ceases, and then a solution of 0.37 g of 2-exo-formyl-3-endo-THP-oxy-7-exo-DMtB-silyloxy-bicyclo[3.3.0]octane is added. After another 20 minutes of stirring, the mixture is taken up in benzene and 20% aqueous monosodium phosphate. The organic phase is separated, concentrated to small volume, adsorbed on silica gel and eluted with benzene:ethyl ether to give 0.35 g of 2-exo-[3'-oxo-5'(2'')-tetrahydrofuryl-pent-1'-transenyl]-3-endo-THP-oxy-7-exo-DMtB-silyloxy-bicyclo[3.3.0]octane ($\lambda_{max}$=229 mµ, $\epsilon$=8,800).

EXAMPLE 21

If 2-exo-formyl-3-endo-THP-oxy-7-endo-DMtB-silyloxybicyclo[3.3.0]octane was the 2-exo-formyl-7-exo-bicyclo derivative used in the procedure described in example 20, and if the following phosphates were used:

(2-oxo-heptyl)-dimethyl phosphonate;
(2-oxo-octyl)-dimethyl phosphonate;
(2-oxo-3S-methyl-heptyl)-dimethyl phosphonate;
(2-oxo-4-cyclohexyl-butyl)-dimethyl phosphonate;
(2-oxo-4-phenyl-butyl)-dimethyl phosphonate;
(2-oxo-3-m-trifluoromethylphenoxy-propyl)-dimethyl phosphonate;
(2-oxo-3-methyl-3-butoxy-butyl)-dimethyl phosphonate;

then the following compounds were prepared:
3-endo-THP-oxy-7-exo-DMtB-silyloxy-2-exo-(3'-oxo-oct-1'-trans-1'-enyl)-bicyclo[3.3.0]octane;
3-endo-THP-oxy-7-exo-DMtB-silyloxy-2-exo-(3'-oxo-non-1'-trans-1'-enyl)bicyclo[3.3.0]octane;
3-endo-THP-oxy-7-exo-DMtB-silyloxy-2-exo-(3'-oxo-4'S-methyloct-1'-trans-1'-enyl)bicyclo[3.3.0]octane;
3-endo-THP-oxy-7-exo-DMtB-silyloxy-2-exo-(3'-oxo-5'-cyclohexyl-pent-1'-trans-1'-enyl)-bicyclo[3.3.0]octane;

3-endo-THP-oxy-7-exo-DMtB-silyloxy-2-exo-(3'-oxo-5'-phenylpent-1'-trans-1'-enyl)-bicyclo[3.3.0]octane;
3-endo-THP-oxy-7-oxo-DMtB-silyloxy-2-exo-(3'-oxo-4'-m-trifluoromethylphenoxy-but-1'-trans-1'-enyl)-bicyclo[3.3.0]octane;
3-endo-THP-oxy-7-exo-DMtB-silyloxy-2-exo-(3'-oxo-4'-methyl-4'-butoxy-pent-1'-trans-1'-enyl)-bicyclo[3.3.0]octane.

EXAMPLE 22

A solution of 0.3 g of d,l-2-exo-(2'-bromo-3'-oxo-4'R-fluoro-oct-1'-trans-1'-enyl)-3-endo-THP-oxy-7-endo-DMtB-silyloxy-bicyclo[3.3.0]octane in 10 ml of anhydrous ether is added dropwise in 15 minutes to a 0.1 M solution of zinc borohydride in ethyl ether (10 ml). After stirring for two hours, the reaction mixture is quenched with saturated sodium chloride and 2 N sulfuric acid. The ether layer is separated and washed with water, 5% NaHCO$_3$, and then water. Evaporation to dryness affords a mixture of the 3'S and 3'R hydroxy alcohols which are separated by liquid-liquid chromatography with isopropyl ether as solvent to give 0.11 g of d,l-2-exo-(2'-bromo-3'S-hydroxy-4'R-fluoro-oct-1'-trans-1'-enyl)3-endo-THP-oxy-7-endo-DMtB-silyloxy-bicyclo 3.3.0 octane and 0.1 g of the 3'R epimer.

EXAMPLE 23

A solution of 0.3 g of 2-exo-[3'-oxo-5'-(2")-tetrahydrofuryl-pent-1'-trans-1'-enyl]-3-endo-THP-oxy-7-exo-DMtB-silyloxy-bicyclo[3.3.0]octane in 3 ml of methylene chloride and 3 ml of ethanol is cooled to −10°−15° C. and then treated with 25 mg of NaBH$_4$. After 30 minutes of stirring, the reaction mixture is quenched with 1.5 ml of acetone and 3 ml of saturated NaH$_2$PO$_4$, evaporated under vacuum, and then extracted with methylene chloride. The organic phase is dried over Na$_2$SO$_4$ and evaporated to dryness to give a residue which is purified on silica gel (hexane:ethyl ether as eluent) to afford 0.1 g of 2-exo[3'S-hydroxy-5'(2")-tetrahydrofuryl-pent-1'-trans-1'-enyl]-3-endo-THP-oxy-7-exo-DMtB-silyloxy-bicyclo[3.3.0]octane and 0.11 g of the 3'R isomer.

EXAMPLE 24

By following the procedure of examples 22 and 23 using one of the α,β-unsaturated ketones prepared as in examples 19, 20 and 21, the following compounds were prepared:
3-endo-THP-oxy-7-endo-DMtB-silyloxy-2-exo-(2'-bromo-3'S-hydroxy-oxt-1'-trans-1'-enyl)-bicyclo[3.3.0]octane;
3-endo-THP-oxy-7-endo-DMtB-silyloxy-2-exo-(3'S-hydroxy-oct-1'-trans-1'-enyl)-bicyclo[3.3.0]octane;
3-endo-THP-oxy-7-endo-DMtB-silyloxy-2-exo-(3'S-hydroxy-4'S-methyl-oct-1'-trans-1'-enyl)-bicyclo[3.3.0]octane;
3-endo-THP-oxy-7-endo-DMtB-silyloxy-2-exo-(3'S-hydroxy-non-1'-trans-1'-enyl)-bicyclo[3.3.0]octane;
3-endo-THP-oxy-7-endo-DMtB-silyloxy-2-exo-(3'S-hydroxy-cyclohexyl-pent-1'-trans-1'-enyl)-bicyclo[3.3.0]octane;
3-endo-THP-oxy-7-endo-DMtB-silyloxy-2-exo-(3'S-hydroxy-5'-phenyl-pent-1'-trans-1'-enyl)-bicyclo[3.3.0]octane;
3-endo-THP-oxy-7-endo-DMtB-silyloxy-2-exo-(3'S-hydroxy-4'-m-trifluoromethylphenoxy-but-1'-trans-1'-enyl)-bicyclo[3.3.0]octane;
3-endo-THP-oxy-7-endo-DMtB-silyloxy-2-exo-(3'hydroxy-4'-methyl-4'-butoxy-pent-1'-trans-1'-enyl)-bicyclo[3.3.0]octane;
3-endo-THP-oxy-7-endo-DMtB-silyloxy-2-exo-(2'-bromo-3'R-hydroxy-oct-1'-trans-1'-enyl)-bicyclo[3.3.0]octane;
3-endo-THP-oxy-7-endo-DMtB-silyloxy-2-exo-(3'R-hydroxy-oct-1'-trans-1'-enyl)-bicyclo[3.3.0]octane;
3-endo-THP-oxy-7-endo-DMtB-silyloxy-2-exo-(3'R-hydroxy-4'S-methyl-oct-1'-trans-1'-enyl)-bicyclo[3.3.0]octane;
3-endo-THP-oxy-7-endo-DMtB-silyloxy-2-exo-(3'R-hydroxy-non-1'-trans-1'-enyl)-bicyclo[3.3.0]octane;
3-endo-THP-oxy-7-endo-DMtB-silyloxy-2-exo-(3'R-hydroxy-5'-cyclohexyl-pent-1'-trans-1'-enyl)-bicyclo[3.3.0]octane;
3-endo-THP-oxy-7-endo-DMtB-silyloxy-2-exo-(3'R-hydroxy-5'-phenyl-pent-1'-trans-1'-enyl)-bicyclo[3.3.0]octane;
3-endo-THP-oxy-7-endo-DMtB-silyloxy-2-exo-(3'R-hydroxy-4'-m-trifluoromethylphenoxy-but-1'-trans-1'-enyl)-bicyclo[3.3.0]octane;
3-endo-THP-oxy-7-endo-DMtB-silyloxy-2-exo-3'4-hydroxy-4'-methyl-4'-butoxy-pent-1'-trans-1'-enyl)-bicyclo[3.3.0]octane.

EXAMPLE 25

A solution of 1.17 g of 2-exo-(3'S-hydroxy-oct-1'-trans-1"-enyl)-3-endo-THP-oxy-7-endo-DMtB-silyloxy-bicyclo[3.3.0]octane in 12 ml of anhydrous methylene chloride is treated with 120 mg of 2,3-dihydropyran and 5 mg of p-toluenesulfonic acid. After 4 hours at room temperature, the organic phase is washed successively with 5% NaHCO$_3$ and water and then evaporated to dryness to give 1.45 g of crude 2-exo-(3'S-THP-oxy-oct-1'-trans-1'-enyl)-3-endo-THP-oxy-7-endo-DMtB-silyloxy-bicyclo[3.3.0]octane. This product is dissolved in 12 ml of THF and treated with 2 g of tetrabutylammonium fluoride. The resulting mixture is stirred for 12 hours at room temperature and concentrated to small volume to give a residue which is purified on silica gel (ethyl ether as eluent) to afford 920 mg of 2-exo-(3'S-hydroxy-oct-1'-trans-1'-enyl)-3-endo-7-endo-dihydroxy-bicyclo[3.3.0]octane-3,3'-bis-THP-ether.

EXAMPLE 26

Using the procedure of example 25 with compounds prepared according to examples 22, 23 and 24, the following bicyclo[3.3.0]octane-3,3'-bis-THP-ether derivatives were prepared:
2-exo-(2'-bromo-3'S-hydroxy-4'-fluoro-oct-1'-trans-1'-enyl)-3-endo-7-endo-dihydroxy;
2-exo-(2'-bromo-3'R-hydroxy-4'R-fluoro-oct-1'-trans-1'-enyl)-3-endo-7-endo-dihydroxy;
2-exo-(3'S-hydroxy-5'(2")-tetrahydrofuryl-pent-1'-trans-1'-enyl)-3-endo-7-exo-dihydroxy;
2-exo-(3'R-hydroxy-5'(2")-tetrahydrofuryl-pent-1'-trans-1'-enyl)-3-endo-7-exo-dihydroxy;
2-exo-(2'-bromo-3'S-hydroxy-oct-1'-trans-1'-enyl)-3-endo-7-endo-dihydroxy;
2-exo-(2'-bromo-3'R-hydroxy-oct-1'-trans-1'-enyl)-3-endo-7-endo-dihydroxy;
2-exo-(3'S-hydroxy-oct-1'-trans-1'-enyl)-3-endo-7-endo-dihydroxy;
2-exo-(3'R-hydroxy-oct-1'-trans-1'-enyl)-3-endo-7-endo-dihydroxy;

2-exo-(3'S-hydroxy-4'S-methyl-oct-1'-trans-1'-enyl)-3-endo-7-endo-dihydroxy;
2-exo-(3'R-hydroxy-4'S-methyl-oct-1'-trans-1'-enyl)-3-endo-7-endo-dihydroxy;
2-exo-(3'S-hydroxy-non-1'-trans-1'-enyl)-3-endo-7-endo-dihydroxy;
2-exo-(3'R-hydroxy-non-1'-trans-1'-enyl)-3-endo-7-endo-dihydroxy;
2-exo-(3'S-hydroxy-5'-cyclohexyl-pent-1'-trans-1'-enyl)-3-endo-7-endo-dihydroxy;
2-exo-(3'S-hydroxy-5'-phenyl-pent-1'-trans-1'-enyl)-3-endo-7-endo-dihydroxy;
2-exo-(3'R-hydroxy-5'-phenyl-pent-1'-trans-1'-enyl)-3-endo-7-endo-dihydroxy;
2-exo-(3'S-hydroxy-4'-m-trifluoromethylphenoxy-but-1'-trans-1'-enyl)-3-endo-7-endo-dihydroxy;
2-exo-(3'R-hydroxy-4'-m-trifluoromethylphenoxy-but-1'-trans-1'-enyl)-3-endo-7-endo-dihydroxy;
2-exo-(3'S-hydroxy-4'-methyl-4'-butoxy-pent-1'-trans-1'-enyl)-3-endo-7-endo-dihydroxy;
2-exo-(3'R-hydroxy-4'-methyl-4'-butoxy-pent-1'-trans-1'-enyl)-3-endo-7-endo-dihydroxy.

EXAMPLE 27

Successive portions of a solution of 0.4 g of chromic anhydride are added with stirring to 4 ml of pyridine. Once the complex is formed, this mixture is treated with 0.36 g of 2-exo-(3'S-hydroxy-5'(2")-tetrahydrofuryl-pent-1'-trans-1'-enyl)-3-endo-7-exo-dihydroxy-bicyclo[3.3.0]octane-3,3'-bis-THP-ether in 4 ml of pyridine. The reaction mixture is held overnight at room temperature, diluted with 3 volumes of benzene, and filtered. The filtrate is then evaporated to give a residue which is partitioned between benzene and 2 N sulfuric acid. The aqueous portion is re-extracted with benzene, washed successively with water, NaHCO$_3$ and water, and evaporated to dryness to give 0.31 g of 2-exo-(3'S-hydroxy-5'(2"-tetrahydrofuryl-pent-1'-trans-1'-enyl)-3-endo-hydroxy-bicyclo[3.3.0]octan-7-one-3,3'-bis-THP-ether.

EXAMPLE 28

A stirred and cooled ($-10°-6°$ C.) solution of 0.8 g of 2-exo-(3'S-hydroxy-oct-1'-trans-1'-enyl)-3-endo-7-endo-dihydroxy-bicyclo[3.3.0]octane-3,3'-bis-THP-ether in 20 ml of acetone is treated with 1.6 ml of Jones' reagent in 15 minutes. After another 15 minutes of stirring, 80 ml of benzene is added. The organic phase is separated, washed with 15% aqueous (NH$_4$)$_2$SO$_4$ until neutral, dried and evaporated to dryness to afford 0.71 g of 2-exo-(3'S-hydroxy-oct-1'-trans-1'-enyl)-endo-hydroxy-bicyclo[3.3.0]octan-7-one-3,3'-bis-tetrahydropyranylether.

EXAMPLE 29

Using either of the oxidation procedures described in examples 27 and 28 on the triols of example 26, the following 3-endo-hydroxy-bicyclo[3.3.0]-octan-7-one-3,3'-bis-THP-ethers are prepared:
2-exo-(2'-bromo-3'S-hydroxy-4'R-fluoro-oct-1'-trans-1'-enyl);
2-exo-(2'-bromo-3'-R-hydroxy-4'R-fluoro-oct-1'-trans-1'-enyl);
2-exo-(3'S-hydroxy-5'(2")-tetrahydrofuryl-pent-1'-trans-1'-enyl);
2-exo-(3'R-hydroxy-5'(2")-tetrahydrofuryl-pent-1'-trans-1'-enyl);
2-exo-(2'-bromo-3'S-hydroxy-oct-1'-trans-1'-enyl);
2-exo-(2'-bromo-3'R-hydroxy-oct-1'-trans-1'-enyl);
2-exo-(3'S-hydroxy-oct-1'-trans-1'-enyl);
2-exo-(3'R-hydroxy-oct-1'-trans-1'-enyl);
2-exo-(3'S-hydroxy-4'S-methyl-oct-1'-trans-1'-enyl);
2-exo-(3'R-hydroxy-4'S-methyl-oct-1'-trans-1'-enyl);
2-exo-(3'S-hydroxy-non-1'-trans-1'-enyl);
2-exo-(3'R-hydroxy-non-1'-trans-1'-enyl);
2-exo-(3'S-hydroxy-5'-cyclohexyl-pent-1'-trans-1'-enyl);
2-exo-(3'R-hydroxy-5'-cyclohexyl-pent-1'-trans-1'-enyl);
2-exo-(3'S-hydroxy-5'-phenyl-pent-1'-trans-1'-enyl);
2-exo-(3'R-hydroxy-5'-phenyl-pent-1'-trans-1'-enyl);
2-exo-(3'S-hydroxy-4'-m-trifluoromethylphenoxy-but-1'-trans-1'-enyl);
2-exo-(3'R-hydroxy-4'-m-trifluoromethylphenoxy-but-1'-trans-1'-enyl);
2-exo-(3'S-hydroxy-4'-methyl-4'-butoxy-pent-1'-trans-1'-enyl);
2-exo-(3'R-hydroxy-4'-methyl-4'-butoxy-pent1'-trans-1'-enyl);

EXAMPLE 30

A solution of 2.1 g of d,l-2-exo-(3'-oxo-non-1'-trans-1'-enyl)-3-exo-THP-oxy-7-endo-DMtB-silyloxy-bicyclo[3.3.0]octane (prepared according to example 17) is reduced at $-15°$ C. in methylene chloride:ethanol with 0.17 g of NaBH$_4$, following the procedure of example 23, to afford 2.01 g of d,l-2-exo-(3'(S,R)-hydroxy-non-1'-trans-1'-enyl)-3-exo-THP-oxy-7-endo-DMtB-silyloxy-bicyclo[3.3.0]octane. Without separating the 3'S and 3'R alcohols, this product is reacted in 30 ml of methylene chloride with 0.4 g of 2,3-dihydropyran in the presence of 25 mg of p-toluenesulfonic acid to give the corresponding d,l-exo-(3'(S,R)-hydroxy-non-1'-trans-1'-enyl)-3-exo-hydroxy-7-endo-DMtB-silyloxy-bicyclo[3.3.0]octane-3,3'-bis-THP-ether. With no further purification, this product is treated with 2.5 molar equivalents of tetrabutyl ammonium fluoride in THF to remove the silyl ether.

The product d,l-2-exo-(3'(S,R)-hydroxy-non-1'-trans-1'-enyl)-3-exo-7-endo-dihydroxy-bicyclo[3.3.0]octane-3,3'-bis-THP-ether (1.660 g) is then oxidized with pyridine-chromic anydride to give 1.25 g of d,l-2-exo-(3'(S,R)-hydroxy-non-1'-trans-1'-enyl)-3-exo-hydroxy-bicyclo[3.3.0]octan-7-one-3,3'-bis-THP-ether.

EXAMPLE 31

A solution of (2-oxo-5,5,5-trimethoxy-pentyl)-dimethyl phosphonate in 10 ml of THF is added dropwise to a stirred suspension of 68 mg of NaH (80%) in 10 ml of anhydrous THF. Stirring is continued until hydrogen evolution ceases, and then a solution of 0.67 g of d,l-2-exo-(3'(S,R)-hydroxy-non-1'-trans-1'-enyl)-3-exo-hydroxy-bicyclo[3.3.0]octan-7-one-3,3'-bis-THP-ether in 5 ml of THF is added. After 6 hours of stirring at 40°-45° C., 20 ml of 20% NaH$_2$PO$_4$ is added and the THF is removed under vacuum. The residue is extracted with ethyl ether, and the organic extract is dried over Na$_2$SO$_4$ and evaporated. Adsorption of the residue on silica gel and elution with cyclohexane:ethyl ether afford 0.76 g of d,l-5t,13t-4-oxo-11β,15(S,R)-dihydroxy-20-methyl-9a-deoxy-9a-methylene-prostacycla-5,13-dienoic acid-trimethylorthoester-11,15-bis-THP-ether.

A solution of this product in 15 ml of anhydrous methanol is treated with 6 mg of p-toluenesulfonic acid for 5 hours at room temperature. 0.1 ml of pyridine is added, the solution is evaporated to dryness, and the residue is purified on silica gel (isopropyl ether:ethyl ether as eluent) to afford 0.20 g of d,l-5t,13t-4-oxo-11β,15S-dihydroxy-20-methyl-9a-deoxy-9a-methylene-prostacycla-5,13-dienoic acid-trimethylorthoester and 0.21 g of the 15R epimer.

EXAMPLE 32

Following the procedure of example 31 with a bicyclo[3.3.0]octan-7-one prepared as in examples 27, 28 and 29, the following trimethylorthoesters were prepared:
5,13t-4-oxo-11α,15S-dihydroxy-9a-deoxy-9a-methylene-prostacycla-5,13-dienoic acid;
5,13t-5-oxo-11α,15S-dihydroxy-9a-deoxy-9a-methylene-20-methyl-prostacycla-5,13-dienoic acid;
5,13t-4-oxo-11α,15S--dihydroxy-9a-deoxy-9a-methylene-17(2')-tetrahydrofuryl-18,19,20-trinor-prostacycla-5,13-dienoic acid;
5,13t-4-oxo-11α,15S-dihydroxy-9a-deoxy-9a-methylene-16-m-trifluoromethylphenoxy-17,18,19,20-tetranor-prostacycla-5,13-dienoic acid;
as well as their 15R epimers.

Each of the ortho-esters of examples 31 and 32 is then converted to its methyl ester by refluxing it in methanol (15 ml/g) with 2 ml of 0.2 N oxalic acid and recovering the product by evaporating the methanol and extracting with ethyl ether. Subsequent saponification with 2% KHCO$_3$ in 80% aqueousmethanol gives the free acid.

EXAMPLE 33

A solution of 0.45 g of 5,13t-4-oxo-11α,15S-dihydroxy-9a-deoxy-9a-methylene-prostacycla-5,13-dienoic acid-trimethylorthoester ($\lambda_{max}$=244 mµ, $\epsilon$=9,850) in 6 ml of methanol and 1.2 ml of 0.2 N oxalic acid is refluxed for two hours. Evaporation of the methanol under vacuum and extraction with ethyl ether give 0.42 g of the corresponding methyl ester.

A solution of this product in 6 ml of anhydrous ethyl ether is added dropwise to a stirred 0.1 M solution of zinc borohydride (10 ml) in 10 minutes. After 1 hour of stirring at room temperature, the reaction is quenched with 2 N sulfuric acid. The organic phase is separated, washed until neutral, and evaporated to dryness to give 0.4 g of 5,13t-4(S,R),11α,15S-trihydroxy-9a-deoxy-9a-methylene-prostacycla-5,13-dienoic acid methyl ester. Chromatographic separation on silica gel (ethyl ether:ethyl acetate as eluent) affords 0.11 g of 5,13t-4S,11α,15S-trihydroxy-9a-deoxy-9a-methylene-prostacycla-5,13-dienoic acid methyl ester and 0.14 g of the 4R-epimer methyl ester.

A solution of the latter compound in 5 ml of methanol is treated with 0.05 g of lithium hydrate and 0.3 ml of H$_2$O and then stirred at room temperature for 6 hours. Removal of the methanol under vacuum, acidification of pH 5.6 and rapid extraction with ethyl acetate afford 5,13t-4R,11α,15S-trihydroxy-9a-deoxy-9a-methylene-prostacycla-5,13-dienoic acid. Treatment of a stirred ethyl acetate solution of this compound with 0.5 parts of a polystyrenesulfonic resin (hydrogen ion form) gives 5,13t-4R,11α,15S-trihydroxy-9a-deoxy-9a-methylene-prostacycla-5,13-dienoic acid-1,4-γ-lactone quantitatively.

The 4S epimer-γ-lactone was prepared analogously.

EXAMPLE 34

A solution of 0.8 g of 5,13t-4-oxo-11α,15S-dihydroxy-20-methyl-9a-deoxy-9a-methylene-prostacycla-5,13-dienoic acid-trimethylorthoester-11,15-bis-THP-ether in 20 ml of methylene chloride:ethanol is cooled to −20° C. and treated with 50 mg of NaBH$_4$. After 30 minutes of stirring, the reaction is quenched with 2 ml of acetone and 5 ml of saturated monosodium phosphate. Evaporation of the methylene chloride and ethanol under vacuum and repeated extraction with ethyl ether afford, after the combined organic extract is dried and evaporated, 0.75 g of 5,13t-4(S,R),11α,15S-trihydroxy-20-methyl-9a-deoxy-9a-methylene-prostacycla-5,13-dienoic acid-trimethylorthoester-11,15-bis-THP-ether.

This crude product is dissolved in 2.2 ml of methanesulfonyl chloride. The reaction mixture is held overnight at room temperature and then partitioned between iced 2 N sulfuric acid and ethyl ether. The combined organic extract is washed with brine, dried and evaporated at low temperature to give 5,13t-4(S,R),11α,15S-trihydroxy-20-methyl-9a-deoxy-9a-methylene-prostacycla-5,13-dienoic acid-trimethylorthoester-4-mesylate-11,15-bis-THP-ether.

With no further purification, this product is dissolved in anhydrous ethyl ether and treated with 50 mg of lithium aluminum hydride in ethyl ether. After stirring for 2 hours at room temperature and 1 hour at reflux, the reaction mixture is quenched with 2 ml of ethyl acetate and then wet ethyl ether. Drying over Na$_2$SO$_4$ and evaporating the ethyl ether give 0.5 g of crude 5,13t-11α,15S-dihydroxy-20-methyl9a-deoxy-9a-methylene-prostacycla-5,13-dienoic acid-trimethylorthoester-11,15-bis-THP-ether.

After treatment at reflux with 12 ml of methanol and 4 ml of 0.3 N aqueous oxalic acid, standard work-up gives 0.2 g of 5,13t-11α,15(S)-dihydroxy-20-methyl-9a-deoxy-9a-methyleneprostacycla-5,13-dienoic acid methyl ester. Liquid-liquid chromatography shows that the product is mainly trans (85%), with 15% of the cis isomer.

EXAMPLE 35

In an inert gas atmosphere, a stirred suspension of 0.4 g of NaH (75% mineral oil dispersion) in 13.5 ml of DMSO is heated to 60°-65° C. for 4 hours. The mixture is then cooled to room temperature and held at 20°-22° C. while 2.6 g of 4-carboxy-butyl-triphenyl phosphonium bromide in 6 ml of DMSO and 0.85 g of 2-exo-(3'S-hydroxy-non-1'-trans-1'-enyl)-3-endohydroxy-bicyclo[3.3.0]octan-7-one-3,3'-bis-THP-ether are added successively. After stirring for 3 hours, the mixture is diluted with 35 ml of water and the aqueous phase is extracted with ethyl ether (5×12 ml) and ethyl ether:-benzene (7×12 ml). The combined organic extract is re-extracted with 0.5 N NaOH (3×15 ml) and then water until neutral, and then discarded. The combined aqueous alkaline extract is acidified to pH 5.3 and extracted with 1:1 ethyl ether:pentane. Washing until neutral, drying over Na$_2$SO$_4$ and removing the solvent afford 0.86 g of 5,13t-11α,15S-dihydroxy-9a-deoxy-9a-methylene-20-methyl-prostacycla-5,13-dienoic acid-11,15-bis-THP-ether. This product is then esterified by treatment with diazomethane, and the pyranyl protecting groups are removed, as follows:

The methyl ester is dissolved in anhydrous methanol and treated with a solution of 10$^{-2}$ molar equivalents of p-toluenesulfonic acid. After 4 hours, the p-toluenesulfonic acid is neutralized with pyridine and the mixture is evaporated to dryness. Purification on silica gel affords 5,13t-11α,15S-dihydroxy-9a-deoxy-9a-methylene-20-methyl-prostacycla5,13-dienoic acid methyl ester, which is then separated into the individual 5c,13t and 5t,13t isomers by liquid-liquid chromatography.

EXAMPLE 36

With stirring and external cooling to keep the reaction temperature at 20°-22° C., a solution of freshly sublimed potassium tert-butylate in 12 ml of anhydrous DMSO is treated successively with 1.8 g of 4-carboxybutyl-triphenyl phosphonium bromide in 10 ml of DMSO and 0.65 g of 2-exo-(2'-bromo-3'-S-hydroxy-oct-1'-trans-1'-enyl)-3-endo-hydroxy-bicyclo[3.3.0]octan-7-one-3,3'-bis-THP-ether in 5 ml of DMSO. After stirring for 8 hours at room temperature, the mixture is diluted with an equal volume of water, acidified to pH 5 and extracted with 1:1 ethyl ether:pentane. The acidic aqueous phase is discarded, and the combined organic extract is extracted with 0.8 N NaOH (5×20 ml) and then water water until neutral. While this organic phase is discarded, the aqueous alkaline extract is acidified to pH 5 and extracted with 1:1 ethyl ether:pentane. The combined extract is dried over $Na_2SO_4$, filtered and treated with ethereal diazomethane until a yellow coloration persists. Evaporation to dryness gives crude 11α,15S-dihydroxy-9a-deoxy-9a-methylene-prostacycl-5-en-13-ynoic acid methylester-11,15-bis-THP-ether. Removal of the pyranyl protecting group followed by liquid-liquid chromatography gives 5c-11α,15S-dihydroxy-9a-deoxy-9a-methylene-prostacycl-5-en-13-inoyc acid methyl ester, plus the 5t geometric isomer.

EXAMPLE 37

When the bicyclo[3.3.0]octan-7-one-3,3'-bis-THP-ethers prepared according to examples 27, 28, 29 and 30 were used in the procedure of examples 35 and 36, the methyl esters of the following acids were obtained:

5c,13t-11β,15S-dihydroxy-9a-deoxy-9a-methylene-prostacycla-5,13-dienoic acid;

5c-11α,15S-dihydroxy-9a-deoxy-9a-methylene-16R-fluoroprostacycl-5-en-13-ynoic acid;

5c-11α,15S-dihydroxy-9a-deoxy-9a-methylene-16S-fluoroprostacycl-5-en-13-ynoic acid;

5c-11α,15S-dihydroxy-9a-deoxy-9a-methylene-17(2')--tetrahydrofuryl-18,19,20-trinor-prostacycl-5-en-13-ynoic acid;

5c-11α,15S-dihydroxy-9a-deoxy-9a-methylene-prostacycl-5-en-13-ynoic acid;

5c,13t-11α,15S-dihydroxy-9a-deoxy-9a-methylene-prostacycla5,13-dienoic acid;

5c,13t-11α,15S-dihydroxy-9a-deoxy-9a-methylene-16S-methylprostacycla-5,13-dienoic acid;

5c,13t-11α,15S-dihydroxy-9a-deoxy-9a-methylene-20-methylprostacycla-5,13-dienoic acid;

5c,13t-11α,15S-dihydroxy-9a-deoxy-9a-methylene-17-phenyl-18,19,20-trinor-prostacycla-5,13-dienoic acid;

5c,13t-11α,15S-dihydroxy-9a-deoxy-9a-methylene-16-m-$CF_3$-phenoxy-17,18,19,20-tetranor-prostacycla-5,13-dienoic acid;

5c,13t-11α,15S-dihydroxy-9a-deoxy-9a-methylene-16-methyl-16-butoxy-18,19,20-trinor-prostacycla-5,13-dienoic acid;

As well as their 5-trans geometric isomers, plus the 15 R epimers of both.

These were then saponified to give the free acids.

EXAMPLE 38

A solution of 0.45 g of 2-exo-(3'S-hydroxy-oct-1'-trans-1'-enyl)-3-endo-hydroxy-bicyclo[3.3.0]octan-7-one-3,3'-bis-THP-ether in ethyl acetate is hydrogenated at ambient temperature and pressure in the presence of 0.1 g of 5% $Pd/CaCO_3$, until 1.01 equivalents of hydrogen are absorbed. Filtration and evaporation to dryness give 0.42 g of 2-exo(3'-hydroxy-octan-1'-yl)-3-endo-hydroxy-bicyclo[3.3.0]octan-7-one-3,3'-bis-THP-ether. Treatment of this with the Wittig reagent prepared from 4-carboxy-butyl phosphonium bromide according to examples 35, 36 and 37 affords a product which is esterified with diazomethane and depyranylized to give 0.12 g of 11α,15S-dihydroxy-9a-deoxy-9a-methyleneprostacycl-5-enoic acid methylester. The 5-cis and 5-trans geometric isomers are separated by liquid-liquid chromatography.

EXAMPLE 39

Using (3-carboxy-propyl)-phosphonium bromide in the procedure of examples 37 and 38 instead of (4-carboxy-butyl)phosphonium bromide gave the following acids:

5c,13-11α,15S-dihydroxy-9a-deoxy-9a-methylene-2-nor-prostacycla-5,13-dienoic;

5c,11α,15S-dihydroxy-9a-deoxy-9a-methylene-2-nor-prostacycl5-enoic;

5c,11α,15S-dihydroxy-9a-deoxy-9a-methylene-2-nor-prostacycl5-en-13-ynoic acid.

EXAMPLE 40

By using (5-carboxy-pentyl)-phosphonium bromide in the procedure of examples 37 and 38, 5c,13t-11α,15S-dihydroxy-9a-deoxy-9a-methylene-2ahomo-prostacycla-5,13-dienoic acid and 5,13t-11α,15S-dihydroxy-9a-deoxy-9a-methylene-20-methyl-2-ahomo-prostacycla-5,13-dienoic acid were prepared.

EXAMPLE 41

A solution of 0.37 g of 5c,13t-11α,15S-dihydroxy-9a-deoxy-9a-methylene-prostacycla-5,13-dienoic acid methyl ester in 10 ml of benzene is heated to 50° C. with 250 mg of 2,3-dichloro-5,6-dicyano-benzoquinone for 8 hours. The precipitate is removed by filtration, and the benzene solution is purified on a short alumina column to give 0.29 g of 5c,13t-11α-hydroxy-15-oxo-9a-deoxy-9a-methylene-prostacycla5,13-dienoic acid methyl ester.

A solution of this product in ethyl ether:toluene is cooled to $-20°$ C. and treated with 1.2 ml of 1 M methyl magnesium bromide in ethyl ether. After 2.5 hours at $-20°$ C., the reaction is quenched with $NH_4Cl$ solution. The organic phase is separated, reduced in volume and purified on silica gel (ethyl ether:ethyl acetate as eluent) to give 0.1 g of 5c,13t-11α,15S-dihydroxy-15-methyl-9a-deoxy-9a-methylene-prostacycla-5,13-dienoic acid methyl ester and 0.072 g of the 15 R hydroxy epimer.

EXAMPLE 42

A solution of 2.2 g of 3-endo-hydroxy-bicyclo[3.3.0]octan-7-one in 100 ml of anhydrous benzene is treated with 4 ml of ethylene glycol and 0.2 g of p-toluenesulfonic acid monohydrate and refluxed for 12 hours while the water which forms druing the reaction is collected. 0.25 ml of pyridine is then added and the mixture is cooled. The organic phase is washed with water, $NaHCO_3$ and then water, and evaporated to dryness to give 2.32 g of 3-endo-hydroxy-bicyclo]3.3.0]octan-7-one-7,7-ethylenedioxide.

A solution of this product in 40 ml of acetone is cooled to $-5°$ C. and treated at this temperature with 4.1 ml of Jones' reagent. After 20 minutes at −5° C., excess oxidant is quenched with 4 ml of isopropyl alcohol. 150 ml of benzene is added, and the benzene phase is washed successively with 20% $(NH_4)_2SO_4$, water, 5% $NaHCO_3$ and water. Evaporation to dryness gives 2.1 g of d,l-bicyclo[3.3.0]octan-3,7-dione-2-carboxymethylester7,7-ethylenedioxide.

According to the procedure of example 2, a solution of this product in 20 ml of $CH_2Cl_2$ and 20 ml of ethanol is reduced with $NaBH_4$ at −20° C. to give 1.72 g of d,l-3-endo-hydroxybicyclo[3.3.0]octan-7-one-2-exo-carboxymethylester-7,7-ethylenedioxide.

A solution of 1.57 g of this compound in 3 ml of dimethylformamide is treated with 1.3 g of dimethyl-tertbutyl-silyl chloride and 0.885 g of imidazol, and then held at 0° C. for 5 hours. After cooling, water is added and the usual work-up affords 2.3 g of d,l-3-endo-hydroxy-bicyclo[3.3.0]octan-7-one-2-exo-carboxymethylester-7,7-ethylenedioxide-3-dimethyl-tert-butylsilylether. Subsequent reduction with $LiAlH_4$ in anhydrous ethyl ether, as described in example 3, gives d,l-3-endo-hydroxy-2-exo-hydroxymethyl-7,7-ethylenedioxy-bicyclo[3.3.0]octan-7-one-3-dimethyl-tert-butyl silyl ether quantitatively.

EXAMPLE 43

By using dithioethylene glycol in the procedure of example 42 instead of ethylene glycol, the corresponding 7,7-ethylenedithio analogues were prepared.

EXAMPLE 44

1.8 g of d,l-3-endo-hydroxy-2-exo-hydroxymethyl-7,7-ethylenedioxy-bicyclo-[3.3.0]-octan-7-one-3-dimethyl-tert-butyl silyl ether is oxidized according to the procedure of example 18 to give the corresponding 2-formyl derivative. This is then reacted with (2-oxoheptyl)-dimethyl phosphonate as in example 20 to give 1.23 g of d,l-3-endo-hydroxy-2-exo-(3'-oxo-oct-1'-trans-1'-enyl)-7,7-ethylenedioxy-bicyclo[3.3.0]octan7-one-3-dimethyl-tert-butyl silylether ($\lambda_{max}$=228m$\mu$, $\epsilon$=8980). According to the procedure in example 22, this is reduced with zinc borohydride in ether to give 1.22 g of d,l-3-endohydroxy-2-exo-(3'(S,R)-hydroxy-oct-1'-trans-1'-enyl)-7,7-ethylenedioxy-bicyclo[3.3.0]octan-7-one-3-dimethyl-tert-butyl silylether.

A solution of this compound in 25 ml of methanol is treated with 10 ml of 1 N $H_2SO_4$ at reflux for 50 minutes. The methanol is evaporated under vacuum, the residue is extracted with ethyl ether, and the organic phase is evaporated to dryness to afford 0.72 g of crude d,l-3-endo-hydroxy-3-exo-(3'(S,R)-hydroxy-oct-1'-trans-1'-enyl)-bicyclo]3.3.0]octan-7-one. The individual isomers are separated by chromatography on silica gel with hexane:ethyl ether as eluent and then converted to the tetrahydropyranyl ethers by treatment with 2,3-dihydropyran in methylene chloride as in example 25. In this fashion, a compound identical in all respects to 2-exo-(3'S-hydroxy-oct-1'-trans-1'-enyl)-3-endo-hydroxybicyclo[3.3.0]octan-7-one-3,3'-bis-tetrahydropyranylether prepared as in example 28 is prepared from the 3'S-hydroxy isomer.

Similarly, with the procedure of examples 42 and 44, all the compounds prepared as in examples 27, 28 and 29 were obtained.

EXAMPLE 45

Saponification of 4.8 g of d,l-3-endo-hydroxy-2-exo-carboxymethylester-7,7-ethylenedioxy-bicyclo[3.3.0]octan-7-one with 100 ml of 2.5% potassium carbonate in 80:20 methanol:water at reflux for 40 minutes and subsequent work-up as described in example 2 gave 4.02 g of d,l-3-endo-hydroxy-2-exo-carboxybicyclo[3.3.0]octan-7-one-7,7-ethylenedioxide. This compound is dissolved in 80 ml of anhydrous tetrahydrofruan, cooled to −10° C., and treated dropwise with 2.1 g of triethylamine in 12 ml of anhydrous tetrahydrofuran and then 2.2 g of ethyl chlorocarbonate in 12 ml of anhydrous tetrahydrofuran, while keeping the temperature at −10° C. After 1 hour of stirring at −10° C., 1.4 g of sodium azide in 12 ml of water is added slowly and stirring is continued for another 25 minutes. The reaction mixture is then concentrated under vacuum and diluted with water. The 2-exo-carboxy-azide is isolated rapidly by filtration and dried under vacuum.

A solution of 4.01 g of this compound in 8 ml of pyridine is treated with 4 ml of acetic anhydride and held at 5°–8° C. for 24 hours. The reaction mixture is then partitioned between ice water, ethyl ether and 2 N sulfuric acid. The organic layer is separated, washed until neutral, dried and evaporated to dryness to give 4.1 g of 3-endo-hydroxy-2-exo-carboxyazide-bicyclo[3.3.0]octan-7-one-3-acetate-7,7-ethylenedioxide.

This product is suspended in acetic acid (50 ml) and water (8 ml), and the mixture is heated to 40° C. When hydrogen evolution is noted, it is heated to 60°–70° C. for 2 hours, after which the excess acetic acid is removed by steam distillation. After cooling, the mixture is extracted with ethyl ether:ethyl acetate and the aqueous phase is brought to pH 9 with sodium hydrate. The alkaline phase is washed with saturated salt solution and evaporated to dryness to give 1.92 g of 3-endo-hydroxy-2-exo-amino-bicyclo[3.3.0]octan-7-one-3-acetate. Reaction of this with the mixed anhydride from ethoxycarboyl chloride and 2S-hydroxy-heptanoic acid-2-acetate affords 3-endo-hydroxy-2-exo-(2'S-acetoxyheptanoylamide)-bicyclo[3.3.0]octan-7-one-3-acetate. A solution of this compound in anhydrous dimethylsulfoxide is then reacted with the ylide obtained from 4-carboxybutyl-triphenyl phosphonium bromide to give, after saponification, 5t-11$\alpha$,15S-dihydroxy-9a-deoxy-9a-methylene-13-aza-14-oxo-prostacycl-5-enoic acid.

In an analogous fashion the 15R-epi analogue was prepared from the 2'R-hydroxy-heptanoic acid.

EXAMPLE 46

Ethylene glycol (15 ml) and p-toluenesulfonic acid (0.9 g) are added to a solution of 2-exo-bromo-3-endo-hydroxy-bicyclo[3.2.0] heptane-6-one in benzene and the mixture is refluxed for 12 hours, withdrawing water which forms during the reaction, then the mixture is added by piridine (0.6 ml) and cooled at room temperature.

The organic phase is washed with water, 2.5% aqueous $NaHCO_3$ and water, dried. Benzene (100 ml) is partially removed in vacuum, then the mixture is treated with tributyl tin-hydride (41 g) in $N_2$ atmosphere at 55° for 8 hours. After cooling at room temperature the organic phase is washed with saturated aqueous $NaH_2PO_4$, dried and evaporated to dryness. Purification of the resulting residue on $SiO_2$ (240 g) with benzene-ethylether as eluent affords 14.9 g of 3-endo-hydroxy-bicyclo[3.2.0]heptane-6-one-6,6-ethylene dioxide.

EXAMPLE 47

A stirred solution of 3-endo-hydroxy-bicyclo[3.2.0]heptane-6-one-6,6-ethylendioxide (12.75 g) in benzene (340 ml) and DMSO (112 ml) was treated with dicyclohexylcarbodiimide (46.35 g), pyridine (5.9 g) and trifluoroacetic acid (5.4 g). After 6 hours, the mixture is diluted with benzene (600 ml) and water (50 ml), filtered from dicyclohexylurea and the organic phase is washed with water, dried on $MgSO_4$ and evaporated to dryness affording bicyclo[3.2.0]heptane-3,6-dione-6,6-diethylenedioxide.

A solution of this crude product in dimethylcarbonate (70 ml) is added to a suspension of sodium hydride (80% in mineral oil, 4 g). The mixture is stirred until $H_2$ development ceases at room temperature then it is warmed for 40 minutes at 75°–80°.

After cooling, the reaction mixture is diluted with benzene (350 ml) and acetic acid (8.4 g), washed with water, dried and evaporated to dryness affording a mixture (1:1) of d,l-bicyclo[3.2.0]heptane-3,6-dione-2-carboxy methylester-6,6-ethylenedioxide (p=0, q=1) and d,l-bicyclo-[3.2.0]heptane-3,6-dione-4-carboxymethylester-6,6-ethylene dioxide (p=1, q=0) which are separated by means of chromatography on $SiO_2$ ($Fe^{++}$, $Fe^{+++}$ free) using hexane-ethylether as eluents.

EXAMPLE 48

Using in the procedure of the example 47 g 14.85 of 3-endo-hydroxybicyclo[4.3.0]nonane-7-one-7,7-ethylendioxide the oxidation process affords 13.9 g of bicyclo[4.3.0]nonane-3,7-dione-7,7-ethylenedioxide giving the carbomethoxylation process 4.2 g of dl-bicyclo[4.3.0]nonane-3,7-dione-2-carboxymethylester-7,7-ethylenedioxide (p=1, q=2) and 4.8 g of dlbicyclo[4.3.0]nonane-3,7-dione-4-carboxymethylester-7,7-ethylenedioxide also named as dl-bicyclo[4.3.0]nonane-3,8-dione-2--carboxymethylester-8,8-ethylenedioxide (p=2, q=1).

EXAMPLE 49

A stirred solution of bicyclo[4.3.0]nonane-7-en-3-one (90 g) in dimethyl carbonate (350 ml) is added to a suspension of sodium hydride (80% dispersion in mineral oil, 42 g) in dimethylcarbonate (550 ml). After ceasing the hydrogen evolution, the mixture is heated for 4.5 hours at 75°–80°, cooled at r.t., diluted with benzene (2.7 l) and washed with 25% aqueous $NaH_2PO_4$ solution, evaporated to dryness affording bicyclo[4.3.0]nonane-7-ene-3-one-2-carboxymethylester (91 g) ($\lambda$max 252 m$\mu$ $\epsilon$=8.200).

A solution of this compound in methylene chloride (1.1 l) and ethanol (1.2 l) is cooled at −20° C. and, under stirring, treated with $NaBH_4$ (14.4 g).

The mixture is stirred for 30 minutes, again at −20°, then it is treated with acetic acid (23 ml), warmed at room temperature, and the solvents are evaporated in vacuum.

The residue is partitioned between ethyl acetate and water, the organic phase is dried and evaporated in vacuum affording dl-bicyclo[4.3.0]nonane-7-ene-3-endo-hydroxy-2-exo-carboxymethylester (64 g) which is dissolved in dry tetrahydrofuran (THF) and treated with 2,3-dihydropyrane (33 g) and p-toluensulphonic acid (0.63 g) for 3 hours at r.t. Pyridine (0.4 g) is added to the reaction mixture and then, after cooling at 0° C., under stirring a solution of 1.2 M $BH_3$ in THF is also added during 45 minutes. The stirring goes on for 1 hour at 0° C. then water is added to destroy residual hydride. Under vigorous stirring, with external cooling at −5+0°, the formed borane is oxidized by the slow concurrent addition of 110 ml of 3 M sodium hydroxide and 110 ml of 30% hydrogen peroxide, maintaining the internal temperature at 20°–25°. The oxidation mixture is diluted with benzene (2 l) and the layers are separated. The aqueous layer is extracted with benzene (2×50). The organic layers are combined, washed successively with 1% sodium carbonate, saturated sodium sulphite and saturated sodium chloride and dried on $MgSO_4$. Evaporation of the solvents affords a crude mixture of 7 and 8 hydroxy compounds which are separated by means of $SiO_2$ (300 g) column chromatography, ethyl ether as eluent, obtaining respectively:

dl-bicyclo[4.3.0]nonane-3-endo, 7$\epsilon$-dihydroxy-2-exo-carboxymethylester-3-THP-ether (24 g) and dl-bicyclo[4.3.0]nonane-3-endo, 8$\epsilon$-dihydroxy-2-exo-carboxymethylester-3-THP-ether (27 g).

A solution of the 7$\epsilon$-hydroxy alcohol (24 g) in dry DMF (30 ml) is treated with dimethyl-ter-butyl-silyl chloride (15.8 g) and imidazole (8.85 g) and then it is heated for 5 hours at 60°, cooled at room temperature, diluted with water (90 ml) and then extracted with ethyl ether.

The organic layers are collected, washed with water and evaporated to dryness affording dl-bicyclo[4.3.0]nonane-3-endo, 7$\epsilon$-dihydroxy-2-exo-carboxymethylester-3-THP-ether-7-DMB-silylether.

To a stirred solution of this compound in dry toluene (220 ml) cooled at −70°, a solution of 1.4 M DIBA in toluene is added over a period of 45 minutes, maintaining the temperature between −70+ −60°. The stirring is continued for 2 hours, the residual hydride is destroyed by addition of 2 M isopropyl alcohol in toluene.

The reaction mixture is warmed at room temperature and successively 30% aqueous $NaH_2PO_4$ (60 ml) and $Na_2SO_4$ (50 g) are added. After filtration, the organic phase is washed with water and evaporated in vacuum affording dl-bicyclo[4.3.0]3-endo, 7$\epsilon$-dihydroxy-2-exo-formyl-3-THP-ether-7-DMB-silyl ether (p=2, q=1). Using in this procedure the 8$\epsilon$-hydroxy compound, we have obtained:

dl-bicyclo[4.3.0]nonane-3-endo, 8$\epsilon$-dihydroxy-2-exo-carboxymethylester-3-THP-ether-8-DMB-silylether and dl-bicyclo[4.3.0]nonane-3-endo, 8$\epsilon$-dihydroxy-2-exo-formyl-3-THP-ether, 8-DMB-silylether.

EXAMPLE 50

A solution of (2-oxo-heptyl)dimethylphosphonate (0.33 g) in dry benzene (5 ml) is added to a stirred suspension of NaH (80% dispersion in mineral oil, 43.5 mg) in dry benzene (10 ml). After 1 hour N-Br-succinimide (260 mg) is added and then, after 5 minutes, a solution of bicyclo[4.3.0]nonane-3-endo, 8$\epsilon$-dihydroxy-2-exo-formyl-3-THP-ether, 8-DMB-silylether (0.4 g) in toluene (5 ml).

The stirring is continued for 15 minutes, then the reaction mixture is washed with aqueous 15% $NaH_2PO_4$, dried and evaporated in vacuum to give 2-exo[2'-bromo-3'-oxo-oct-1'-trans-enyl]-3-endo-THP-oxy-8$\epsilon$-DMB-silyloxybicyclo[4.3.0]nonane, $\lambda$ max 251 m$\mu$, $\epsilon$=8.900.

EXAMPLE 51

A solution of (3-phenoxy-2-oxo-propyl)dimethylphosphonate (2.85 g) in benzene (10 ml) is added to a stirred suspension of NaH (80% mineral oil dispersion, 0.33 g) in benzene (50 ml). The stirring is continued for 45 minutes, then a solution of 2-exo-formyl-3-endo-THP-oxy-7ξ-DMB-silyloxy-bicyclo[4.3.0]nonane (3.82 g) in toluene is added. After 20 minutes the organic phase is washed with aqueous 20% $NaH_2PO_4$ and water, dried and evaporated to dryness affording after filtration on $SiO_2$ (38 g), using benzene-ethyl ether as eluent, 2-exo-[3'-oxo-4'-phenoxy-but-1'-trans-enyl]-3-endo-THP-oxy-7ξ-DMB-silyloxy-bicyclo[4.3.0]nonane (3.97 g). Using in the procedure (5-cyclohexyl-2-oxo-butyl)-dimethyl phosphonate and starting from the aldehydes of the example 49 we have obtained:

2-exo-[3'-oxo-5'-cyclohexyl-pent-1'-trans-enyl]-3-endo-THP-oxy-7ξ-DMB-silyloxy-bicyclo[4.3.0]nonane λ max 228 mμ, ε=9.300

2-exo[3'-oxo-5'-cyclohexyl-pent-1'-trans-enyl]-3-endo-THP-oxy-8ξ-DMB-silyloxy-bicyclo4.3.0nonane λ max 228.6 mμ, ε=9.450.

EXAMPLE 52

The DMB-silylether-α,β-unsaturated ketones, obtained in accordance with the procedure of the examples 50, 51 (a) are reduced to allylic alcohols and (b) the new hydroxy group is protected as THP-ether; successively (c) the DMB-silylether protecting group is selectively removed given a secondary alcohol which (d) is oxidized to ketone; finally after removal (e) of all the remaining protective groups (f) the epimeric allylic alcohols are separated by HPLC-chromatography on $SiO_2$. Working in a $2.10^{-2}$ molar scale, the following procedure is used:

(a) reduction: $1.10^{-2}$ mole (0.32 g) of $NaBH_4$ is added to a stirred solution of a α,β-unsaturated ketone-DMB-silylether ($2.10^{-2}$ m) in methylene chlorideethanol (1:1) (180 ml) cooled at $-10°\div-15°$. After 30 minutes, the residual hydride is destroyed by adding acetone (10 ml) and aqueous saturated $NaH_2PO_4$ (25 ml). The solvents are removed in vacuum and the residue is partitioned between water and methylene chloride. The organic layer is separated dried and evaporated to dryness affording a mixture of 3'S, 3'R allylic alcohols-silylethers ($2.10^{-2}$ m).

(b) protection of allylic alcohols as THP-ethers: the crude mixture of 3'S, 3'R-allylic alcohols silylether ($2.10^{-2}$ m) was treated with methylene chloride (30 ml) and to the stirred solution 2,3-dihydropyrane (2 g) and p-toluensulphonic acid (0.038 g) are added. The reaction is complete after 2 hours stopped by addition of pyridine (0.5 ml) and the solvents are removed by evaporation in vacuum to give a crude mixture of 3'S, 3'R-THP-ether-silylethers.

(c) desilylation: a solution of the above obtained material in dry THF (80 ml) is treated for 12 hours at r.t. with dry tetrabutylammonium fluoride (14 ). After concentration in vacuum to small volume, the residue is absorbed on $SiO_2$ (40 g) and following elution with ethylether affords the secondary alcohol-3'S, 3'R-THP-ethers (about $2.10^{-2}$ m).

(d) oxidation: dicyclohexylcarbodiimide (6.5 g), pyridine (1 ml) and trifluoro acetic acid (0.5 ml) are added successively to a stirred solution in 75:25 benzene-DMSO (60 ml) of the secondary alcohol-3'S, 3'R-THP-ether. After 4.5 hours the reaction mixture is diluted with benzene (100 ml) and with a solution of oxalic acid (3 g) in water. Formed dicyclohexylurea is filtered, organic layer is washed with neutral, dried and evaporated to dryness.

(e,f) depyranylization and chromatographic separation: a solution of the 3'S, 3'R-THP-ether-ketones in methanol (30 ml) is stirred at r.t. for 3 hours with p-toluenesulphonic acid (0.18 g); after addition of pyridine (0.5 ml) it is evaporated to dryness. The residue is dissolved in cyclohexane-ethyl acetate (80:20) and injected in HPLC instrument to give the following keto alcohols:

2-exo[2'bromo-3'S-hydroxy-oct-1'-trans-enyl]-3-endohydroxy-bicyclo[4.3.0]nonane-8-one 2-exo[2'bromo-3'R-hydroxy-oct-1'-trans-enyl]-3-endo hydroxy-bicyclo[4.3.0]nonane-8-one 2-exo[3'S-hydroxy-4'-phenoxy-but-1'-trans-enyl]-3-endo hydroxy-bicyclo[4.3.0]nonane-7-one 2-exo[3'R-hydroxy-4'-phenoxy-but-1'-trans-enyl]-3-endo hydroxy-bicyclo [4.3.0]nonane-7-one 2-exo[3'S-hydroxy-5-cyclohexyl-pent-1'-trans-enyl]-3-endo hydroxy-bicyclo[4.3.0]nonane-7-one 2-exo[3'R-hydroxy-5-cyclohexyl-pent-1'-trans-enyl]-3-endo hydroxy-bicyclo[4.3.0]nonane-7-one 2-exo[3'S-hydroxy-5-cyclohexyl-pent-1'-trans-enyl]-3-endo hydroxy-bicyclo[4.3.0]nonane-8-one 2-exo[3'R-hydroxy-5-cyclohexyl-pent-1'-trans-enyl]-3-endo hydroxy-bicyclo[4.3.0]nonane-8-one.

EXAMPLE 53

Under a $N_2$ atmosphere, a suspension of NaH (80% dispersion in mineral oil, 2.1 g) in dry DMSO (70 ml) is stirred for 4 hours at 65°. After cooling at 25°–30°, dry 4-carboxy-butyl-triphenyl phosphonium bromide (13 g) is added to it, obtaining a deep red solution of the ylide.

After addition of a solution of 2-exo[2'bromo-3'S-hydroxy-oct-1'-trans-enyl]-3-endo hydroxy-bicyclo[4.3.0]nonane-8-one (1.79 g) in dry DMSO (6 ml), the reaction mixture is stirred for 1 hour at 28° and then for 4 hours at 40°; afterwards it is cooled at r.t., diluted with water (80 ml), acidified up to pH 4.5 by adding 4 N $H_2SO_4$ and extracted with ethyl ether (4×50 ml, 2×25). The aqueous layer is discarded, the organic phases are combined washed with water (this washing is discarded), then with N NaOH (5×10 ml) and water until neutral. The combined alkaline extracts are acidified up to pH 5 and extracted with ethyl ether to give 5(Z,E)-11α,15S-dihydroxy-9a-deoxy-9a,9b-dimethylene-prostacycla-5-en-13-ynoic acid (a mixture of 5 c- and 5 t-isomers). The individual geometric isomers are obtained after chromatographic separation on acidic $SiO_2$ (40 g/each g of acid) using cyclohexane-ethyl acetate as eluents.

EXAMPLE 54

Under a $N_2$ atmosphere, to a stirred solution of potassium-ter-butoxide (3.36 g), freshly sublimated, in dry DMSO (36 ml) it is added 6.5 g of 4carboxy-butyl-triphenyl-phosphonium bromide to give a deep red solution of the ylide. After addition of a solution of 2-exo[3'R-hydroxy-4'-phenoxybut-1'trans-enyl]3-endo hydroxy-bicyclo[4.3.0]nonane-7-one (0.8 g) in dry DMSO (3 ml), the reaction mixture is stirred for 5 hours at 42°, cooled diluted with water (50 ml) acidified up to pH 5 and extracted with ethyl ether (4×10 ml). The aqueous phase is discarded the combined ethereal extracts are washed with water (10 ml, this washing is discarded), and with 0.5 N NaOH (4×6 ml) and water until neutral. The combined alkaline extracts are acidified up to pH 5 and extracted with ethyl ether. The organic phases are combined dried and evaporated to dryness to give:

5(Z,E), 13t-11α,15R-dihydroxy-9a-deoxy-9a,7a homodimethylene-16-phenoxy-17,18,19,20-tetranor-prostacycla-5,13-dienoic acid (a mixture of 5 c and 5 t-geometrical isomers).

The individual geometric isomers are obtained after chromatographic separation on acidic $SiO_2$ (40 g/each g of acid) using cyclohexane-ethyl acetate as eluents.

EXAMPLE 55

Using the keto alcohols of the example 51 in the procedure of the examples 53, 54 we have prepared the following prostacyclanoic acids:

5c-11α,15S-dihydroxy-9a-deoxy-9a,9b-dimethyleneprostacycla-5-en-13-ynoic acid 5c,13t-11α,15S-dihydroxy-9a-deoxy-9a,7a homodimethylene-16-phenoxy-17,18,19,20-tetranor-prostacycla-5,13-dienoic acid 5c,13t-11α,15S-dihydroxy-9a-deoxy-9a,9b-dimethylene-17-cyclohexyl-18,19,20-trinor-prostacycla-5,13-dienoic acid 5c,13t-11α,15S-dihydroxy-9a-deoxy-9a,7a homodimethylene-17-cyclohexyl-18-19,20-trinor-prostacycla-5,13-dienoic acid 5t-11α,15S-dihydroxy-9a-deoxy-9a,9b-dimethyleneprostacycla-5-en-13-ynoic acid 5t,13t-11α,15S-dihydroxy-9α-deoxy-9a,7a homodimethylene-16-phenoxy-17,18,19,20-tetranor-prostacycla-5,13-dienoic acid 5t,13t-11α,15S-dihydroxy-9a-deoxy-9a,9b-dimethylene-17-cyclohexyl-18,19,20-trinor-prostacycla-5,13-dienoic acid 5t,13t-11α,15S-dihydroxy-9a-deoxy-9a,7a homodimethylene-17-cyclohexyl-18,19,20-trinor-prostacycla-5,13-dienoic acid.

EXAMPLE 56

Using the procedure of the example 46, 30 g of 2-acetoxyperhydroazulen-6-one, also named as 3-endo-hydroxy-bicyclo[5.3.0]decane-8-one acetate (obtained in accordance with D. K. Banerjee et al. Indian J. Chem. 10, 1, 1972) is transformed into its ethylendioxide (29.1 g). Then the compound is saponified by treatment with 2% $K_2CO_3$ in aqueous methanol to give 3-endo-hydroxy-bicyclo[5.3.0]decane-8-one-8,8-ethylenedioxide and oxidized using the procedure of the example 47 and treated with dimethylcarbonate (see the procedure of example 47) to obtain dl-bicyclo[5.3.0]decane-3,8-dione-2-carboxymethylester-8,8-ethylene dioxide, 21.2 g, λ max 254 nm; ε=7.000.

EXAMPLE 57

The bicyclo-β-keto ester-ethylene dioxides obtained in the examples 47, 48 and 56 are reduced with the following procedure: $NaBH_4$ (0.9 g) is added portionwise to a stirred solution of the bicyclo-β-keto ester-ethylenedioxides ($2.5.10^{-2}$ m) in 1:1 methylene chloride-ethanol (150 ml), cooled at −20°. After additional stirring for 30 minutes at −20°, the residual hydride is destroyed by adding acetone (12 ml). The reaction mixture is warmed at room temperature treated with aqueous 20% $KH_2PO_4$ and after removal of solvents, and dilution with water (20 ml) it is extracted with methylene chloride. The organic phases are combined, washed until neutral with water, dried and evaporated to dryness. The residue is equilibrated by treatment with absolute methanol (20 ml) and sodium methoxide (0.54 g), for 12 hours at r.t.; acetic acid (0.59 g) addition followed by evaporation of solvents and extraction with methylene chloride gives about $0.22.10^{-2}$ m of the following bicyclo-β-hydroxy ester-ethylenedioxides:

dl-3-endo hydroxy-bicyclo[3.2.0]heptane-6-one-2-exo-carboxymethylester-6,6-ethylene dioxide dl-3-endo hydroxy-bicyclo[3.2.0]heptane-6-one-4-exo-carboxymethylester-6,6-ethylene dioxide, also named as: dl-3-endo hydroxy-bicyclo[3.2.0]heptane 7-one-2-exo-carboxymethylester-7,7-ethylene dioxide dl-3-endo hydroxy-bicyclo[4.3.0]nonane-7-one-2-exo-carboxymethylester-7,7-ethylene dioxide dl-3-endo hydroxy-bicyclo[4.3.0]nonane-8-one-2-exo-carboxymethylester-8,8-ethylene dioxide dl-3-endo hydroxy-bicyclo[5.3.0]decane-8-one-2-exo-carboxymethylester-8,8-ethylene dioxide.

In the following, a solution of $2.10^{-2}$ m of each of these compounds in dry methylene chloride, 25 ml, is reacted with 2,3-dihydropyran (2 g) and p-toluensulphonic acid (38 mg, $2.10^{-4}$ m) for 2 hours at r.t. The reaction is stopped by adding pyridine (0.1 ml) and the mixture is evaporated to dryness in vacuum affording the corresponding 3-THP-ethers which are used without any further purification.

EXAMPLE 58

The 3-endo-hydroxy-2-exo-carboxymethylesters and their 3-THP-ethers, obtained with the procedure of the example 57 are reduced to give the corresponding 2-exo-hydroxymethyl derivatives with following procedure: a solution of $2.10^{-2}$ m of the β-ketoester (both alcohol and 3-THP ether) in dry ethylether (25 ml) is added dropwise to a stirred suspension of $LiAlH_4$ (0.4) in dry ethylether (50 ml). After additional stirring for 30 minutes the residual hydride is destroyed by adding acetone (5 ml) and ethylether saturated with water. Dry $MgSO_4$, 12 g, is added to, then the organic phase is filtered and evaporated to dryness.

We obtain the following 3-endohydroxy-2-exohydroxymethyl:

bicyclo[3.2.0]heptane-6-one-6,6-ethylenedioxide
bicyclo[3.2.0]heptane-7-one-7,7-ethylenedioxide
bicyclo[4.3.0]nonane-7-one-7,7-ethylenedioxide
bicyclo[4.3.0]nonane-8-one-8,8-ethylenedioxide
bicyclo[5.3.0]decane-8-one-8,8-ethylenedioxide
and their 3-endo-hydroxy-THP-ethers both racemic and optical active form (nat, ent) when optical active material, coming from optical resolution successively described, is used in the reductive process.

EXAMPLE 59

Free ketone is obtained by treatment of a solution of 3-endo hydroxy-2-exohydroxymethyl-bicyclo[5.3.0]-decane-8-one-8,8-ethylenedioxide (5 g, $2.10^{-2}$ m) in methanol (20 ml) and water (2 ml) with p-toluenesulphonic acid (0.3 g) for 2 hours at reflux temperature. The solvents are evaporated in vacuum and the residue is filtered through a short column of $SiO_2$.

Working in accordance with the procedure of the example 54, a solution of the so obtained 3-endo-hydroxy-2-exo-hydroxymethyl-bicyclo[5.3.0]8-one (4.7 g) in dry DMSO (17 ml) is reacted with the ylide formed from potassium ter-butoxide (27 g), DMSO (280 ml) and 3-carboxy-propyl-phosphoniumbromide for 5 hours at 40°. The reaction mixture is diluted with water (300 ml) and extracted with 80:20 ethylether-benzene to remove triphenylphosphoxide. These extracts are discarded and alkaline phases are acidified up to pH 5 and repeatedly extracted with ethylether (8×200) and with 3:1 ethylether-ethylacetate (5×100). The combined organic extracts are dried, concentrated to a small volume (100 ml) treated with ethereal diazomethane to achieve the methyl ester and then evaporated to dryness.

The crude material is chromatographed on $SiO_2$ (100 g) (ethylacetate as eluent) to give 5 (Z,E)-ω(20→12) octanor-12β-hydroxymethyl-11α-hydroxy-9a-deoxy-9a,9b,7-homo-trimethylene-2-nor-prostacycla-5-enoic acid methylester (4.1 g).

By treating this compound in dry DMF (12 ml) with dimethyl-ter-butyl-silylchloride (2.2 g) in imidazole (1.55 g) at 15° for 24 hours, followed from dilution with water (24 ml) and extraction with ethylether and chromatographic purification on $SiO_2$ (25 g, cyclohexane-ethylether as eluent) we obtain its mono 12β-DMB-silyloxy methyl-ether (4.31 g 80%).

Treatment with pyridine (10 ml), acetic anhydride (5 ml) at r.t. for 12 hours and hydrolysis with aqueous methanol and p-toluensulphonic acid afford 5(Z,E)-ω-(20→12) octanor-12β-hydroxymethyl-11α-hydroxy-9a-deoxy-9a,9b-7a homo-trimethylene-2-nor-prostacycla-5-en-oic acid methylester-11-acetate. Preparative chromatography (using a HPLC-instrument and monitoring with refractive index) on $SiO_2$ treated with 3% $AgNO_3$ (with methylenechlorideethylacetate as eluent) affords the individual geometric 5 c and 5t isomers. In similar way, 5(Z,E)-ω-(20→12)octanor-12β-hydroxymethyl-11α-hydroxy-9a-deoxy-9a,7a-homo-dimethylene-prostacycla-5-enoic acid methyl ester-11-acetate and their 5c and 5t individual geometric isomers are prepared when 3-endo-hydroxy-bicyclo[4.3.0]nonane-7-one-2-exo-carboxymethylester-7,7-ethylenedioxide is used in side of the corresponding per-hydroazulene compound and the 4-carboxybutylphosphonium bromide is utilized in side of the 3-carboxypropyl-one.

EXAMPLE 60

Starting from the 2-exo-hydroxymethyl-THP-ether compounds of the example 58 and from 12β-hydroxymethyl-11-acetate of the example 59, we have obtained the corresponding aldehydes by the following oxidative procedure: Successively, dicyclohexylcarbodiimide (0.64 g), pyridine (0.1 ml) trifluoroacetic acid (0.05 ml) are added to a stirred solution of the hydroxymethyl compound ($2.10^{-3}$ m) in 75:25 benzene-DMSO (6 ml). After 4.5 hours, the reaction mixture is diluted with benzene (20 ml) and water (10 ml) and stirred for 30 minutes again. Dicyclohexylurea is filtered off and the organic layer is washed with water until neutral and the concentrated up to 10 ml affording a solution in dry benzene of the following aldehydes:
3-endo-THP-oxy-2-exo-formyl-bicyclo[3.2.0]heptane-6-one-6,6-ethylene dioxide
3-endo-THP-oxy-2-exo-formyl-bicyclo[3.2.0]heptane-7-one-7,7-ethylene dioxide
3-endo-THP-oxy-2-exo-formyl-bicyclo[4.3.0]nonane-7-one-7,7-ethylene dioxide
3-endo-THP-oxy-2-exo-formyl-bicyclo[4.3.0]nonane-8-one-8,8-ethylene dioxide
3-endo-THP-oxy-2-exo-formyl-bicyclo[5.3.0]decane-8-one-8,8-ethylene dioxide
ω(20→12)octanor-12β-formyl-11α-hydroxy-9a-deoxy-9a,9b-7-homo-trimethylene-2-nor-prostacycla-5-enoic acid methylester-11-acetate (5(Z,E); 5c; 5t).
ω(20→12)octanor-12β-formyl-11α-hydroxy-9a-deoxy-9a,7a-homo-dimethylene-prostacycla-5-enoic acid methylester-11-acetate (5(Z,E); 5c, 5t). These compounds are used in the following Wittig-Horner reactions with any further purification.

EXAMPLE 61

A solution of (2-oxo-heptyl)dimethylphosphonate (0.49 g) in benzene (6 ml) is added dropwise to a stirred suspension of NaH (80% dispersion in mineral oil, 66 mg, $2.2.10^{-3}$ m) in benzene (15 ml). After an additional stirring for 45' we add a solution of $2.10^{-3}$ m of 5 t-ω(20→12)octanor-12β-formyl-11α-hydroxy-9a-deoxy-9a,9b,7a-homo-trimethylene-2-nor-prostacycla-5enoic acid methylester-11-acetate in benzene (10 ml) to it. After an additional hour the reaction is stopped by adding a solution of acetic acid (132 mg) in benzene (5 ml); the organic phase is washed with water until neutral, dried and evaporated to dryness.

The residue, 1.2 g, is absorbed on $SiO_2$ (10 g), following elution with cyclohexane-ethylacetate gives 5t,13t-11α-hydroxy-15-oxo-9a-deoxy-9a,9b,7a-homo-trimethylene-2-nor-prostacycla-5,13-dienoic acid methyl ester-11-acetate (0.76 g), λ max 228 mµ ε=9.800.

The following α,β-unsaturated ketones are obtained when the other aldehydes of the example 60 are used in the above procedure:
5c,13t-11α-hydroxy-15-oxo-9a-deoxy-9a,9b,7a-homo-trimethylene-2-nor prostacycla-5,13-dienoic acid-methylester-11-acetate λ max 228 mµ, ε=9.900 and the mixture of their 5(Z,E) isomers
5t,13t-11α-hydroxy-15-oxo-9a-deoxy-9a,7a-homo-dimethylene-prostacycla-5,13-dienoic acid methylester-11-acetate (λ max 229 mµ, ε=10.000) and its 5t and 5(Z,E)-isomers
and the following 2-exo[3'-oxo-oct-1'-trans-enyl]3-endo-hydroxy-THP-ethers:
bicyclo[3.2.0]heptane-6-one-6,6-ethylenedioxide
bicyclo[3.2.0]heptane-7-one-7,7-ethylenedioxide
bicyclo[4.3.0]nonane-7one-7,7-ethylenedioxide
bicyclo[4.3.0]nonane-8-one-8,8-ethylenedioxide
bicyclo[5.3.0]decane-8-one-8,8-ethylenedioxide.

EXAMPLE 62

Using in the procedure of the example 61, different dimethylphosphonates we have prepared the following α,β-unsaturated ketones:
(a) by reaction of 3-endo-THP-oxy-2-exo-formyl-bicyclo[3.2.0]heptane-7-one-7,7-ethylenedioxide ($2.10^{-3}$ m) with (2-oxo-3(S,R)-fluoro-heptyl)dimethyl phosphonate (0.54 g) we obtain 3-endo-THP-oxy-2-exo[3'-oxo-4'(R,S)fluorooct-1'-trans-enyl]bicyclo[3.2.0]heptane-7-one-7,7-ethylenedioxide (0.72 g) λ max 229 nm, ε=9.900, [α]$_D$=+98° (CHCl$_3$)
(b) by reaction of the heptane-6-one-6,6-ethylenedioxide aldehyde ($2.10^{-3}$ m) with (2-oxo-octyl)dimethylphosphonate we obtain 3-endo-THP-oxy-2-exo[3'-oxo-non-1'-trans-enyl]bicyclo[3.2.0]heptane-6-one-6,6-ethylenedioxide λ max 228 nm ε=9.300
(c) by reaction with the heptane-7-one-7,7-ethylenedioxidealdehyde with (2-oxo-4-phenyl-butyl)dimethylphosphonate (0.565 g) we obtain 3-endo-THP-oxy-2-exo-[3'-oxo-5'-phenyl-pent-1'-trans-enyl]bicyclo[3.2.0]heptane-7-one-7,7-ethylenedioxide
(d) by reaction with the nonane-7-one-7,7-ethylenedioxide with 0.52 g of (2-oxo-3S-methylheptyl) and with (2-oxo-3R-methyl-heptyl)dimethyl phosphonate we obtain respectively:

3-endo-THP-oxy-2-exo[3'-oxo-4'S-methyl-oct-1'-trans-enyl]bicyclo[4.3.0]nonane-7-one-7,7-ethylenedioxide and 3-endo-THP-oxy-2-exo[3'-oxo-4'R-methyl-oct-1'-trans-enyl]bicyclo[4.3.0]nonane-7-one-7,7-ethylenedioxide.

EXAMPLE 63

Pyridine hydrobromideperbromide ($C_5H_5N.HBr.Br_2$), 0.8 g, is added to a stirred solution of 3-endo-THP-oxy-2-exo[3'-oxo-4'(R,S)-fluoro-oct-1'-trans-enyl]bicyclo[3.2.0]heptane-7-one-7,7-ethylenedioxide in dry pyridine (15 ml). After additional stirring for 4 hours at r.t., the precipitate is filtered off and the organic eluate is partitioned among ice, 2 N $H_2SO_4$ and ethylacetate. The organic layer is washed with cooled 0.5 N $H_2SO_4$, brine 1% sodium carbonate, water until neutral affording 0.71 g of 2'-bromo-4'(R,S)-fluoro compound, which is a mixture of 2-diasteroisomeric 4'S and 4'R derivatives. HPLC-chromatography on $SiO_2$ with $CH_2Cl_2$-ethylether (85:15) affords the individual isomers:

0.22 g of 3-endo-THP-oxy-2-exo[2'bromo-3'-oxo-4'R-fluoro-oct-1'-trans-enyl]bycicylo[3.2.0]heptane-7-one-7,7-ethylenedioxide λ max 250 nm $\epsilon=9.830$ and 0.19 g of the 4'S-fluoro isomer λ max 251 nm $\epsilon=9.750$.

Using in the above procedure different α,β-unsaturated ketones, we obtain the followings:

3-endo-THP-oxy-2-exo[2'bromo-3'-oxo-non-1'-trans-enyl]bicyclo[3.2.0]heptane-6-one-6,6-ethylenedioxide and 3-endo-THP-oxy-2-exo[2'bromo-3'-oxo-oct-1'-trans-enyl]bicyclo[4.3.0]nonane-7-one-7,7-ethyelendioxide.

EXAMPLE 64

An ethereal solution of 5% methylmagnesium iodide (5 ml) is added to a stirred solution of 5t,13t-11α-hydroxy-15-oxo-9a-deoxy-9a,7a-homo-dimethylene-prostacycla-5,13-dienoic acid methylester (0.4 g) in 2:1 ethyl ether-toluene (12 ml), cooled at −30°. After stirring for additional 4 hours, the reaction mixture is warmed to 0° and the residual reagent is destroyed by adding of 20% aqueous $NH_4Cl$. The organic layer is separated, washed with water, dried and after addition of pyridine (0.1 ml) is evaporated to dryness. The residue dissolved in dry methanol (10 ml) is stirred with anhydrous $K_2CO_3$ (0.1 g) for 2 hours. The solution is filtered, evaporated in vacuum and the resulting crude material is partitioned between ethyl acetate 20% $NaH_2PO_4$. The organic layer after the usual work-up is concentrated to small volume; the residue is absorbed on $SiO_2$ (20 g). Elution with 80:20 ethylether: isopropylether gives 5t,13t-11α,15S-dihydroxy-15-methyl-9a-deossi-9a,7a-homo-dimethylene-prostacycla-5,13-dienoic acid methylester (0.1 g) and its 15R-isomer (0.085 g).

With this procedure it is also obtained:

5t,13t-11α,15S-dihydroxy-15-methyl-9a-deoxy-9a,9b,7a-homo-trimethylene-2-nor-prostacycla-5,13-dienoic acid-methylester and its 15R-epimer.

The free acids are obtained heating at the reflux temperature a solution of methylesters in 80:20 methanol-water in the presence of 2% $K_2CO_3$. The solvent is evaporated in vacuum and the residue is partitioned between ethylether and water. The organic layers are reextracted with 0.5% $K_2CO_3$ and discarded. The combined alkaline phases are acidified up to pH 6 and extracted with ethylether. Combined organic phases are washed, dried on $MgSO_4$ and evaporated to dryness to give free acids.

EXAMPLE 65

Using in the procedure of the example 64 ethynyl magnesium bromide, vinyl magnesium bromide and ethyl magnesium bromide in side of the methyl magnesium iodide, the corresponding 15-ethynyl, 15-vinyl and 15-ethyl prostacycladienoic acids are obtained.

EXAMPLE 66

Starting from the α,β-unsaturated ketones of the examples 61,62,63, secondary allylic alcohols are obtained using the following procedure: a solution of α,β-unsaturated ketone ($2.10^{-3}$ m) in dry ethylether (20 ml) is added to a stirred solution of 0.25 M zinc borohydride (48 ml) in dry ethylether, dropwise in a period of 30 minutes. After an additional stirring for 2 hours, the residual hydride is destroyed by adding saturated NaCl. The organic layer is separated, washed until neutral, dried on $Na_2SO_4$ and evaporated to dryness. Preparative HPLC-chromatography on $SiO_2$, using as eluent methylene chloride/ethylacetate, affords:

5c,13t-11α,15S-dihydroxy-9a-deoxy-9a,9b,7a-homo-trimethylene-2-nor-prostacycla-5,13-dienoic acid methylester-11-acetate and its 5(Z,E) and 5t geometric isomers.

5t,13t-11α,15S-dihydroxy-9a-deoxy-9a,7a-homo-dimethylene-prostacycla-5,13-dienoic acid methylester-11-acetate and its 5(Z,E) and 5c-geometric isomers.

The following 2-exo[3'S-hydroxy-oct-1'-trans-enyl]3-endo-THP-oxy:

bicyclo[3.2.0]heptane-6-one-6,6-ethylenedioxide
bicyclo[3.2.0]heptane-7-one-7,7-ethylenedioxide
bicyclo[4.3.0]nonane-7-one-7,7-ethylenedioxide
bicyclo[4.3.0]nonane-8-one-8,8-ethylenedioxide and the following 3-endo-THP-oxy:

2-exo[2'bromo-3'S-hydroxy-4'R-fluoro-oct-1'-trans-enyl]bicyclo[3.2.0]heptane-7-one-7,7-ethylenedioxide
2-exo[2'bromo-3'S-hydroxy-4'S-fluoro-oct-1'-trans-enyl]bicyclo[3.2.0]heptane-7-one-7,7-ethylenedioxide
2-exo[2'bromo-3'S-hydroxy-non-1'-trans-enyl]bicyclo[3.2.0]heptane-6-one-6,6-ethylenedioxide
2-exo[3'S-hydroxy-non-1'-trans-enyl]bicyclo[3.2.0]heptane-6-one-6,6-ethylenedioxide
2-exo[3'S-hydroxy-5'-phenyl-pent-1'-trans-enyl]bicyclo[3.2.0]heptane-7-one-7,7-ethylenedioxide
2-exo[2'bromo-3'S-hydroxy-oct-1'-trans-enyl]bicyclo[4.3.0]nonane-7-one-7,7-ethylenedioxide
2-exo[3'S-hydroxy-4'S-methyl-oct-1'-trans-enyl]bicyclo[4.3.0]nonane-7-one-7,7-ethylenedioxide
2-exo[3'S-hydroxy-4'R-methyl-oct-1'-trans-enyl]bicyclo[4.3.0]nonane-7-one-7,7-ethylenedioxide
5c,13t-11α,15R-dihydroxy-9a-deoxy-9a,9b,7a-homo-trimethylene-2-nor-prostacycla-5,13-dienoic acid methylester-11-acetate and its 5(Z,E) and 5t geometric isomers.
5t,13t-11α,15R-dihydroxy-9a-deoxy-9a,7a-homo-dimethylene-prostacycla-5,13-dienoic acid methylester-11-acetate and its 5(Z,E) and 5c-geometric isomers.

The following 2-exo[3'R-hydroxy-oct-1'-trans-enyl]3-endo-THP-oxy:

bicyclo[3.2.0]heptane-6-one-6,6-ethylenedioxide
bicyclo[3.2.0]heptane-7-one-7,7-ethylenedioxide bicyclo[4.3.0]nonane-7-one-7,7-ethylenedioxide
bicyclo[4.3.0]nonane-8-one-8,8-ethylenedioxide
and the following 3-endo-THP-oxy:
2-exo[2'bromo-3'R-hydroxy-4'R-fluoro-oct-1'-trans-enyl]bicyclo[3.2.0]heptane-7-one-7,7-ethylenedioxide
2-exo[2'bromo-3'R-hydroxy-4'S-fluoro-oct-1'-trans-enyl]bicyclo[3.2.0]heptane-7-one-7,7-ethylenedioxide
2-exo[2'bromo-3'R-hydroxy-non-1'-trans-enyl]bicyclo[3.2.0]heptane-6-one-6,6-ethylenedioxide
2-exo[3'R-hydroxy-non-1'-trans-enyl]bicyclo[3.2.0]heptane-6-one-6,6-ethylenedioxide
2-exo[3'R-hydroxy-5'-phenyl-pent-1'-trans-enyl]bicyclo[3.2.0]heptane-7-one-7,7-ethylenedioxide
2-exo[2'bromo-3'R-hydroxy-oct-1'-trans-ethyl]bicyclo[4.3.0]nonane-7-one-7,7-ethylenedioxide
2-exo[3'R-hydroxy-4'S-methyl-oct-1'-trans-enyl]bicyclo[4.3.0]nonane-7-one-7,7-ethylenedioxide
2-exo[3'R-hydroxy-4'R-methyl-oct-1'-trans-enyl]bicyclo[4.3.0]nonane-7-one-7,7-ethylenedioxide

EXAMPLE 67

The individual 11-acetate prostacycladienoic acid methylesters are converted both in their 11-hydroxy methylesters by trans esterification in dry methanol with anhydrous $K_2CO_3$ (0.5 mol equiv) and in their 11-hydroxy free acid by treatment with $K_2CO_3$ in 80% aqueous methanol.

EXAMPLE 68

Every one of the bicyclo-THP-oxy-ethylenedioxides obtained in the procedure of the example 66 is converted into the corresponding prostacyclenoic acids working up with the following procedure: a solution of $1.10^{-3}$ m. of the bicyclo-THP-oxy-ethylenedioxide in acetone (15 ml) is refluxed with N aqueous oxalic acid (10 ml) for 8 hours. The acetone is evaporated in vacuum and the aqueous phase is extracted with ethylether. The combined extracts after the usual work-up, are evaporated to dryness affording about $0.6-1.10^{-3}$ m. of the hydroxy ketone. A solution of this compound in dry DMSO (2 ml) is added to a solution of the ylide obtained so on: in a $N_2$ atmosphere potassium-tert-butoxide (1.35 g) is added to dry DMSO (15 ml), then to it we added 4-carboxy-butyl-triphenyl-phosphoniumbromide (2.6 g) to obtain a deep-red solution of the ylide. After addition of the ketone, the reaction mixture is warmed at 40°-42° for 6 hours, cooled, diluted with water (20 ml), acidified up to pH 5.1 and extracted with ethylether (5×25 ml).

The aqueous phase is discarded, and the organic extracts are collected, washed with water (5 ml; this washing is descarded) and extracted with 0.5 N NaOH (6×6 ml) and water until neutral. The combined alkaline extracts are combined, acidified to pH 5 and extracted with ethylether. The combined organic extracts are washed with water (2 ml), dried on $Na_2SO_4$, and evaporated to dryness giving a mixture of the 5 Z and 5 E acids.

The individual geometric isomers are obtained after chromatographic separation on acidic $SiO_2$ ($Fe^{++}$, $Fe^{+++}$ free) using $CH_2Cl_2$-ethylacetate as eluent ($SiO_2$ 30 g for each of 0.2 g of the acid).

In this way we have prepared:
5t,13t-11α,15S-dihydroxy-9a-deoxy-9a-nor-methylene-prostacycla-5,13-dienoic acid
5t,13t-11α,15S-dihydroxy-9a-deoxy-9a-nor-methylene-20-methyl-prostacycla-5,13-dienoic acid
5t-11α,15S-dihydroxy-9a-deoxy-9a-nor-methylene-20-methyl-prostacycla-5-en-13-ynoic acid
5t,13t-11α,15S-dihydroxy-9a-deoxy-9a-methylene-7a-nor-methyleneprostacycla-5,13-dienoic acid
5t,13t-11α,15S-dihydroxy-9a-deoxy-9a,7a-homo-dimethylene-prostacycla-5,13-dienoic acid
5t,13t-11α,15S-dihydroxy-9a-deoxy-9a,9b-dimethylene-prostacycla-5,13-dienoic acid
5t-11α,15S-dihydroxy-9a-deoxy-9a-methylene-7a-nor-methylene-16S-fluoroprostacycla-5-en-13-ynoic acid
5t-11α,15S-dihydroxy-9a-deoxy-9a-methylene-7a-nor-methylene-16R-fluoroprostacycla-5-en-13-ynoic acid
5t,13t-11α,15S-dihydroxy-9a-deoxy-9a-methylene-7a-nor-methylene-17-phenyl-18,19,20-trinor-prostacycla-5,13-dienoic acid
5t,13t-11α,15S-dihydroxy-9a-deoxy-9a,7a-homo-dimethylene-16S-methylprostacycla-5,13-dienoic acid
5t,13t-11α,15S-dihydroxy-9a-deoxy-9a,7a-homo-dimethylene-16R-methylprostacycla-5,13-dienoic acid
5t-11α,15S-dihydroxy-9a-deoxy-9a,7a-homo-dimethylene-prostacycla-5-en-13-ynoic acid
5c,13t-11α,15S-dihydroxy-9a-deoxy-9a-nor-methylene-prostacycla-5,13-dienoic acid
5c,13t-11α,15S-dihydroxy-9a-deoxy-9a-nor-methylene-20-methyl-prostacycla-5,13-dienoic acid
5c-11α,15S-dihydroxy-9a-deoxy-9a-nor-methylene-20-methyl-prostacycla-5-en-13-ynoic acid
5c-13t-11α,15S-dihydroxy-9a-deoxy-9a-methylene-7a-nor-methylene-prostacycla-5,13-dienoic acid
5c,13t-11α,15S-dihydroxy-9a-deoxy-9a,7a-homo-dimethylene-prostacycla-5,13-dienoic acid
5c,13t-11α,15S-dihydroxy-9a-deoxy-9a,9b-dimethylene-prostacycla-5,13-dienoic acid
5c-11α,15S-dihydroxy-9a-deoxy-9a-methylene-7a-nor-methylene-16S-fluoroprostacycla-5-en-13-ynoic acid
5c-11α,15S-dihydroxy-9a-deoxy-9a-methylene-7a-nor-methylene-16R-fluoroprostacycla-5-en-13-ynoic acid
5c,13t-11α,15S-dihydroxy-9a-deoxy-9a-methylene-7a-nor-methylene-17-phenyl-18,19,20-trinor-prostacycla-5,13-dienoic acid
5c,13t-11α,15S-dihydroxy-9a-deoxy-9a,7a-homo-dimethylene-16S-methylprostacycla-5,13-dienoic acid
5c,13t-11α,15S-dihydroxy-9a-deoxy-9a,7a-homo-dimethylene-16R-methylprostacycla-5,13-dienoic acid
5c-11α,15S-dihydroxy-9a-deoxy-9a,7a-homo-dimethylene-prostacycla-5-en-13-ynoic acid and their 15R-isomers.

EXAMPLE 69

Successively dicyclohexylcarbodiimide (0.32 g) pyridine (0.044 ml) and trifluoroacetic acid (0.022 ml) are added to a stirred solution of 5t,13t-11α,15S-dihydroxy-9a-deoxy-9a,7a-homo-dimethylene-15-methyl-prostacycla-5,13-dienoic acid methylester (0.39 g) in 75:25 benzene-DMSO (6 ml). After 5 hours the reaction mixture is diluted with benzene (20 ml) and 1.2 g of oxalic acid in water (10 ml). The stirring is continued for 20 minutes, the mixture is filtered and the organic phase is washed until neutral, dried and finally evaporated to dryness.

Chromatographic purification on $SiO_2$ (4 g), ethyl ether as eluent, gives 0.26 g of 5t,13t-11-oxo-15S-hydroxy-9a-deoxy-9a,7a-homo-dimethylene-15-methylprostacycla-5,13-dienoic acid methylester which is hydrolysed with 2% aqueous $K_2CO_3$ to give the free acid.

EXAMPLE 70

Sodium borohydride (2.5 g) in portionwise is added to a stirred solution of bicyclo[4.3.0]nonane-7-en-3-one (11.42 g) in ethanol (80 ml). After an additional stirring for 2 hours, acetic acid (5 ml) is added and the mixture is evaporated to dryness. The residue is partitioned between water and $CH_2Cl_2$, and the organic layer is evaporated to dryness. A solution of the the resulting bicyclo[4.3.0]nonane-7-en-3-hydroxy (11 g) in dry DMF is heated successively with dimethyl-tert-butylsilyl-chloride (15.6 g) and imidazole (10.85 g), warmed at 60° for 6 hours, cooled and diluted with water (66 ml). After exhaustive extraction with ethylether and usual work-up we obtain bicyclo[4.3.0]nonane-7-ene-3-hydroxy-3-DMB-silyl-ether (19.1 g). Its solution in dry THF (100 ml), cooled to 0° C. is treated (under stirring, in $N_2$ atmosphere) with $MBH_3$ solution in THF (75 ml). After 2 hours, maintaining the temperature at 25°, we add N NaOH (25 ml) and 30% hydrogen peroxide (25 ml). The mixture is heated at 60S° for 2 hours, cooled and diluted with benzene (400 ml). The organic layer is washed with 1% $Na_2CO_3$, saturated sodium sulphite, saturated NaCl, dried and evaporated to dryness giving crude bicyclo[4.3.0]nonane-7(8)ξ-3-dihydroxy-3-DMB-silylether (20.3 g). A solution of the resulting alcohol in 75/25 benzene-DMSO (150 ml) is treated successively with dicyclohexylcarbodiimide (16 g) pyridine (2 ml) trifluoro acetic acid (1 ml), under stirring. After 5 hours, the mixture is diluted with benzene (400 ml), water (50 ml) with a solution of oxalic acid (6 g) in water (75 ml), and after additional stirring for 30 minutes is filtered. The organic phase is washed with water until neutral affording bicyclo[4.3.0]nonane-7(8)-one-3-hydroxy-DMB-silylether (18.25 g) which is dissolved in methanol (60 ml) and treated with 1.8 g of p-toluenesulfonic acid. After 12 hours, the mixture is treated with pyridine (1.95 ml) and evaporated to dryness. The residue is filtered on $SiO_2$ (ethylether-ethylacetate as eluent) to give bicyclo[4.3.0]nonane-7(8)-one-3-hydroxy (10 g).

A solution of this compound in benzene (50 ml) is refluxed in the presence of dry ethylene glycol (5.2 g) and p-toluenesulfonic acid (0.62 g) withdrawing the water formed during the reaction. After 14 hours we add pyridine (2 ml) and the organic phase is cooled, washed with water, 2% $Na_2CO_3$ and saturated NaCl until neutral. Evaporation of solvents gives bicyclo[4.3.0]nonane-7(8)-one-3-hydroxy-7,7(8,8)-ethylenedioxide.

EXAMPLE 71

Saponification with 2% $K_2CO_3$ in 80% aqueous methanol of the dl-3-endohydroxy-bicyclo[4.3.0]nonane-8-one-8,8-diethylenedioxide-2-exo-carboxymethylester (4.5 g) gives the free acid (4.2 g).

To a solution of the free acid (4.2 g) in acetonitrile (120 ml) it is added d(+)-ephedrine (2.3 g); after 4 hours at r.t. 2.8 g of salt crystalizes giving after further crystallization from acetonitrile 2.15 g of (+)bicyclo[4.3.0]nonane-8-one-8,8-ethylenedioxide-3-endo-hydroxy-2-exo-carboxylic acid d(+)-ephedrinium salt. All the liquor waters are combined, evaporated to dryness; the residue is dissolved in water and treated with N NaOH up to alkaline pH (12-13). d(+)-Ephedrine is recovered by extraction with ether, then alkaline aqueous solution is acidified to pH 5 extracted with ethylacetate and organic layer combined are evaporated to dryness. The residue is diluted in acetonitrile and the procedure is repeated using (−)ephedrine to give (−)bicyclo[4.3.0]nonane-8-one-8,8-ethylenedioxide-3-endo-hydroxy-2-exo-carboxylic acid 1(−)-ephedrinium salt. Every one of the salts is separately dissolved in water/NaOH; the optically active base is recovered by extraction with ethylether, the alkaline aqueous phase is acidified up to pH 5-5, 1 and extracted with ethylacetate, affording (+)bicyclo[4.3.0]nonane-8-one-8,8-ethylendioxide-3-endo-hydroxy-2-exocarboxylic acid and (−)bicyclo[4.3.0]nonane-8-one-8,8-ethylenedioxide-3-endo-hydroxy-2-exocarboxylic acid, which are converted into the methylester with diazomethane treatment.

EXAMPLE 72

A solution of 26 g of dl-3-endo-hydroxy-bicyclo[4.3.0]-2-exo-carboxymethylester-7-one-7,7-ethylenedioxide in acetone (100 ml) is refluxed with 2 N $H_2SO_4$ (20 ml) for 4 hours.

Acetone is evaporated in vacuum and aqueous phase is extracted with ethylacetate. Combined organic extracts are washed until neutral, dried and evaporated to give 21.2 g of dl-3-endo-hydroxy-bicyclo[4.3.0]-2-exocarboxymethylester-7-one. To a solution of the ketone in dry acetonitrile (250 ml) it is added d-l-phenyl-1-ethyl-amine (12.1 g) and solvent is slowly distilled off recovering 50 ml in 30′ minutes. The mixture is slowly cooled at r.t. and then 12.12 g of (+) 3-endo-hydroxy-7,7-(1′-phenyl-1′-ethylidenimino)-2-exo-carboxymethylester-bicyclo[4.3.0]are collected after filtration. The liquor waters are concentrated further to give 6 g of racemic material. Finally, a further concentration up to 80 ml affords 11.42 g of (−)3-endo-hydroxy-7,7(1′-phenyl-1′-ethylidenimino)-2-exo-carboxymethylester-bicyclo[4.3.0].

Separately, the two Schiff bases are cleaved with 80:20 methanol 2 N $H_2SO_4$ ₅(200 ml) at reflux temperature for 2 hours. Solvent is evaporated in vacuum and after extraction with ethylacetate, the combined organic phases are washed until neutral, dried and evaporated in vacuum to give:

8.1 g of (+)3-endo-hydroxy-bicyclo[4.3.0]2-exo-carboxymethylester-7-one and 7.2 g of (−)3-endo-hydroxy-bicyclo[4.3.0]2-exo-carboxymethylester-7-one, respectively.

Using this procedure, all the bicyclo-β-hydroxy-carboxylic ester-ethylene dioxides of the example 57 are submitted to optical resolution to give the following 3-endo-hydroxy alcohols:

(+)bicyclo[3.2.0]heptane-6-one-2-exo-carboxymethylester (+)bicyclo[3.2.0]heptane-7-one-2-exo-carboxymethylester (+)bicyclo[4.3.0]nonane-7-one-2-exo-carboxymethylester (+)bicyclo[4.3.0]nonane-8-one-2-exo-carboxymethylester (+)bicyclo[5.3.0]decane-8-one-2-exo-carboxymethylester (−)bicyclo[3.2.0]heptane-6-one-2-exo-carboxymethylester (−)bicyclo[3.2.0]heptane-7-2-exo-carboxymethylester (−)bicyclo[4.3.0]nonane-7-one-2-exo-carboxymethylester (−)bicyclo[4.3.0]nonane-8-one-2-exo-carboxymethylester (—)bicyclo[5.3.0]decane-8-one-2-exo-carboxymethylester Using the procedure of the example 56; these ketones are converted into their ethylenedioxide derivatives.

We claim:

1. Compounds having the following formula (I)

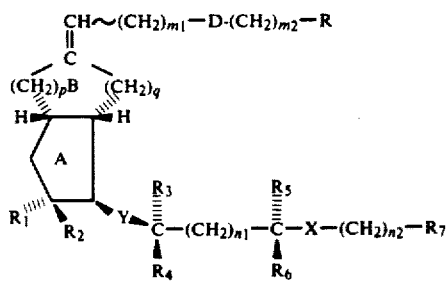

wherein

R is chosen from the group (a) a free carboxy group or an esterified carboxy group of formula —COOR$_9$ wherein R$_9$ is C$_1$–C$_{12}$ alkyl or C$_2$–C$_{12}$ alkenyl; (b) —C(OR')$_3$, where each R' group is independently C$_1$–C$_6$ alkyl or phenyl; (c) —CH$_2$—R", where R" is hydroxy or C$_2$–C$_7$ alkoxy; (d)

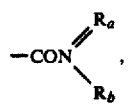

where R$_a$ and R$_b$ are chosen independently from the group hydrogen, C$_1$–C$_6$ alkyl, C$_2$–C$_6$ alkanoyl and phenyl; (e) —C≡N; (f)

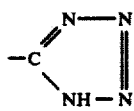

radical; (g) —CHO; (h) a

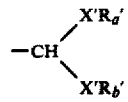

radical where each X' is independently —O— or —S— and the R'$_a$ and R'$_b$ groups, whether the same or different, are C$_1$–C$_6$ alkyl or together form a straight or branched C$_2$–C$_6$ alkylene chain; D is chosen from the group; —CH$_2$—, >CH—OH,

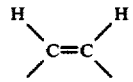

(cis),

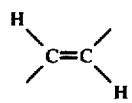

(trans), —C≡C—, >C=O, —O—, —S—, and >N—R$_c$, where R$_c$ may be hydrogen, C$_1$–C$_6$ alkyl or C$_2$–C$_6$ alkanoyl;

one of R$_1$ and R$_2$ and, independently, one of R$_3$ and R$_4$ is hydrogen, C$_1$–C$_6$ alkyl, C$_2$–C$_{10}$ alkenyl, C$_2$–C$_{10}$ alkynyl, phenyl, phenyl-C$_1$–C$_6$alkyl, α-naphthyl-C$_1$–C$_6$alkyl, or β-naphthyl-C$_1$–C$_6$alkyl and the other is hydrogen, hydroxy, C$_1$–C$_6$alkoxy, phenyl-C$_1$–C$_6$alkoxy, α-naphthyl-C$_1$–C$_6$alkoxy, or β-naphthyl-C$_1$–C$_6$alkoxy, or, R$_1$ and R$_2$ and, independently, R$_3$ and R$_4$ together form an oxo group;

each R$_5$ and R$_6$, whether the same or different, may be hydrogen, C$_1$–C$_6$ alkyl or halogen, or R$_5$, R$_6$ and the carbon atom to which they are bound from a >C=CH$_2$ or

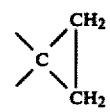

radical;

Y is —NH—CO— or —NH—CH$_2$—;

X is chosen from the group: —(CH$_2$)$_{m_3}$— in which m$_3$ is zero or 1,

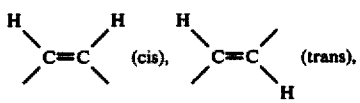

—O—, —S— and >N—R$_c$ with R$_c$ as defined above;

m$_1$, m$_2$, n$_1$ and n$_2$, whether the same or different, may be zero or an integer between 1 and 12 such that each sum m$_1$+m$_2$ and n$_1$+n$_2$ is less than or equal to 15;

p=q=1;

R$_7$ is chosen from the group: (a') hydrogen; (b') C$_1$–C$_4$ alkyl; (c') a cycloaliphatic radical, either unsubstituted or substituted with one or more C$_1$–C$_6$-alkyl or C$_1$–C$_6$-alkoxy; (d') a phenyl, α-naphthyl or β-naphthyl group, either unsubstituted or substituted with one or more of the following: halogen, halo-C$_1$–C$_6$-alkyl, C$_1$–C$_6$-alkyl, C$_1$–C$_6$-alkoxy, phenyl; (e') a five or six membered heteromonocyclic ring either containing an only one heteroatom chosen from oxygen, sulphur and nitrogen or containing one oxygen and one nitrogen atom or containing two nitrogen atoms, wherein the said five or six membered heteromonocyclic ring may be unsubstituted or substituted with one or more of the following: halogen, halo-C$_1$–C$_6$ alkyl, C$_1$–C$_6$ alkoxy, phenyl, C$_1$–C$_6$ alkyl;

and the lactones derived from compounds with formula (I) wherein D is >CH—OH and R is —COOH and the pharmaceutically or veterinarily acceptable salts of the compounds of formula (I) wherein R is —COOH.

2. Compounds having the following formula (I)

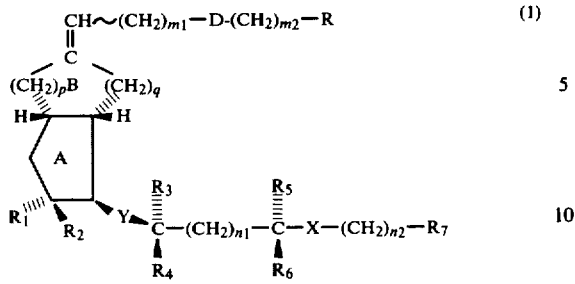

(1)

wherein

R is chosen from the group (a) a free carboxy group or an esterified carboxy group of formula —COOR$_9$ wherein R$_9$ is C$_1$–C$_{12}$ alkyl or C$_2$–C$_{12}$ alkenyl; (b) —C(OR')$_3$, where each R' group is independently C$_1$–C$_6$ alkyl or phenyl; (c) —CH$_2$—R'', where R'' is hydroxy or C$_2$–C$_7$ alkoxy; (d)

where R$_a$ and R$_b$ are chosen independently from the group hydrogen, C$_1$–C$_6$ alkyl, C$_2$–C$_6$ alkanoyl and phenyl; (e) —C≡N; (f) a

radical; (g) —CHO; (h) a

radical where each X' is independently —O— or —S— and the R'$_a$ and R'$_b$ groups, whether the same or different, are C$_1$–C$_6$ alkyl or together form a straight or branched C$_2$–C$_6$ alkylene chain;

D is chosen from the group: —CH$_2$—, >CH—OH,

(cis),

(trans), —C≡C—, >C=O, —O—, —S—, and >N—R$_c$, where R$_c$ may be hydrogen, C$_1$–C$_6$ alkyl or C$_2$–C$_6$ alkanoyl;

one of R$_1$ and R$_2$ and, independently, one of R$_3$ and R$_4$ is hydrogen, C$_1$–C$_6$ alkyl, C$_2$–C$_{10}$ alkenyl, C$_2$–C$_{10}$ alkynyl, phenyl, phenyl-C$_1$–C$_6$alkyl, α-naphthyl-C$_1$–C$_6$alkyl, or β-naphthyl-C$_1$–C$_6$alkyl and the other is hydrogen, hydroxy, C$_1$–C$_6$alkoxy, phenyl-C$_1$–C$_6$alkoxy, α-naphthyl-C$_1$–C$_6$alkoxy, or β-naphthyl-C$_1$–C$_6$alkoxy, or, R$_1$ and R$_2$ and, independently, R$_3$ and R$_4$ together form an oxo group;

each R$_5$ and R$_6$, whether the same or different, may be hydrogen, C$_1$–C$_6$ alkyl or halogen, or R$_5$, R$_6$ and the carbon atom to which they are bound form a >C=CH$_2$ or

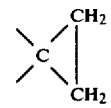

radical;

Y is —NH—CO— or —NH—CH$_2$;

X is chosen from the group: —(CH$_2$)$_{m3}$— in which m$_3$ is zero or 1;

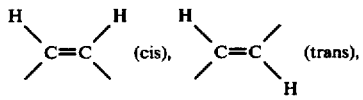

—O—, —S— and >N—R$_c$ with R$_c$ as defined above;

m$_1$, m$_2$, n$_1$ and n$_2$, whether the same or different, may be zero or an integer between 1 and 12 such that each m$_1$+m$_2$ and n$_1$+n$_2$ is less than or equal to 15; p=q=1;

R$_7$ is chosen from the group: (a') hydrogen; (b') C$_1$–C$_4$-alkyl; (c') a cycloaliphatic radical, either unsubstituted or substituted with one or more C$_1$–C$_6$-alkyl or C$_1$–C$_6$-alkoxy; (d') a phenyl, α-naphthyl or β-naphthyl group, either unsubstituted or substituted with one or more of the following: halogen, halo-C$_1$–C$_6$-alkyl, C$_1$–C$_6$-alkyl, C$_1$–C$_6$-alkoxy, phenyl; (e') a five or six membered heteromonocyclic ring chosen from the group consisting of tetrahydrofuryl, tetrahydrothienyl, tetrahydropyranyl, pyrrolyl, pyrazolyl, oxazolyl, isoxazolyl, pyridyl, pyrazinyl, pyrimidinyl, pyridazinyl;

and the lactones derived from compounds with formula (I) wherein D is >CH—OH and R is —COOH and the pharmaceutically or veterinarily acceptable salts of the compounds of formula (I) wherein R is —COOH.

3. Compounds having the formula (I) reported in the previous claims wherein D, m$_1$, m$_2$, p, q, R$_1$, R$_2$, Y, R$_3$, R$_4$, R$_5$, R$_6$, X, n$_1$ and n$_2$ have the meanings reported in claim 31; R is a free or salified carboxy group; R$_7$ is a straight or branched C$_1$–C$_4$ alkyl, phenyl optionally substituted as described in claim 31, a C$_5$–C$_7$ monocycloalkyl radical or a five or six membered heteromonocyclic ring as described in claim 2.

4. 5t-11α,15S-dihydroxy-9a-deoxy-9a-methylene-13-aza-14-oxo-prostacycla-5-enoic acid and the pharmaceutically or veterinarily acceptable salts thereof and the methyl ester thereof.

5. 5t-11α,15R-dihydroxy-9a-deoxy-9a-methylene-13-aza-14-oxo-prostacycla-5-enoic acid and the pharmaceutically or veterinarily acceptable salts thereof and the methyl ester thereof.

6. A pharmaceutical or veterinary composition suitable for use as an anti-aggregating agent or a dis-aggregating agent comprising a therapeutically effective amount of a compound according to any one of claims 1-3 and a pharmaceutically or veterinarily acceptable carrier and/or diluent.

7. A pharmaceutical or veterinary composition suitable for use in the curing or inhibiting of the formation of ulcers or controlling gastric secretions, comprising a therapeutically effective amount of a compound according to any one of claims 1-3 and a pharmaceutically or veterinarily acceptable carrier and/or diluent.

8. A pharmaceutical or veterinary composition suitable for including labor or expelling a dead fetus, said composition comprising a therapeutically effective amount of a compound according to any one of claims 1-3 and a pharmaceutically or veterinarily acceptable carrier and/or diluent.

9. A pharmaceutical or veterinary composition for producing a hypotensive effect, said composition comprising a therapeutically effective amount of a compound according to any one of claims 1-3 and a pharmaceutically or veterinarily acceptable carrier and/or diluent.

10. A composition for producing a luteolytic effect, said composition comprising a therapeutically effective amount of a compound according to any one of claims 1-3 and a pharmaceutically or veterinarily acceptable carrier and/or diluent.

11. A pharmaceutical or veterinary composition for relaxing coronary arteries, said composition comprising a therapeutically effective amount of a compound according to any one of claims 1-3 and a pharmaceutically or veterinarily acceptable carrier and/or diluent.

12. A pharmaceutical or veterinary composition suitable for producing a bronchdilatory effect, said composition comprising a therapeutically effective amount of a compound according to any one of claims 1-3 and a pharmaceutically or veterinarily acceptable carrier and/or diluent.

13. A method of inhibiting blood platelet aggregation or of dissolving recently formed blood clots, said method comprising contacting said blood platelets or said clots with an effective amount of a compound of claim 1, 2 or 3.

14. Method of claim 13, wherein said method is a method of inhibiting blood platelet aggregation, said blood platelets are in a patient, and said compound is administered to said patient.

15. Method of claim 13, wherein said method is a method of dissolving recently formed blood clots, said clots are in a patient, and said compound is administered to said patient.

16. A method of curing or inhibiting the formation of ulcers or controlling gastric secretions in a patient in need of such treatment, said method comprising administering to said patient an effective amount of a compound of claim 1, 2 or 3.

17. A method of inducing labor or expelling a dead fetus in a patient in need of such treatment, said method comprising administering to said patient an oxytocic effective amount of a compound of claim 1, 2 or 3.

18. A method of producing a hypotensive effect in a patient in need of such effect, said method comprising administering to said patient a hypotensive effective amount of a compound of claim 1, 2 or 3.

19. A method of producing a luteolytic effect in a patient in need of such effect, said method comprising administering to said patient an effective amount of a compound of claim 1, 2 or 3.

20. A method of relaxing coronary arteries in a patient in need of such relaxation, said method comprising administering to said patient an effective amount of a compound of claim 1, 2 or 3.

21. A method of producing a bronchodilatory effect in a patient in need of such effect, said method comprising administering to said patient an effective amount of a compound of claim 1, 2 or 3.

* * * * *